United States Patent
Glimcher et al.

(10) Patent No.: US 8,227,184 B2
(45) Date of Patent: Jul. 24, 2012

(54) METHODS FOR MODULATING DE NOVO HEPATIC LIPOGENESIS BY MODULATING XBP-1 ACTIVITY

(75) Inventors: Laurie H. Glimcher, West Newton, MA (US); Ann-Hwee Lee, Chestnut Hill, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 296 days.

(21) Appl. No.: 12/319,991

(22) Filed: Jan. 14, 2009

(65) Prior Publication Data

US 2009/0232738 A1 Sep. 17, 2009

Related U.S. Application Data

(60) Provisional application No. 61/011,070, filed on Jan. 14, 2008, provisional application No. 61/191,049, filed on Sep. 5, 2008.

(51) Int. Cl.
*C12Q 1/68* (2006.01)
(52) U.S. Cl. ........... 435/6; 435/325; 435/375; 536/24.5; 536/24.31; 536/24.1
(58) Field of Classification Search ........................ None
See application file for complete search history.

(56) References Cited

U.S. PATENT DOCUMENTS

2006/0063187 A1 * 3/2006 Hotamisligil et al. ............ 435/6
2006/0148739 A1 * 7/2006 Kotani et al. ................... 514/44

OTHER PUBLICATIONS

Ebrahimpour, et al. (2006) Abstract Only "Metabolic Syndrome and Related Insulin Levels in Obese Children," Metabolic Syndrome and Related Disorders, V.4(3):172-8.*
IRE1 Antibody (ab45973) [online]. [retrieved on Jan. 25, 2011]. Retrieved from the internet: <http://www.abcam.com/IRE1-antibody-ab45973.html>.*
XBP1 Antibody (ab37152) [online]. [retrieved on Jan. 25, 2011]. Retrieved from the internet: <http://www.abcam.com/XBP1-antibody-ab37152.html>.*
Ginsberg et al. (Obesity vol. 14, Feb. 2006: 41S-49S).*

* cited by examiner

*Primary Examiner* — Kimberly Chong
(74) *Attorney, Agent, or Firm* — Nelson Mullins Riley & Scarborough LLP; Debra J. Milasincic, Esq.

(57) ABSTRACT

The invention provides methods and compositions for modulating the expression, processing, post-translational modification, stability and/or activity of XBP-1 protein, or a protein in a signal transduction pathway involving XBP-1 to treat dyslipidemias and steatosis disorders. The present invention also pertains to methods for identifying compounds that modulate the expression, processing, post-translational modification, and/or activity of XBP-1 protein or a molecule in a signal transduction pathway involving XBP-1.

19 Claims, 25 Drawing Sheets

METHODS FOR MODULATING DE NOVO HEPATIC LIPOGENESIS BY MODULATING XBP-1 ACTIVITY

RELATED APPLICATIONS

This application claim priority to U.S. Provisional Application No. 61/191,049, titled "Methods for Modulating De Novo Hepatic Lipogenesis by Modulating XBP-1 Activity", filed Sep. 5, 2008 and to U.S. Provisional Application No. 61/011,070, titled "Methods for Modulating De Novo Hepatic Lipogenesis by Modulating XBP-1 Activity", filed Jan. 14, 2008. This application is related to U.S. application Ser. No. 10/655,620, titled "Methods and Compositions for Modulating XBP-1 Activity" filed Sep. 2, 2003, the entire contents of which are incorporated herein by this reference.

GOVERNMENT FUNDING

Work described herein was supported, at least in part, under grant AI32412 and AI56296 awarded by the National Institutes of Health. The U.S. government, therefore, will have certain rights in this invention.

BACKGROUND OF THE INVENTION

The transcription factor XBP-1 was identified as a key regulator of the mammalian unfolded protein response (UPR) or endoplasmic reticulum (ER) stress response, which is activated by environmental stressors such as protein overload that require increased ER capacity (D. Ron, P. Walter (2007) *Nat Rev Mol Cell Biol* 8, 519). XBP-1 is activated by a post-transcriptional modification of its mRNA by IRE-1 alpha, an ER localizing proximal sensor of ER stress (M. Calfon et al. (2002) *Nature* 415, 92; H. Yoshida, et al: (2001) *Cell* 107, 881; X. Shen et al. (2001) *Cell* 107, 893). Upon ER stress, IRE-1 alpha induces an unconventional splicing of XBP-1 mRNA by using its endoribonuclease activity to generate a mature mRNA encoding an active transcription factor, XBP-1s, which directly binds to the promoter region of ER chaperone genes to promote transcription (A. L. Shaffer et al. (2004) *Immunity* 21, 81; A. H. Lee, et al. (2003) *Mol Cell Biol* 23, 7448; D. Acosta-Alvear et al. (2007) *Mol Cell* 27, 53). Mice deficient in XBP-1 display severe abnormalities in the development and function of professional secretory cells, such as plasma B cells and pancreatic acinar cells (N. N. Iwakoshi et al. (2003) *Nat Immunol* 4, 321; A. H. Lee, et al. (2005) *Embo J* 24, 4368). Secretion of immunoglobulin and zymogens from these cells is dramatically decreased in XBP-1 deficient mice, likely due to ER stress-induced apoptosis during development. XBP-1 is also required for embryonic liver development, although its function in the adult liver is unknown (A. M. Reimold et al. (2000) *Genes Dev* 14, 152).

The incidence of metabolic syndrome, a condition characterized by the constellation of central obesity, dyslipidemia, elevated blood glucose and hypertension, continues to rise in industrialized nations (G. A. Mensah et al. (2004) *Cardiol Clin* 22, 485). Dyslipidemia, manifested by elevated levels of plasma triglyceride (TG) and low density lipoprotein (LDL)-cholesterol and low levels of high density lipoprotein (HDL)-cholesterol is a risk factor for coronary artery disease (V. Bamba, D. J. Rader (2007) *Gastroenterology* 132, 2181; H. N. Ginsberg, Y. L. Zhang, A. Hernandez-Ono (2006) *Obesity* (Silver Spring) 14 Suppl 1, 41S). Increased de novo synthesis and secretion of lipids from the liver contributes significantly to the hepatic steatosis and dyslipidemia associated with type 2 diabetes (Bamba, D. J. Rader (2007) *Gastroenterology* 132, 2181; H. N. Ginsberg (2000) *J Clin Invest* 106, 453). Control of dyslipidemia with the statins, agents that target HMG CoA reductase, and with triglyceride lowering agents has resulted in measurable improvements in cardiovascular morbidity and mortality (J. D. Brunzell (2007) *N Engl J Med* 357, 1009). Hepatic lipid synthesis increases upon ingestion of excess carbohydrates, which are converted into TG, packaged into VLDL particles and transported to adipose tissue for energy storage (N. O. Davidson, G. S. Shelness (2000) *Annu Rev Nutr* 20, 169). Hepatic lipid metabolism is coordinated by multiple factors such as pancreatic hormones and serum glucose levels. In mammalian liver this transcriptional program is controlled by liver X receptor (LXR), sterol regulatory element-binding proteins (SREBPs) and ChREBP (S. W. Beaven, P. Tontonoz (2006) *Annu Rev Med* 57, 313; J. D. Horton, J. L. Goldstein, M. S. Brown (2002) *J Clin Invest* 109, 1125; K. Uyeda, J. J. Repa (2006) *Cell Metab* 4, 107; N. Mitro et al. (2007) *Nature* 445, 219) that directly or indirectly regulate the expression of critical enzymes involved in glycolytic and lipogenic pathways.

The further identification of molecular mechanisms involved in de novo lipogenesis would lead to identification of new drug targets and would provide methods of ameliorating dyslipidemia, steatosis, and steatohepatitis and, therefore, would be of great benefit.

SUMMARY OF THE INVENTION

The present invention demonstrates, inter alia, a role for the transcription factor XBP-1 in de novo lipogenesis. As described in the appended Examples, it has been discovered that the transcription factor XBP-1, best known as a key regulator of the Unfolded Protein Response (UPR), is required for de novo fatty acid synthesis in the liver, a function which is unrelated to its role in the UPR. XBP-1 protein expression is induced in the liver by a high carbohydrate diet and directly controls the induction of critical genes involved in fatty acid synthesis. Inducible, selective deletion of XBP-1 in liver results in marked hypocholesterolemia and hypotriglyceridemia secondary to a decreased production of lipids from the liver; this phenotype is not accompanied by hepatic steatosis or significant compromise in protein secretory function.

Accordingly, in one aspect, the invention pertains to methods of treating and/or preventing dyslipidemia comprising administering a nucleic acid molecule that downmodulates the activity of XBP-1 to a subject having dyslipidemia in an amount sufficient to downmodulate de novo hepatic lipogenesis, to thereby treat and/or prevent dyslipidemia in the subject.

In another aspect, the invention provides methods of treating and/or preventing atherosclerosis comprising administering a nucleic acid molecule that downmodulates the activity of XBP-1 to a subject having atherosclerosis in an amount sufficient to downmodulate de novo hepatic lipogenesis, to thereby treat and/or prevent atherosclerosis.

In another aspect, the invention provides methods of treating and/or preventing hepatic steatosis comprising administering a nucleic acid molecule that downmodulates the activity of XBP-1 to a subject having hepatic steatosis in an amount sufficient to downmodulate de novo hepatic lipogenesis, to thereby treat and/or prevent hepatic steatosis.

In one aspect, the invention provides methods treating and/or preventing steatohepatitis comprising administering a nucleic acid molecule that downmodulates the activity of XBP-1 to a subject having steatohepatitis in an amount sufficient to downmodulate de novo hepatic lipogenesis, to thereby treat and/or prevent steatohepatitis.

In another aspect, the invention provides methods of treating and/or preventing non-alcoholic hepatic steatohepatitis comprising administering a nucleic acid molecule that downmodulates the activity of XBP-1 to a subject having non-alcoholic hepatic steatohepafitis in an amount sufficient to downmodulate de novo hepatic lipogenesis, to thereby treat and/or prevent non-alcoholic hepatic steatohepatitis.

In yet another aspect, the invention provides methods of treating and/or preventing dyslipidemia comprising administering a nucleic acid molecule that downmodulates the activity of IRE-1 to a subject having dyslipidemia in an amount sufficient to downmodulate de novo hepatic lipogenesis, to thereby treat and/or prevent dyslipidemia.

In one aspect, the invention provides methods of treating and/or preventing atherosclerosis comprising administering a nucleic acid molecule that downmodulates the activity of IRE-1 to a subject having atherosclerosis in an amount sufficient to downmodulate de novo hepatic lipogenesis, to thereby treat and/or prevent atherosclerosis.

In another aspect, the invention provides methods of treating and/or preventing hepatic steatosis comprising administering a nucleic acid molecule that downmodulates the activity of IRE-1 to a subject having hepatic steatosis in an amount sufficient to downmodulate de novo hepatic lipogenesis, to thereby treat and/or prevent hepatic steatosis.

In another aspect, the invention provides methods of treating and/or preventing steatohepatitis comprising administering a nucleic acid molecule that downmodulates the activity of IRE-1 to a subject having steatohepatitis in an amount sufficient to downmodulate de novo hepatic lipogenesis, to thereby treat and/or prevent steatohepatitis.

In another aspect, the invention provides methods of treating and/or preventing non-alcoholic hepatic steatohepatitis comprising administering a nucleic acid molecule that downmodulates the activity of IRE-1 to a subject having non-alcoholic hepatic steatohepatitis in an amount sufficient to downmodulate de novo hepatic lipogenesis, to thereby treat and/or prevent non-alcoholic hepatic steatohepatitis.

In yet another aspect, the invention provides methods of treating and/or preventing dyslipidemia comprising administering an agent that upmodulates the activity of XBP-1 to a subject that would benefit from increased de novo hepatic lipogenesis in an amount sufficient to upmodulate de novo hepatic lipogenesis, to thereby treat and/or prevent dyslipidemia in the subject.

In another aspect, the invention provides methods of treating and/or preventing dyslipidemia comprising administering an agent that upmodulates the activity of IRE-1 to a subject a subject that would benefit from increased de novo hepatic lipogenesis in an amount sufficient to upmodulate de novo hepatic lipogenesis, to thereby treat and/or prevent dyslipidemia in the subject.

In one embodiment, the nucleic acid molecule is selected from the group consisting of: a nucleic acid molecule that is antisense to a XBP-1 molecule, a XBP-1 siRNA molecule, a nucleic acid molecule encoding a dominant negative XBP-1 molecule, or combinations thereof. In another embodiment, the nucleic acid molecule is a liposome:XBP-1 siRNA complex. In another embodiment, the nucleic acid molecule is a cholesterol:XBP-1 siRNA complex.

In one embodiment, the nucleic acid molecule is selected from the group consisting of: a nucleic acid molecule that is antisense to an IRE-1 molecule, a IRE-1 siRNA molecule, a nucleic acid molecule encoding a dominant negative IRE-1 molecule, or combinations thereof. In another embodiment, the nucleic acid molecule is a liposome: IRE-1 siRNA complex. In another embodiment, the nucleic acid molecule is a cholesterol: IRE-1 siRNA complex.

In one embodiment, the complex is administered at a dose of about 1-7.5 mg/kg.

In one embodiment, the methods further comprise administering to the subject a hypolipidemic agent. In one embodiment, the hypolipidemic agent is a statin.

In another aspect the invention provides methods of identifying a compound that is useful in treating and/or preventing dyslipidemia comprising, providing a cell comprising an XBP-1 polypeptide, contacting the cell with each member of a library of compounds, determining the effect of the compound on de novo hepatic lipogenesis; and selecting a compound of interest that downmodulates de novo hepatic lipogeneis as compared to an appropriate control, thereby identifying the compound as useful in treating and/or preventing dyslipidemia.

In another aspect the invention provides methods of identifying a compound that is useful in treating and/or preventing dyslipidemia comprising, providing a cell comprising an IRE-1 and an XBP-1 polypeptide, contacting the cell with each member of a library of compounds, determining the effect of the compound on de novo hepatic lipogenesis; and selecting a compound of interest that downmodulates de novo hepatic lipogeneis as compared to an appropriate control, thereby identifying the compound as useful in treating and/or preventing dyslipidemia.

In one embodiment, the effect of the compound on de novo hepatic lipogenesis is determined by determining the effect on the compound on the production of cholesterol and/or triglyceride. In one embodiment, the determination of the production of cholesterol is determined by determining the amount of at least one of: total cholesterol, LDL, IDL, VLDL, and HDL.

In one embodiment, determining the ability of the compound to modulate de novo hepatic lipogenesis comprises determining the expression of SREBP and/or chREBP.

In another embodiment, the ability of the compound to modulate de novo hepatic lipogenesis comprises determining the expression of a lipogenic gene. In one embodiment, the lipogenic gene is selected from the group consisting of: fasn, stearyl coA desaturase, diacyl glycerol acetyltransferase 2, acetyl coA carboxylase 2, and proprotein convertase subtilisin/kexin type 9 (PCSK9). In one embodiment, the expression of the lipogeneic gene is determined by a method selected from the group consisting of: microarray analysis, RT-PCR, and Northern blot analysis.

In one embodiment, the indicator cell for use in the methods of the invention further comprises a DNA molecule to which XBP-1 binds, wherein the DNA molecule comprises a promoter selected from the group consisting of a Dgat2 promoter, a Scd1 promoter, an Acc2 promoter; and a PCSK9 promoter; and the effect of the test compound on de novo hepatic lipogenesis is determined by evaluating the binding of XBP-1 to the DNA molecule in the presence and absence of the test compound. In one embodiment, the binding of XBP-1 to the promoter is determined by chromatin immunoprecipitation analysis.

In another embodiment, the indicator cell for use in the methods of the invention further comprises a reporter gene responsive to the XBP-1 polypeptide; and the effect of the test compound on de novo hepatic lipogenesis is determined by evaluating the expression of the reporter gene in the presence and absence of the test compound.

In one embodiment, the compound is present in a small molecule microarray.

In another embodiment, the indicator cell for use in the methods of the invention has been engineered to express the XBP-1 polypeptide by introducing into the cell an expression vector encoding the polypeptide.

In one embodiment, the cell is a hepatocyte. In one embodiment, the hepatocyte is an adult hepatocyte. In another embodiment; the cell is a HeLa cell. In another embodiment, the cell is a hepatoma cell.

Yet another aspect of the invention provides methods of identifying a compound that is useful in treating and/or preventing dyslipidemia comprising, providing a cell-free composition comprising an XBP-1 polypeptide and a DNA molecule to which XBP-1 binds, wherein the DNA molecule comprises the regulatory region of a lipogenic gene; contacting the polypeptide with each member of a library of compounds; selecting a compound that downmodulates the binding of the polypeptide to the DNA molecule as compared to an appropriate control, thereby identifying the compound as useful in treating and/or preventing dyslipidemia.

In another aspect, the invention provides methods of identifying a compound that is useful in treating and/or preventing dyslipidemia comprising, providing a cell comprising an XBP-1 polypeptide and a DNA molecule comprising a transcriptional regulatory site responsive to the DNA binding domain operatively linked a reporter gene, wherein the transcriptional regulatory site is selected from the group consisting of Dgat2 promoter, a Scd1 promoter, an Acc2 promoter; and a PCSK9 promoter; contacting the polypeptide with each member of a library of compounds; determining the effect of the compound on the level of expression of the reporter gene in the indicator cell in the presence and absence of the test compound; and selecting a compound of interest that downmodulates the level of expression of the reporter gene responsive to the XBP-1 protein as compared to an appropriate control, thereby identifying the compound as useful in treating and/or preventing dyslipidemia.

In one embodiment, the methods of the invention further comprise determining the effect of a test compound identified as useful in modulating dyslipidemia on the production of cholesterol and triglycerides in a non-human animal, comprising administering the test compound to the animal, measuring the production of cholesterol and triglycerides in the presence and absence of the test compound, and selecting a compound that modulates the production of cholesterol and/or triglycerides. In one embodiment, the production of cholesterol and triglycerides is determined by measuring the amount of at least one of: total cholesterol, LDL, VLDL, IDL, and HDL.

In another embodiment, the methods of the invention further comprise determining the effect of the identified compound on obesity and/or insulin resistance in a non-human animal. In one embodiment, the step of determining comprises providing the non-human animal with a high carbohydrate diet, administering the test compound to the non-human animal, determining the effect of the compound on at least one of body weight, serum triglycerides, total cholesterol, blood glucose, glucose tolerance, insulin tolerance, and glucose-stimulated insulin secretion in the presence and absence of the test compound, and selecting a compound that decreases obesity and/or insulin resistance in the non-human animal.

In another embodiment, the methods of the invention further comprise determining the effect of a identified compound on non-alcoholic hepatosteatosis in a non-human animal. In one embodiment, the step of determining comprises providing the non-human animal with a methionine and choline deficient diet, administering the test compound to the non-human animal, determining the effect of the compound on at least one of aspartate aminotransferase level, alanine aminotransferase level, liver cell inflammation, and presence of triglyceride vacuoles in a liver cell in the presence and absence of the test compound, and selecting a compound that decreases non-alcoholic hepatosteatosis in the non-human animal.

In another embodiment, the methods of the invention further comprise determining the effect of a identified compound on hypercholesterolemia and/or atherosclerosis in a non-human animal. In one embodiment, the step of determining comprises providing the non-human animal model with a high fat diet, administering the test compound to the non-human animal, determining the effect of the compound on at least one of serum triglycerides, total cholesterol, distribution of cholesterol among HDL, IDL, and LDL, and presence of atherosclerotic lesions, and selecting a compound that decreases hypercholesterolemia and/or atherosclerosis in the non-human animal.

In another aspect, the invention provides methods of identifying a compound that is useful in treating and/or preventing dyslipidemia comprising, providing an indicator composition comprising an XBP-1 polypeptide, contacting the indicator cell with each member of a library of test compounds, determining the activity of the XBP-1 polypeptide in the presence and absence of the test compound, selecting from the library of test compounds a compound of interest that downmodulates the activity of the XBP-1 polypeptide, determining the effect of the compound on de novo hepatic lipogeneis, selecting a compound of interest that downmodulates de novo hepatic lipogeneis as compared to an appropriate control, thereby identifying a compound that is useful in treating and/or preventing dyslipidemia.

In one embodiment, the effect of the compound on XBP-1 activity is determined by measuring the binding of XBP-1 to IRE-1. In another embodiment, the effect of the compound on XBP-1 activity is determined by assaying the activity of IRE-1. In one embodiment, the activity of IRE-1 is a kinase activity. In another embodiment, the activity of IRE-1 is an endoribonuclease activity. In one embodiment, the effect of the compound on XBP-1 activity is determined by assaying XBP-1 and/or IRE-1 protein levels.

In one embodiment, the XBP-1 polypeptide comprises a transactivation domain and the indicator composition further comprises a vector comprising a regulatory element responsive to the XBP-1 transactivation domain operatively linked to a reporter gene and the effect of the compound on the activity of the polypeptide is determined by evaluating the expression of the reporter gene in the presence and absence of the test compound.

In one embodiment, the indicator composition comprises a recombinant expression vector encoding a spliced XBP-1 protein; and a vector comprising a regulatory element responsive to the XBP-1 protein operatively linked a reporter gene and the effect of the compound on the activity of the polypeptide is determined by evaluating the expression of the reporter gene in the presence and absence of the test compound.

In one embodiment, the indicator composition is a cell and comprises, a recombinant expression vector comprising a regulatory element responsive to XBP-1 spliced protein operatively linked a reporter gene, wherein the cell is contacted with an agent that induces ER stress, and the effect of the compound on the activity of the polypeptide is determined by evaluating the expression of the reporter gene in the presence and absence of the test compound.

In one embodiment, the methods of the invention further comprise determining the effect of the identified compound on the ratio of unspliced XBP-1 to spliced XBP-1 mRNA and/or protein. In another embodiment, the methods of the invention further comprise determining the effect of the identified compound on the production of XBP-1 protein.

In one embodiment, the effect of the compound on de novo hepatic lipogeneis is determined by determining the effect on the compound on the production of cholesterol and/or triglyceride. In another embodiment, determining the ability of the compound to modulate de novo hepatic lipogenesis comprises determining the expression of SREBP and/or chREBP. In another embodiment, the ability of the compound to modulate de novo lipogenesis comprises determining the expression of a lipogenic gene.

In one embodiment, the indicator composition further comprises a DNA molecule to which XBP-1 binds, wherein the DNA molecule comprises a promoter selected from the group consisting of a Dgat2 promoter, a Scd1 promoter, an Acc2 promoter; and a PCSK9 promoter; and the effect of the test compound on de novo hepatic lipogenesis is determined by evaluating the binding of XBP-1 to the DNA molecule in the presence and absence of the test compound.

In one embodiment, the methods of the invention further comprise providing an indicator cell comprising a glucose-dependent promoter operably linked to a reporter gene and the effect of the compound on de novo hepatic lipogenesis is determined by evaluating the expression of the reporter gene in the presence and absence of the test compound.

In one embodiment, the methods of the invention further comprise determining the effect of the identified compound on obesity and/or insulin resistance in a non-human animal. In another embodiment, the methods of the invention further comprise determining the effect of a identified compound on non-alcoholic hepatosteatosis in a non-human animal. In another embodiment, the methods of the invention further comprise determining the effect of a identified compound on hypercholesterolemia and/or atherosclerosis in a non-human animal.

BRIEF DESCRIPTION OF THE FIGURES

FIG. 5A-5E depict that XBP-1 is activated by high fructose diet feeding, and directly induces lipogenic genes in the liver. (A) Wild type C57/BL6 mice were fed high fructose diet for 2 or 7 days and XBP-1s protein measured in the liver by Western blot. IRE-1 splicing of XBP-1 mRNA was measured by RT-PCR analysis. (B) WT and XBP-1Δ mice were fed standard rodent chow diet or high fructose diet for 7 days, and the expression of lipogenic genes in the liver determined. Values represent the abundance of each mRNA relative to WT mice fed chow diet. N=3-6. (C) Primary hepatocytes isolated from C57/BL6 mice were cultured in media containing the indicated concentrations of glucose and insulin for 24 h. Nuclear extracts were subjected to western blot analysis. (D) Primary hepatocytes isolated from WT or XBP-1Δ mice were infected with adenoviruses expressing XBP-1s or GFP control at 2 or 10 pfu per cell. Dgat2, Scd1, Acc2 and ERdj4 mRNA levels were measured 24 hours after the infection by real-time PCR. (E) CHIP assays were performed with liver nuclei of WT and XBP-1Δ mice, untreated or injected with tunicamycin 6 hrs prior to sacrifice. Values represent fold increases of real-time PCR signals compared to the signal for the untreated WT CHIP with control serum.

DETAILED DESCRIPTION

Figure 1A:
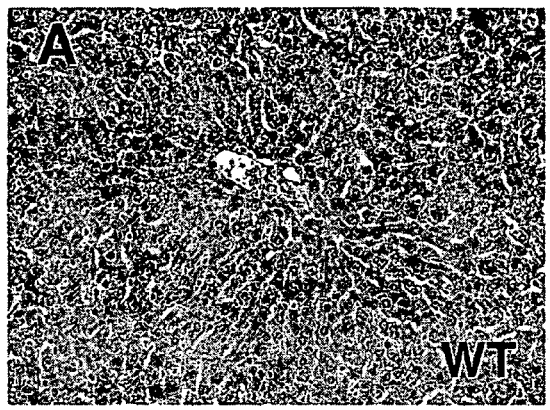
FIGS. 1A-1I depicts the ER stress response in XBP-1 deficient mouse liver. (A and B) Sections of paraffin-embedded livers of WT and XBP-1Δ mice were stained with hematoxylin and eosin. (C and D) Transmission electron micrographs of sections of WT and XBP-1Δ liver (E) Total RNAs were prepared from the liver of WT and XBP-1Δ mice 8 hours after tunicamycin injection at 1 mg/kg. Expression of representative UPR target genes was tested by quantitative real-time PCR analysis. Fold induction represents relative expression level±SEM compared to that of untreated WT mice. N=4 per group (F) Expression of the active XBP-1s and the processed ATF6a proteins was measured by Western blot of liver nuclear extracts. Sp1 expression is shown as a loading control. The levels of IRE-1 alpha-mediated XBP-1 mRNA (both WT and mutant) splicing were measured by RT-PCR analysis. *non-specific band (G) Western blot of total and phosphorylated JNK in WT and XBP-1Δ liver. (H) IRE-1 alpha was detected by immunoprecipitation followed by western blot by using IRE-1 alpha antibody. One third of the XBP-1Δ immunoprecipitation product was loaded on the last lane for a better comparison of band migration. Phosphorylated IRE-1 alpha displayed slowed migration on the gel. (I) IRE-1 alpha immunoprecipitation products were treated with λ phosphatase before loading on a 6% gel. Western blot analysis shows a band shift upon phosphatase treatment.
Figure 1B:
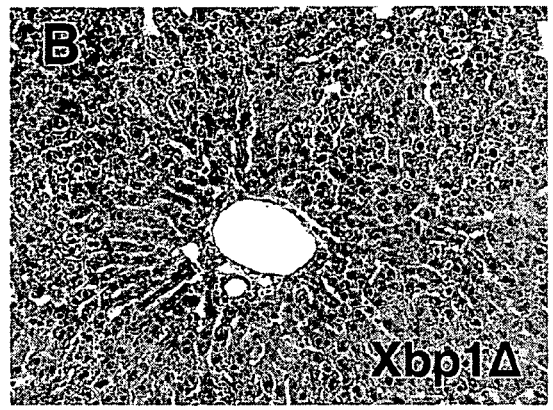

The instant invention is based, at least in part, on the discovery that XBP-1 plays a role in modulating de novo hepatic lipogenesis. In particular, it has been discovered that the transcription factor XBP-1, best known as a key regulator of the Unfolded Protein Response (UPR), is required for de novo fatty acid synthesis in the liver, a function which is unrelated to its role in the UPR since ablation of XBP-1 in the adult mouse does not activate the two other arms of the UPR, namely, ATF6 or PERK. Moreover, ablation of XBP-1 leads to constitutive activation of IRE-1 alpha, the upstream activator of XBP-1, demonstrating the presence of a feedback loop that precisely maintains spliced XBP-1 protein levels.

It has also been discovered that XBP-1 protein expression is induced in the liver by a high carbohydrate diet and directly controls the induction of critical genes involved in fatty acid synthesis. Inducible, selective deletion of XBP-1 in liver results in marked hypocholesterolemia and hypotriglyceridemia secondary to a decreased production of lipids from the liver; this phenotype is not accompanied by hepatic steatosis or significant compromise in protein secretory function. These findings provide for assays to identify agents that modulate the expression and/or activity of XBP-1 and/or IRE-1 which are useful in modulating de novo hepatic lipogenesis and provide for the use of such agents to treat and/or prevent dyslipidemia, hepatic steatosis, steatohepatistis and non-alcoholic steatohepatistis.

Certain terms are first defined so that the invention may be more readily understood.

I. Definitions

As used herein "de novo hepatic lipogenesis" refers to the process by which glucose is converted to fatty acids, which are subsequently esterified to glycerol to form the triacylglycerols that are packaged in VLDL and secreted from the liver. As used herein "de novo hepatic lipogenesis" encompasses the processes of fatty acid synthesis and subsequent triglyceride synthesis.

As used herein the term "dyslipidemia" refers to a disruption in the amount of lipids, e.g., cholesterols (e.g., total cholesterol, very low density lipoprotein (VLDL), intermediate density lipoprotein (IDL), low density liporprotein (LDL), high density liporprotein (HDL)), triglycerides, in the blood. In one embodiment, dyslipidemia is hyperlipidemia, i.e., elevated levels of lipids (cholesterol and/or triglycerides) in the blood, e.g., total cholesterol (TC)>200 mg/dL (>5.17 mmol/L), LDL>100 mg/dL (>3.36 mmol/L), HDL>60 mg/dL (>1.55 mmol/L), VLDL>50 mg/dL, triglycerides (TG)>150 mg/dL (>1.695 mmol/L). In another embodiment, dyslipidemia is hypolipidemia, i.e., decreased levels of lipids in the blood, e.g., total cholesterol (TC)<120 mg/dL (<3.1 mmol/L) or LDL<50 mg/dL (<0.13 mmol/L), HDL<40 mg/dL (>1.03 mmol/L), VLDL>8 mg/dL, triglycerides (TG) <80 mg/dL. A subject with dyslipidemia may be identified by, for example, measuring serum lipid levels, e.g., fasting serum lipid levels, using methods routine to one of skill in the art. In one embodiment, non-HDL cholesterol is measured, e.g., the amount of total cholesterol minus the amount of HDL cholesterol.

In general lipoprotein particles range in size from 10 to 1000 nm. They are composed of a hydrophobic core containing cholesteryl esters, triglycerides, fatty acids and fat-soluble vitamins. The surrounding hydrophilic layer is composed of various apolipoproteins, phospholipids and cholesterol.

"Chylomicrons" are the largest (1000 nm) and least dense (<0.95) of the lipoproteins. They contain only 1-2% protein, 85-88% triglycerides, ~8% phospholipids, ~3% cholesteryl esters and ~1% cholesterol. Chylomicrons contain several types of apolipoproteins including apo-AI, II & IV, apo-B48, apo-CI, II & III, apo-E and apo-H.

Chylomicrons are produced for the purpose of transporting dietary triglycerides and cholesterol absorbed by intestinal epithelia. Chylomicron assembly originates in the intestinal mucosa. Excretion into the plasma is facilitated through the lymphatic system. In the plasma, chylomicrons acquire apo-CII and apo-E from HDL. Once transported to tissues, triglycerides contained in chylomicrons are hydrolyzed by apo-CII-dependent activation of lipoprotein lipase contained on the endothelial cell walls. The chylomicron remnant, including residual cholesterol, is taken up by the liver via receptor-mediated endocytosis by recognition of it's apo-E component.

"Very low density lipoproteins" are approximately 25-90 nm in size (MW 6-27 million), with a density of ~0.98. They contain 5-12% protein, 50-55% triglycerides, 18-20% phospholipids, 12-15% cholesteryl esters and 8-10% cholesterol. VLDL also contains several types of apolipoproteins including apo-B100, apo-CI, II & III and apo-E. VLDL also obtains apo-CII and apo-E from plasma HDL. VLDL assembly in the liver involves the early association of lipids with apo-B100 mediated by microsomal triglyceride transfer protein while apo-B100 is translocated to the lumen of the ER. Lipoprotein lipase also removes triglycerides from VLDL in the same way as from chylomicrons.

"Intermediate density lipoproteins" are smaller than VLDL (40 nm) and more dense (~1.0). They contain the same apolipoproteins as VLDL. They are composed of 10-12% protein, 24-30% triglycerides, 25-27% phospholipids, 32-35% cholesteryl esters and 8-10% cholesterol. LDLs are derived from triglyceride depletion of VLDL. LDLs can be taken up by the liver for reprocessing, or upon further triglyceride depletion, become LDL.

"Low density lipoproteins" are smaller than IDL (26 nm) (MW approximately 3.5 million) and more dense (~1.04). They contain the apolipoprotein apo-B100. LDL contains 20-22% protein, 10-15% triglycerides, 20-28% phospholipids, 37-48% cholesteryl esters and 8-10% cholesterol.

LDL and HDL transport both dietary and endogenous cholesterol in the plasma. LDL is the main transporter of cholesterol and cholesteryl esters and makes up more than half of the total lipoprotein in plasma. LDL is absorbed by the liver and other tissues via receptor mediated endocytosis. The cytoplasmic domain of the LDL receptor facilitates the formation of coated pits; receptor-rich regions of the membrane. The ligand binding domain of the receptor recognizes apo-B100 on LDL, resulting in the formation of a clathrin-coated vesicle. ATP-dependent proton pumps lower the pH inside the vesicle resulting dissociation of LDL from its receptor. After loss of the clathrin coat the vesicles fuse with lysozomes, resulting in peptide and cholesteryl ester enzymatic hydrolysis. The LDL receptor can be recycled to the cell membrane. Insulin, tri-iodothyronine and dexamethasome have shown to be involved with the regulation of LDL receptor mediated uptake.

"Lipoprotein(a)" is similar in structure to LDL. However, it contains a additional protein, apolipoprotein(a) (apo-(a)), covalently bound to apo-B. Apo-(a) has been found to have a high sequence homology with plasminogen. It contains variable amounts of repeating kringle regions and more than 40 isoforms with a MW range of 400-700 kD. Its function is thought to be related to triglyceride metabolism and possibly thrombotic and atherogenic pathways.

"High density lipoproteins" are the smallest of the lipoproteins (6-12.5 nm) (MW 175-500 KD) and most dense (~1.12). HDL contains several types of apolipoproteins including apo-AI, II & IV, apo-CI, II & III, apo-D and apo-E. HDL contains approximately 55% protein, 3-15% triglycerides, 26-46% phospholipids, 15-30% cholesteryl esters and 2-10% cholesterol.

HDL is produced as a protein rich particle in the liver and intestine, and serves as a circulating source of Apo-CI & II and Apo-E proteins. The HDL protein particle accumulates cholesteryl esters by the esterification of cholesterol by lecithin-cholesterol acyl-transferase (LCAT). LCAT is activated by apo-AI on HDL. HDL can acquire cholesterol from cell membranes and can transfer cholesteryl esters to VLDL and LDL via transferase activity in apo-D. HDL can return to the liver where cholesterol is removed by reverse cholesterol transport, thus serving as a scavenger to free cholesterol. The liver can then excrete excess cholesterol in the form of bile acids.

As used herein, "atherosclerosis" is a disease affecting arterial blood vessels. It is a chronic inflammatory response in the walls of arteries, in large part due to the accumulation of macrophage white blood cells and promoted by low density (especially small particle) lipoproteins (plasma proteins that carry cholesterol and triglycerides) without adequate removal of fats and cholesterol from the macrophages by functional high density lipoproteins (HDL). It is commonly referred to as a "hardening" or "furring" of the arteries. It is caused by the formation of multiple plaques within the arteries.

A subject with atherosclerosis may be identified by, for example, angiography, stress-testing, coronary calcium scoring by CT, carotid IMT (intimal media thickness) measurement by ultrasound, Intravascular ultrasound (IVUS), lipoprotein subclass analysis, Glycosylated (or glycated) hemoglobin (HbA1c), C-reactive protein (CRP), homocysteine, anatomic (abdominal girth) and physiologic (blood pressure, elevated blood glucose) methods.

As used herein, "hypercholesterolemia" is the presence of high levels of cholesterol in the blood that can contribute to many forms of disease, e.g. cardiovascular disease.

A subject with hypercholesterolemia may be identified by, for example, serum analysis of non-fasting cholesterol and/or serum analysis of fasting cholesterol levels. A subject with a total cholesterol more than 200 mg/dL or HDL less than 40 mg/dL) (non-fasting) and/or fasting cholesterol levels between 140 and 240 mg/dL is identified as having hypercholesteremia.

As used herein, "obesity" is a condition in which excess body fat has accumulated to such an extent that health may be negatively affected. It is commonly defined as a body mass index (BMI) of 30 kg/m2 or higher which distinguishes it from being overweight as defined by a BMI of 25 kg/m2 or higher (see, e.g., World Health Organization (2000) (PDF). Technical report series 894: Obesity: Preventing and managing the global epidemic. Geneva: World Health Organization). Excessive body weight is associated with various diseases, particularly cardiovascular diseases, diabetes mellitus type 2, obstructive sleep apnea, certain types of cancer, and osteoarthritis.

A subject with obesity may be identified by, for example, by determining BMI (BMI is calculated by dividing the subject's mass by the square of his or her height), waist circumference and waist-hip ratio (the absolute waist circumference (>102 cm in men and >88 cm in women) and the waist-hip ratio (the circumference of the waist divided by that of the hips of >0.9 for men and >0.85 for women) (see, e.g., Yusuf S, et al., (2004). Lancet 364: 937-52), and/or body fat percentage (total body fat expressed as a percentage of total body weight men with more than 25% body fat and women with more than 33% body fat are obese; body fat percentage can be estimated from a person's BMI by the following formula: Bodyfat %=(1.2*BMI)+(0.23*age)−5.4−(10.8*gender), where gender is 0 if female and 1 if male). Body fat percentage measurement techniques include, for example, computed tomography (CT scan), magnetic resonance imaging (MRI), and dual energy X-ray absorptiometry (DEXA).

As used herein, "insulin resistance" is the condition in which normal amounts of insulin are inadequate to produce a normal insulin response from fat, muscle and liver cells. Insulin resistance in fat cells reduces the effects of insulin and results in elevated hydrolysis of stored triglycerides in the absence of measures which either increase insulin sensitivity or which provide additional insulin. Increased mobilization of stored lipids in these cells elevates free fatty acids in the blood plasma. Insulin resistance in muscle cells reduces glucose uptake (and so local storage of glucose as glycogen), whereas insulin resistance in liver cells results in impaired glycogen synthesis and a failure to suppress glucose production. Elevated blood fatty acid levels (associated with insulin resistance and diabetes mellitus Type 2), reduced muscle glucose uptake, and increased liver glucose production all contribute to elevated blood glucose levels. High plasma levels of insulin and glucose due to insulin resistance are believed to be the origin of metabolic syndrome and type 2 diabetes.

A subject with insulin resistance may be identified by, for example, determining fasting Insulin Levels, Glucose tolerance testing, Modified Insulin Suppression Testing, Hyperinsulinemic euglycemic clamping, Homeostatic Model Assessment (HOMA), the QUICKI (quantitative insulin sensitivity check index).

A fasting serum insulin level of greater than the upper limit of normal for the assay used (approximately 60 pmol/L) is considered evidence of insulin resistance.

During a glucose tolerance test, which may be used to diagnose diabetes mellitus, a fasted patient takes a 75 gram oral dose of glucose. Blood glucose levels are then measured over the following 2 hours. Interpretation is based on WHO guidelines. After 2 hours a Glycemia less than 7.8 mmol/L is considered normal, a glycaemia of between 7.8 to 11.0 is considered as Impaired Glucose Tolerance (IGT) and a glycaemia of greater than or equal to 11.1 is considered Diabetes Mellitus.

An oral GTT can be normal or mildly abnormal in simple insulin resistance. Often, there are raised glucose levels in the early measurements, reflecting the loss of a postprandial (after the meal) peak in insulin production. Extension of the testing (for several more hours) may reveal a hypoglycemic "dip," which is a result of an overshoot in insulin production after the failure of the physiologic postprandial insulin response.

The gold standard for investigating and quantifying insulin resistance is the "hyperinsulinemic euglycemic clamp," so-called because it measures the amount of glucose necessary to compensate for an increased insulin level without causing hypoglycemia. The rate of glucose infusion is commonly referred to in diabetes literature as the GINF value.

The test is performed by infusing insulin through a peripheral vein, at 10-120 mU per m2 per minute. In order to compensate for the insulin infusion, glucose 20% is infused to maintain blood sugar levels between 5 and 5.5 mmol/l. The rate of glucose infusion is determined by checking the blood sugar levels every 5 to 10 minutes. Low-dose insulin infusions are more useful for assessing the response of the liver, whereas high-dose insulin infusions are useful for assessing peripheral (i.e., muscle and fat) insulin action.

The rate of glucose infusion during the last 30 minutes of the test determines insulin sensitivity. If high levels (7.5 mg/min or higher) are required, the patient is insulin-sensitive. Very low levels (4.0 mg/min or lower) indicate that the body is resistant to insulin action. Levels between 4.0 and 7.5 mg/min are not definitive and suggest "impaired glucose tolerance," an early sign of insulin resistance.

This basic technique can be significantly enhanced by the use of glucose tracers. Glucose can be labeled with either stable or radioactive atoms.

Another measure of insulin resistance is the modified insulin suppression test developed by Gerald Reaven at Stanford University. Patients initially receive 25 mcg of octreotide (Sandostatin) in 5 ml of normal saline over 3 to 5 min IV as an initial bolus, and then will be infused continuously with an intravenous infusion of somatostatin (0.27 μgm/m2/min) to suppress endogenous insulin and glucose secretion. Insulin and 20% glucose is then infused at rates of 32 and 267 mg/m2/min, respectively. Blood glucose is checked at zero, 30, 60, 90, and 120 minutes, and then every 10 minutes for the last half-hour of the test. These last 4 values are averaged to determine the steady-state plasma glucose level. Subjects with an SSPG greater than 150 mg/dl are considered to be insulin-resistant.

As used herein, "hepatic steatosis" also known as "steatorrhoeic hepatosis" or "fatty liver disease" (FLD) is the presence of large vacuoles of triglyceride fat accumulation in liver cells. The development of hepatic steatosis is associated with, for example, obesity (with or without effects of insulin resistance), diabetes, metabolic syndrome, hypertension, atherosclerosis, dyslipidemia associated with protease inhibitor treatment of HIV, dyslipidemia associated with antipsychotic treatment of schizophrenia, and chronic kidney disease. Hepatic steatosis may also develop with excessive alcohol intake.

As used herein "steatohepatitis" is the presence of large vacuoles of triglyceride fat accumulation in liver cells with concurrent inflammation of the liver due to excessive alcohol consumption.

As used herein, "non-alcoholic steatohepatitis" (or "NASH") (i.e., steatohepatitis not associated with excessive alcohol consumption) is the presence of large vacuoles of triglyceride fat accumulation in liver cells with concurrent inflammation of the liver associated with, for example, obesity (with or without effects of insulin resistance), metabolic syndrome, diabetes, hypertension, atherosclerosis, dyslipidemia associated with protease inhibitor treatment of HIV, dyslipidemia associated with antipsychotic treatment of schizophrenia, and chronic kidney disease.

Both steatohepatitis and non-alcoholic steatohepatitis may progress to cirrhosis.

A subject with hepatic steatosis, steatohepatitis or non-alcoholic steatohepatitis may be identified by, for example, liver function tests, e.g., measurement of serum levels of, for example, albumin, various liver enzymes (ALT, AST, GGT and ALP), bilirubin, prothrombin time, cholesterol, total protein serum, etc., imaging, i.e., ultrasonography, CT scan, MRI, and/or biopsy showing hepatic fat accumulation (steatosis), mixed lobular inflammation, ballooning degeneration of hepatocytes (sometimes with identifiable Mallory bodies), glycogenated hepatocyte nuclei, and pericellular fibrosis. A "chicken wire" pattern of the pericellular fibrosis, which affects portal areas only secondarily in later stages, is very characteristic and is identified on trichrome stains. Such determinations are routine to the skilled artisan.

As used herein, the term "XBP-1" refers to the X-box binding protein. XBP-1 is a basic region leucine zipper (b-zip) transcription factor isolated independently by its ability to bind to a cyclic AMP response element (CRE)-like sequence in the mouse class II MHC Aα gene or the CRE-like site in the HTLV-1 21 base pair enhancer, and subsequently shown to regulate transcription of both the DRα and HTLV-1 ltr gene.

Like other members of the b-zip family, XBP-1 has a basic region that mediates DNA-binding and an adjacent leucine zipper structure that mediates protein dimerization. Deletional and mutational analysis has identified transactivation domains in the C-terminus of XBP-1 in regions rich in acidic residues, glutamine, serine/threonine and proline/glutamine.

XBP-1 is present at high levels in plasma cells in joint synovium in patients with rheumatoid arthritis. In human multiple myeloma cells, XBP-1 is selectively induced by IL-6 treatment and implicated in the proliferation of malignant plasma cells. XBP-1 has also been shown to be a key factor in the transcriptional regulation of molecular chaperones and to enhance the compensatory UPR (Calfon et al., Nature 415, 92 (2002); Shen et al., Cell 107:893 (2001); Yoshida et al., Cell 107:881 (2001); Lee et al., Mol. Cell. Biol. 23:7448 (2003); each of which is incorporated herein by reference).

The amino acid sequence of XBP-1 is described in, for example, Liou, H-C. et. al. (1990) Science 247:1581-1584 and Yoshimura, T. et al. (1990) EMBO J. 9:2537-2542. The amino acid sequence of mammalian homologs of XBP-1 are described in, for example, in Kishimoto T. et al., (1996) Biochem. Biophys. Res. Commun. 223:746-751 (rat homologue). Exemplary proteins intended to be encompassed by the term "XBP-1" include those having amino acid sequences disclosed in GenBank with accession numbers A36299 [gi: 105867]; AF443192 [gi: 18139942] (spliced murine XBP-1); P17861 [gi:139787]; CAA39149 [gi:287645]; AF027963 [gi: 13752783] (murine unspliced XBP-1); BAB82982.1 [gi: 18148382] (spliced human XBP-1); BAB82981 [gi: 18148380] (human unspliced XBP-1); and BAA82600 [gi: 5596360] or e.g., encoded by nucleic acid molecules such as those disclosed in GenBank with accession numbers AF027963 [gi: 13752783]; NM_013842 [gi:13775155] (spliced murine XBP-1); or M31627 [gi:184485] (unspliced murine XBP-1); AB076384 [gi:18148381] (spliced human XBP-1); or AB076383 [gi:18148379] (human unspliced XBP-1). XBP-1 is also referred to in the art as TREB5 or HTF (Yoshimura et al. 1990. EMBO Journal. 9:2537; Matsuzaki et al. 1995. J. Biochem. 117:303).

There are two forms of XBP-1 protein, unspliced and spliced, which differ markedly in their sequence and activity. Unless the form is referred to explicitly herein, the term "XBP-1" as used herein includes both the spliced and unspliced forms.

As used herein, the term "spliced XBP-1" or "XBP-1s" refers to the spliced, processed form of the mammalian XBP-1 mRNA or the corresponding protein. Human and murine XBP-1 mRNA contain an open reading frame (ORF1) encoding bZIP proteins of 261 and 267 amino acids, respectively. Both mRNA's also contain another ORF, ORF2, partially overlapping but not in frame with ORF1. ORF2 encodes 222 amino acids in both human and murine cells. Human and murine ORF1 and ORF2 in the XBP-1 mRNA share 75% and 89% identity respectively. In response to ER stress, XBP-1 mRNA is processed by the ER transmembrane endoribonuclease and kinase IRE-1 which excises an intron from XBP-1 mRNA. In murine and human cells, a 26 nucleotide intron is excised. The boundaries of the excised introns are encompassed in an RNA structure that includes two loops of seven residues held in place by short stems. The RNA sequences 5' to 3' to the boundaries of the excised introns form extensive base-pair interactions. Splicing out of 26 nucleotides in murine and human cells results in a frame shift at amino acid 165 (the numbering of XBP-1 amino acids herein is based on GenBank accession number NM_013842 [gi:13775155] (spliced murine XBP-1) and one of ordinary skill in the art can determine corresponding amino acid numbers for XBP-1 from other organisms, e.g., by performing a simple alignment). This causes removal of the C-terminal 97 amino acids from the first open reading frame (ORF1) and addition of the 212 amino from ORF2 to the N-terminal 164 amino acids of ORF1 containing the b-ZIP domain. In mammalian cells, this splicing event results in the conversion of a 267 amino acid unspliced XBP-1 protein to a 371 amino acid spliced XBP-1 protein. The spliced XBP-1 then translocates into the nucleus where it binds to its target sequences to induce their transcription.

As used herein, the term "unspliced XBP-1" refers to the unprocessed XBP-1 mRNA or the corresponding protein. As set forth above, unspliced murine XBP-1 is 267 amino acids in length and spliced murine XBP-1 is 371 amino acids in length. The sequence of unspliced XBP-1 is known in the art and can be found, e.g., Liou, H-C. et. al. (1990) Science 247:1581-1584 and Yoshimura, T. et al. (1990) EMBO J. 9:2537-2542, or at GenBank accession numbers: AF443192 [gi: 18139942] (amino acid spliced murine XBP-1); AF027963 [gi: 13752783] (amino acid murine unspliced XBP-1); NM_013842 [gi:13775155] (nucleic acid spliced murine XBP-1); or M31627 [gi:184485] (nucleic acid unspliced murine XBP-1.

As used herein, the term "ratio of spliced to unspliced XBP-1" refers to the amount of spliced XBP-1 present in a cell or a cell-free system, relative to the amount or of unspliced XBP-1 present in the cell or cell-free system. "The ratio of unspliced to spliced XBP-1" refers to the amount of unspliced XBP-1 compared to the amount of unspliced XBP-1. "Increasing the ratio of spliced XBP-1 to unspliced XBP-1" encompasses increasing the amount of spliced XBP-1 or decreasing the amount of unspliced XBP-1 by, for example, promoting the degradation of unspliced XBP-1. Increasing the ratio of unspliced XBP-1 to spliced XBP-1 can be accomplished, e.g., by decreasing the amount of spliced XBP-1 or by increasing the amount of unspliced XBP-1. Levels of spliced and unspliced XBP-1 an be determined as described herein, e.g., by comparing amounts of each of the proteins which can be distinguished on the basis of their molecular weights or on the basis of their ability to be recognized by an antibody. In another embodiment described in more detail below, PCR can be performed employing primers with span the splice junction to identify unspliced XBP-1 and spliced XBP-1 and the ratio of these levels can be readily calculated.

As used herein, the term "Unfolded Protein Response" (UPR) or the "Unfolded Protein Response pathway" refers to an adaptive response to the accumulation of unfolded proteins in the ER and includes the transcriptional activation of genes encoding chaperones and folding catalysts and protein degrading complexes as well as translational attenuation to limit further accumulation of unfolded proteins. Both surface and secreted proteins are synthesized in the endoplasmic reticulum (ER) where they need to fold and assemble prior to being transported.

Since the ER and the nucleus are located in separate compartments of the cell, the unfolded protein signal must be sensed in the lumen of the ER and transferred across the ER membrane and be received by the transcription machinery in the nucleus. The unfolded protein response (UPR) performs this function for the cell. Activation of the UPR can be caused by treatment of cells with reducing agents like DTT, by inhibitors of core glycosylation like tunicamycin or by Ca-ionophores that deplete the ER calcium stores. First discovered in yeast, the UPR has now been described in C. elegans as well as in mammalian cells. In mammals, the UPR signal cascade is mediated by three types of ER transmembrane proteins: the protein-kinase and site-specific endoribonuclease IRE-1; the eukaryotic translation initiation factor 2 kinase, PERK/PEK; and the transcriptional activator ATF6. If the UPR cannot adapt to the presence of unfolded proteins in the ER, an apoptotic response is initiated leading to the activation of JNK protein kinase and caspases 7, 12, and 3. The most proximal signal from the lumen of the ER is received by a transmembrane endoribonuclease and kinase called IRE-1. Following ER stress, IRE-1 is essential for survival because it initiates splicing of the XBP-1 mRNA the spliced version of which, as shown herein, activates the UPR.

Eukaryotic cells respond to the presence of unfolded proteins by upregulating the transcription of genes encoding ER resident protein chaperones such as the glucose-regulated BiP/Grp74, GrP94 and CHOP genes, folding catalysts and protein degrading complexes that assist in protein folding.

As used herein, the term "modulation of the UPR" includes both upregulation and downregulation of the UPR. As used herein the term "UPRE" refers to UPR elements upstream of certain genes which are involved in the activation of these genes in response, e.g., to signals sent upon the accumulation of unfolded proteins in the lumen of the endoplasmic reticulum, e.g., EDEM, Herp, e.g., ER stress-responsive cis-acting elements with the consensus sequence TGACGTGG/A (SEQ ID NO:25) (Wang, Y., et al. 2000. J. Biol. Chem. 275:27013-27020; Yoshida, H., et al. 2001. Cell 107:881-891). Such elements are suitable for use in the screening assays of the invention.

As used herein, the term "ER stress" includes conditions such as the presence of reducing agents, depletion of ER lumenal Ca2+, inhibition of glycosylation or interference with the secretory pathway (by preventing transfer to the Golgi system), which lead to an accumulation of misfolded protein intermediates and increase the demand on the chaperoning capacity, and induce ER-specific stress response pathways. ER stress pathways involved with protein processing include the Unfolded Protein Response (UPR) and the Endoplasmic Reticulum Overload Response (EOR) which is triggered by certain of the same conditions known to activate UPR (e.g. glucose deprivation, glycosylation inhibition), as well as by heavy overexpression of proteins within the ER. The distinguishing feature of EOR is its association with the activation of the transcription factor NF-κB. Modulation of both the UPR and the EOR can be accomplished using the methods and compositions of the invention. ER stress can be induced, for example, by inhibiting the ER Ca2+ ATPase, e.g., with thapsigargin. As used herein, the term "protein folding or transport" encompasses posttranslational processes including folding, glycosylation, subunit assembly and transfer to the Golgi compartment of nascent polypeptide chains entering the secretory pathway, as well as extracytosolic portions of proteins destined for the external or internal cell membranes, that take place in the ER lumen. Proteins in the ER are destined to be secreted or expressed on the surface of a cell. Accordingly, expression of a protein on the cell surface or secretion of a protein can be used as indicators of protein folding or transport.

As referred to herein, the term "proteasome pathway" refers to a pathway by which a variety of cellular proteins are degraded and is also called the ubiquitin-proteasome pathway. Many proteins are marked for degradation in this pathway by covalent attachment of ubiquitin. For example, as shown in the Examples herein, the XBP-1 unspliced protein is an example of a ubiquitinated, and hence extremely unstable, protein. XBP-1 spliced protein is not ubiquitinated, and has a much longer half life than unspliced XBP-1 protein.

As used herein, the term "IRE-1" refers to an ER transmembrane endoribonuclease and kinase called "iron responsive element binding protein-1," which oligomerizes and is activated by autophosphorylation upon sensing the presence of unfolded proteins, see, e.g., Shamu et al., (1996) EMBO J. 15: 3028-3039. In *Saccharomyces cerevisiae*, the UPR is controlled by IREp. In the mammalian genome, there are two homologs of IRE-1, IRE1a and IRE1β. IRE1a is expressed in all cells and tissue whereas IRE1β is primarily expressed in intestinal tissue. The endoribonucleases of either IRE1a and IRE1β are sufficient to activate the UPR. Accordingly, as used herein, the term "IRE-1" includes, e.g., IRE1a, IRE1β and IREp. In a preferred embodiment, IRE-1 refers to IRE1a.

IRE-1 is a large protein having a transmembrane segment anchoring the protein to the ER membrane. A segment of the IRE-1 protein has homology to protein kinases and the C-terminal has some homology to RNAses. Over-expression of the IRE-1 gene leads to constitutive activation of the UPR. Phosphorylation of the IRE-1 protein occurs at specific serine or threonine residues in the protein.

IRE-1 senses the overabundance of unfolded proteins in the lumen of the ER. The oligomerization of this kinase leads to the activation of a C-terminal endoribonuclease by trans-autophosphorylation of its cytoplasmic domains. IRE-1 uses its endoribonuclease activity to excise an intron from XBP-1 mRNA. Cleavage and removal of a small intron is followed by re-ligation of the 5' and 3' fragments to produce a processed mRNA that is translated more efficiently and encodes a more stable protein (Calfon et al. (2002) Nature 415(3): 92-95). The nucleotide specificity of the cleavage reaction for splicing XBP-1 is well documented and closely resembles that for IRE-p mediated cleavage of HAC1 mRNA (Yoshida et al. (2001) Cell 107:881-891). In particular, IRE-1 mediated cleavage of murine XBP-1 cDNA occurs at nucleotides 506 and 532 and results in the excision of a 26 base pair fragment (e.g., CAGCACTCAGACTACGTGCACCTCTG (SEQ ID NO:1) for mouse XBP-1). IRE-1 mediated cleavage of XBP-1 derived from other species, including humans, occurs at nucleotides corresponding to nucleotides 506 and 532 of murine XBP-1 cDNA, for example, between nucleotides 502 and 503 and 528 and 529 of human XBP-1.

There are two transcript variants of IRE-1, the sequence of which are known in the art and can be found at, e.g., at GenBank accession numbers: gi:50345998 and gi:153946420.

XBP-1 controls expression of several other genes, for example, ERdj4, p58ipk, EDEM, PDI-P5, RAMP4, HEDJ, BiP, ATF6a, XBP-1, Armet and DNAJB9, which encodes the 222 amino acid protein, mDj7 (GenBank Accession Number NM—013760 [gi:31560494]). These genes are important in a variety of cellular functions. For example, Hsp70 family proteins including BiP/Grp78 which is a representative ER localizing HSP70 member, function in protein folding in mammalian cells. A family of mammalian DnaJ/Hsp40-like proteins has recently been identified that are presumed to carry out the accessory folding functions. Two of them, Erdj4 and p58ipk, were shown to be induced by ER stress, localize to the ER, and modulate HSP70 activity (Chevalier et al. 2000 J Biol Chem 275: 19620-19627; Ohtsuka and Hata 2000 Cell Stress Chaperones 5: 98-112; Yan et al. 2002 Proc Natl Acad Sci USA 99: 15920-15925). ERdj4 has recently been shown to stimulate the ATPase activity of BiP, and to suppress ER stress-induced cell death (Kurisu et al. 2003 Genes Cells 8: 189-202; Shen et al. 2003 J Biol Chem 277: 15947-15956). ERdj4, p58IPK, EDEM, RAMP-4, PDI-P5 and HEDJ, all appear to act in the ER. ERdj4 (Shen et al. 2003), p58IPK (Melville et al. 1999 J Biol Chem 274: 3797-3803) and HEDJ (Yu et al. 2000 Mol Cell 6: 1355-1364) are localized to the ER and display Hsp40-like ATPase augmenting activity for the HspTO family chaperone proteins. EDEM was shown to be critically involved in the ERAD pathway by facilitating the degradation of ERAD substrates (Hosokawa et al. 2001 EMBO Rep 2:415-422; Molinari et al. 2003 Science 299 1397-1400; Oda et al. 2003 Science 299:1394-1397; Yoshida et al. 2003 Dev. Cell. 4:265-271). RAMP4 is a recently identified protein implicated in glycosylation and stabilization of membrane proteins in response to stress (Schroder et al. 1999 EMBO J. 18:4804-4815; Wang and Dobberstein 1999 Febs Lett 457:316-322; Yamaguchi et al. 1999 J. Cell Biol 147: 1195-1204). PD1-P5 has homology to protein disulfide isomerase, which is thought to be involved in disulfide bond formation (Kikuchi et al. 2002 J. Biochem (Tokyo) 132:451-455). Collectively, these results show that the IRE1/XBP-1 pathway is required for efficient protein folding, maturation and degradation in the ER.

Another UPR signaling pathway is activated by the PERK protein kinase. PERK phosphorylates eIF2a, which induces a transient suppression of protein translation accompanied by induction of transcription factor(s) such as ATF4 (Harding et al. 2000 Mol Cell 6: 1099-1108). eIF2a is also phosphorylated under various cellular stress conditions by specific kinases, double strand RNA activated protein kinase PKR, the amino acid control kinase GCN2 and the heme regulated inhibitor HRI (Samuel 1993 J. Biol. Chem. 268:7603-76-6; Kaufman 1999 Genes Dev. 13: 1211-1233). Since genes that are induced by the PERK pathway are also induced by other stress signals, such as amino acid deprivation, it is likely that PERK dependent UPR target genes carry out common cellular defense mechanisms, such as cellular homeostasis, apoptosis and cell cycle (Harding et al. 2003 Mol. Cell. 11619-633). Collectively, ER stress activates IRE/XBP-1 and PERK/eIF2a pathways to ensure proper maturation and degradation of secretory proteins and to effect common cellular defense mechanisms, respectively.

The reliance of p58IPK gene expression on XBP-1 connects two of the UPR signaling pathways, IRE1/XBP-1 and PERK. P58IPK was originally identified as a 58 kD inhibitor of PKR in influenza virus-infected kidney cells (Lee et al. 1990 Proc Natl Acad Sci USA 87: 6208-6212) and described to downregulate the activity of PKR by binding to its kinase domain (Katze 1995 Trends Microbiol 3: 75-78). It also has a J domain in the C-terminus which has been shown to participate in interactions with Hsp70 family proteins Melville et al. 1999 J Biol Chem 274: 3797-380). Recently Katze and colleagues have demonstrated that p58IPK interacts with ERK which is structurally similar to PKR, inhibits its eIF2a kinase activity and that it is induced during the UPR by virtue of an ER stress-response element in its promoter region (Yan et al. 2002 Proc Natl Acad Sci USA 99: 15920-15925).

As used herein the term "activating transcription factors 6" include ATF6α and ATF6β. ATF6 is a member of the basic-leucine zipper family of transcription factors. It contains a transmembrane domain and is located in membranes of the endoplasmic reticulum. ATF6 is constitutively expressed in an inactive form in the membrane of the ER. Activation in response to ER stress results in proteolytic cleavage of its N-terminal cytoplasmic domain by the S2P serine protease to produce a potent transcriptional activator of chaperone genes (Yoshida et al. 1998 *J. Biol. Chem.* 273: 33741-33749; Li et al. 2000 *Biochem J* 350 Pt 1: 131-138; Ye et al. 2000 *Mol Cell* 6: 1355-1364; Yoshida et al. 2001 *Cell* 107: 881-891; Shen et al. 2002 *Dev Cell* 3: 99-111). The recently described ATF6β is closely related structurally to ATF6α and posited to be involved in the UPR (Haze et al. 2001 *Biochem J* 355: 19-28; Yoshida et al. 2001b Mol Cell Biol 21: 1239-1248). The third pathway acts at the level of posttranscriptional control of protein synthesis. An ER transmembrane component, PEK/PERK, related to PKR (interferon-induced double-stranded RNA-activated protein kinase) is a serine/threonine protein kinase that acts in the cytoplasm to phosphorylate eukaryotic initiation factor-2α (eIF2α). Phosphorylation of eIF2α results in translation attenuation in response to ER stress (Shi et al. 1998 *Mol. Cell. Biol.* 18: 7499-7509; Harding et al. 1999 *Nature* 397: 271-274).

The nucleotide and amino acid sequences of ATF6 are known in the art and can be found at, e.g., at GenBank accession number: gi:56786156.

As used herein, the various forms of the term "modulate" include stimulation (e.g., increasing or upregulating a particular response or activity) and inhibition (e.g., decreasing or downregulating a particular response or activity).

As used herein, the terms "a modulator of XBP-1" and "a modulator of IRE-1" include modulators of XBP-1 and/or IRE-1 expression, processing, post-translational modification, stability, and/or activity. The term includes agents, for example a compound or compounds which modulates transcription of, for example, an XBP-1 and/or IRE-1 gene, processing of an XBP-1 mRNA (e.g., splicing), translation of XBP-1 mRNA, post-translational modification of an XBP-1 and/or IRE-1 protein (e.g., glycosylation, ubiquitination), or activity of an XBP-1 and/or IRE-1 protein. In one embodiment, a modulator modulates one or more of the above. In preferred embodiments, the activity of XBP-1 and/or IRE-1 is modulated.

A "modulator of XBP-1 activity" and "a modulator of IRE-1 activity" include compounds that directly or indirectly modulate XBP-1 and/or IRE-1 activity. For example, an indirect modulator of XBP-1 activity can modulate a non-XBP-1 molecule which is in a signal transduction pathway that includes XBP-1. Examples of modulators that directly modulate XBP-1 expression, processing, post-translational modification, and/or activity include nucleic acid molecules encoding a biologically active portion of XBP-1, biologically active portions of XBP-1, antisense or siRNA nucleic acid molecules that bind to XBP-1 mRNA or genomic DNA, intracellular antibodies that bind to XBP-1 intracellularly and modulate (i.e., inhibit) XBP-1 activity, XBP-1 peptides that inhibit the interaction of XBP-1 with a target molecule (e.g., IRE-1) and expression vectors encoding XBP-1 that allow for increased expression of XBP-1 activity in a cell, dominant negative forms of XBP-1, as well as chemical compounds that act to specifically modulate the activity of XBP-1. Examples of modulators that directly modulate IRE-1 expression, processing, post-translational modification, and/or activity include nucleic acid molecules encoding a biologically active portion of IRE-1, biologically active portions of IRE-1, antisense or siRNA nucleic acid molecules that bind to IRE-1 mRNA or genomic DNA, IRE-1 peptides that inhibit the interaction of IRE-1 with a target molecule (e.g., XBP-1) and expression vectors encoding IRE-1 that allow for increased expression of IRE-1 activity in a cell, as well as chemical compounds that act to specifically modulate the activity of IRE-1.

As used interchangeably herein, the terms "XBP-1 activity," "biological activity of XBP-1" or "functional activity XBP-1," include activities exerted by XBP-1 protein on an XBP-1 responsive cell or tissue, e.g., a hepatocyte, a B cell, or on an XBP-1 nucleic acid molecule or protein target molecule, as determined in vivo, or in vitro, according to standard techniques. XBP-1 activity can be a direct activity, such as an association with an XBP-1-target molecule e.g., binding of spliced XBP-1 to a regulatory region of a gene responsive to XBP-1 (for example, a gene such as ERdj4, p58$^{ipk}$, EDEM, PDI-P5, RAMP4, HEDJ, BiP, ATF6α, XBP-1, Armet and/or DNAJB9), e.g., an unfolded protein response element (UPRE), or genes involved in de novo hepatic lipogenesis. Alternatively, an XBP-1 activity is an indirect activity, such as a downstream biological event mediated by interaction of the XBP-1 protein with an XBP-1 target molecule, e.g., IRE-1. The biological activities of XBP-1 are described herein and include: e.g., modulation of de novo hepatic lipogenesis, modulation of the UPR, modulation of cellular differentiation, modulation of IL-6 production, modulation of immunoglobulin production, modulation of the proteasome pathway, modulation of protein folding and transport, modulation of terminal B cell differentiation, and modulation of apoptosis.

As used interchangeably herein, the terms "IRE-1 activity," "biological activity of IRE-1" or "functional activity IRE-1," include activities exerted by IRE-1 protein on an IRE-1 responsive cell or tissue, e.g. a hepatocyte, a B cell, or on an IRE-1 nucleic acid molecule or protein target molecule, as determined in vivo, or in vitro, according to standard techniques. IRE-1 activity can be a direct activity, such as an association with an IRE-1-target molecule e.g., XBP-1 phosphorylation of a substrate (e.g., autokinase activity) or endoribonuclease activity on a substrate e.g., XBP-1 mRNA. Alternatively, an IRE-1 activity is an indirect activity, such as a downstream biological event mediated by interaction of the IRE-1 protein with an IRE-1 target molecule, e.g., XBP-1. As IRE-1 is in a signal transduction pathway involving XBP-1, modulation of IRE-1 modulates a molecule in a signal transduction pathway involving XBP-1. Modulators which modulate an XBP-1 biological activity indirectly modulate expression and/or activity of a molecule in a signal transduction pathway involving XBP-1, e.g., IRE-1, PERK, eIF2a, or ATF6a. The biological activities of IRE-1 are described herein and include: e.g., modulation of de novo hepatic lipogenesis, modulation of the UPR, modulation of the proteasome pathway, modulation of protein folding and transport, modulation of apoptosis, and modulation of a dyslipidemia, e.g., hyperlipidemia, hepatic steatosis, non-alcoholic hepatic steatohepatitis, and steatohepatitis.

"Activity of unspliced XBP-1" includes the ability to modulate the activity of spliced XBP-1. In one embodiment, unspliced XBP-1 competes for binding to target DNA sequences with spliced XBP-1. In another embodiment, unspliced XBP-1 disrupts the formation of homodimers or heterodimers (e.g., with cfos or ATF6α) by XBP-1.

As used herein, a "substrate" or "target molecule" or "binding partner" is a molecule with which a protein binds or interacts in nature, such that protein's function (e.g., modulation of de novo hepatic lipogenesis, activation of the UPR, apoptosis) is achieved. For example, a target molecule can be a protein or a nucleic acid molecule. Exemplary target molecules of the invention include proteins in the same signaling pathway as the XBP-1 and/or IRE-1 protein, e.g., proteins which can function upstream (including both stimulators and inhibitors of activity) or downstream of the XBP-1 and/or IRE-1 protein in a pathway involving regulation of, for example, modulation of de novo hepatic lipogenesis, modulation of ER stress, modulation of the UPR, modulation of the proteasome pathway, modulation of protein folding and transport, modulation of apoptosis. Exemplary XBP-1 target molecules include IRE-1, ATF6α, XBP-1 itself (as the molecule forms homodimers), cfos (which can form heterodimers with XBP-1) as well as the regulatory regions of genes regulated by XBP-1. Exemplary IRE-1 target molecules include XBP-1 and IRE-1 itself (as the molecule can form homodimers).

The subject methods can employ various target molecules. For example, in one embodiment, the subject methods employ XBP-1 or IRE-1. In another embodiment, the subject methods employ at least one other molecule, e.g., a molecule either upstream or downstream of XBP-1. For example, in one embodiment, the subject methods employ IRE-1. In another embodiment, the subject methods employ ATF6α.

As used herein, the term "chaperone gene" is includes genes that are induced as a result of the activation of the UPR or the EOR. The chaperone genes include, for example, members of the family of Glucose Regulated Proteins (GRPs) such as GRP78 (BiP) and GRP94 (endoplasmin), as well as other chaperones such as calreticulin, protein disulfide isomerase, and ERp72. The upregulation of chaperone genes helps accommodate the increased demand for the folding capacity within the ER.

As used herein, the term "gene whose transcription is regulated by XBP-1", includes genes having a regulatory region regulated by XBP-1. Such genes can be positively or negatively regulated by XBP-1. The term also includes genes which are indirectly regulated by XBP-1, e.g., are regulated by molecule in a signaling pathway in which XBP-1 is involved. Exemplary genes directly regulated by XBP-1 include, for example, lipogenic genes, e.g., fasn (gi: 41872631, gi:93102409), proprotein convertase subtilisin/kexin type 9 (PCSK9) (gi:31317307, gi:23956352), stearyl coA desaturase (gi:53759151, gi:31543675), diacyl glycerol acetyltransferase 2 (gi:26024197, gi:16975490), acetyl coA carboxylase 2 (gi:134142062, gi:157042798), genes such as ERdj4 (e.g., NM—012328 [gi:9558754]), p58ipk (e.g., XM-209778 [gi:2749842] or NM—006260 [gi:24234721]), EDEM (e.g., NM—014674 [gi:7662001]), PD1-P5 (e.g., NC—003284 [gi:32566600]), RAMP4 (e.g., AF136975 [gi: 12239332]), HEDJ (e.g., AF228505 [gi: 7385134]), BiP (e.g., X87949 [gi: 1143491]), ATF6a (e.g., NM—007348 [gi: 6671584], XBP-1 (e.g., NM—005080 [gi:14110394]), Armet (e.g., NM—006010 [gi:51743920]) and/or DNAJB9 (which encodes mDj7) e.g., (NM—012328 [gi:9558754]), the MHC class II genes (various MHC class II gene sequences are known in the art) and the IL-6 gene (e.g., NM—000600 [gi 10834983]).

Lipogenic gene promoters are known in the art and described herein, e.g., the DGAT2 promoter, and in, for example, S. Y. Oh et al. (2003) *J Biol Chem* 278, 28410; L Zhang, et al. Biochem J. 2001 Jul. 1; 357(Pt 1): 183-193; Jae-Jung LeeDagger et al. J. Biol. Chem., Vol. 276, Issue 4, 2576-2585, Jan. 26, 2001; Geneviève Dubuc et al. Arteriosclerosis, Thrombosis, and Vascular Biology. 2004; 24:1454. Lee, J. J., Moon, Y. A., Ha, J. H., Yoon, D. J., Ahn, Y. H., and Kim, K. S. (2001) *J. Biol. Chem.* 276, 2576-2585.

As used herein the term "apoptosis" includes programmed cell death which can be characterized using techniques which are known in the art. Apoptotic cell death can be characterized, e.g., by cell shrinkage, membrane blebbing and chromatin condensation culminating in cell fragmentation. Cells undergoing apoptosis also display a characteristic pattern of internucleosomal DNA cleavage. As used herein, the term "modulates apoptosis" includes either up regulation or down regulation of apoptosis in a cell.

As used herein, the term "contacting" (i.e., contacting a cell e.g. a cell, with a compound) includes incubating the compound and the cell together in vitro (e.g., adding the compound to cells in culture) as well as administering the compound to a subject such that the compound and cells of the subject are contacted in vivo. The term "contacting" does not include exposure of cells to an XBP-1 and/or IRE-1 modulator that may occur naturally in a subject (i.e., exposure that may occur as a result of a natural physiological process).

As used herein, the term "test compound" refers to a compound that has not previously been identified as, or recognized to be, a modulator of the activity being tested. The term "library of test compounds" refers to a panel comprising a multiplicity of test compounds.

As used herein, the term "indicator composition" refers to a composition that includes a protein of interest (e.g., XBP-1), for example, a cell that naturally expresses the protein, a cell that has been engineered to express the protein by introducing an expression vector encoding the protein into the cell, or a cell free composition that contains the protein (e.g., purified naturally-occurring protein or recombinantly-engineered protein).

As used herein, the term "cell" includes prokaryotic and eukaryotic cells. In one embodiment, a cell of the invention is a bacterial cell. In another embodiment, a cell of the invention is a fungal cell, such as a yeast cell. In another embodiment, a cell of the invention is a vertebrate cell, e.g., an avian or mammalian cell. In a preferred embodiment, a cell of the invention is a murine or human cell.

As used herein, the term "engineered" (as in an engineered cell) refers to a cell into which a nucleic acid molecule e.g., encoding an XBP-1 protein (e.g., a spliced and/or unspliced form of XBP-1) has been introduced.

As used herein, the term "cell free composition" refers to an isolated composition, which does not contain intact cells. Examples of cell free compositions include cell extracts and compositions containing isolated proteins.

As used herein, the term "reporter gene" refers to any gene that expresses a detectable gene product, e.g., RNA or protein. As used herein the term "reporter protein" refers to a protein encoded by a reporter gene. Preferred reporter genes are those that are readily detectable. The reporter gene can also be included in a construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979), Nature 282: 864-869) luciferase, and other enzyme detection systems, such as beta-galactosidase; firefly luciferase (deWet et al. (1987), *Mol. Cell. Biol.* 7:725-737); bacterial luciferase (Engebrecht and Silverman (1984), *PNAS* 1: 4154-4158; Baldwin et al. (1984), *Biochemistry* 23: 3663-3667); alkaline phosphatase (Toh et al. (1989) *Eur. J. Biochem.* 182: 231-238, Hall et al. (1983) *J. Mol. Appl. Gen.* 2: 101), human placental secreted alkaline phosphatase (Cullen and Malim (1992) *Methods in Enzymol.* 216:362-368) and green fluorescent protein (U.S. Pat. No. 5,491,084; WO 96/23898).

As used herein, the term "XBP-1-responsive element" refers to a DNA sequence that is directly or indirectly regulated by the activity of the XBP-1 (whereby activity of XBP-1 can be monitored, for example, via transcription of a reporter gene).

As used herein, the term "cells deficient in XBP-1" includes cells of a subject that are naturally deficient in XBP-1, as wells as cells of a non-human XBP-1 deficient animal, e.g., a mouse, that have been altered such that they are deficient in XBP-1. The term "cells deficient in XBP-1" is also intended to include cells isolated from a non-human XBP-1 deficient animal or a subject that are cultured in vitro.

As used herein, the term "non-human XBP-1 deficient animal" refers to a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal, such that the endogenous XBP-1 gene is altered, thereby leading to either no production of XBP-1 or production of a mutant form of XBP-1 having deficient XBP-1 activity. Preferably, the activity of XBP-1 is entirely blocked, although partial inhibition of XBP-1 activity in the animal is also encompassed. The term "non-human XBP-1 deficient animal" is also intended to encompass chimeric animals (e.g., mice) produced using a blastocyst complementation system, such as the RAG-2 blastocyst complementation system, in which a particular organ or organs (e.g., the lymphoid organs) arise from embryonic stem (ES) cells with homozygous mutations of the XBP-1 gene. The term "non-human XBP-1 deficient animal" is also intended to encompass animals (e.g., mice) that contain a conditional allele(s) of the XBP-1 gene, such as a cre-lox containing animal in which the XBP-1 gene is rendered nonfunctional following, e.g., mating of an animal containing a floxed allele with an animal containing a cre allele (cre recombinase) and injection of poly(I:C), as described in the appended examples.

As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

In one embodiment, a nucleic acid molecule of the invention is an siRNA molecule. In one embodiment, a nucleic acid molecule of the invention mediates RNAi. RNA interference (RNAi) is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. *Cell* 101, 25-33 (2000). Tuschl, T. et al. *Genes Dev.* 13, 3191-3197 (1999); Cottrell T R, and Doering T L. 2003. Trends Microbiol. 11:37-43; Bushman F. 2003. Mol. Therapy. 7:9-10; McManus M T and Sharp P A. 2002. Nat Rev Genet. 3:737-47). The process occurs when an endogenous ribonuclease cleaves the longer dsRNA into shorter, e.g., 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs or Ambion. In one embodiment one or more of the chemistries described herein or known in the art for use in antisense RNA can be employed in molecules that mediate RNAi.

As used herein, the term "dominant negative" includes molecules, such as XBP-1 molecules (e.g., portions or variants thereof) that compete with native (i.e., wild-type) XBP-1 molecules, but which do not have XBP-1 activity. Such molecules effectively decrease XBP-1 activity in a cell.

In one embodiment, small molecules can be used as test compounds. The term "small molecule" is a term of the art and includes molecules that are less than about 7500, less than about 5000, less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., Cane et al. 1998. Science 282:63), and natural product extract libraries. In another embodiment, the compounds are small, organic non-peptidic compounds. In a further embodiment, a small molecule is not biosynthetic. For example, a small molecule is preferably not itself the product of transcription or translation. In one embodiment, small molecule compounds are present on a microarray, see, e.g., Bradner J E, et al. 2006. Chem. Biol. 13(5):493-504.

Various aspects of the present invention are described in further detail in the following subsections.

II. Methods of Treatment and/or Prevention

XBP1 accelerates de novo fatty acid synthesis in the liver while preserving normal hepatic lipid composition, a profile that is highly relevant to the treatment of diseases that are associated with dyslipidemia. Accordingly, the invention provides for the prevention and/or treatment, and/or amelioration of at least one symptom, and/or normalization of at least one indicator of dyslipidemia, (that can lead to, e.g., atherosclerosis, hepatic steatosis, steatohepatitis, hypercholesteremia, obesity, insulin resistance, and/or non-alcoholic steatohepatitis) by modulating XBP-1 (e.g., by directly or indirectly modulating XBP-1) in cells, e.g., either in vitro or in vivo. In particular, the ability of a compound to modulate XBP-1 can be detected by measuring the ability of the compound to modulate a biological activity of XBP-1, e.g., by measuring modulation of de novo hepatic lipogenesis.

Accordingly, the invention features methods for treating and/or preventing a dyslipidemia (e.g., leading to, atherosclerosis, hepatic steatosis, steatohepatitis, hypercholesteremia, obesity, insulin resistance, and/or non-alcoholic steatohepatitis) by administering to a subject that would benefit from modulation of de novo hepatic lipogeneis, e.g., a subject having dyslipidemia, atherosclerosis, hepatic steatosis, steatohepatitis, hypercholesteremia, obesity, insulin resistance, and/or non-alcoholic steatohepatitis and/or contacting a cell from such a subject with a modulator of XBP-1 expression, processing, post-translational modification, and/or activity. The claimed methods are not meant to include naturally occurring events. For example, the step of contacting includes administering the modulator in a treatment protocol and, in one embodiment the term "agent" or "modulator" is not meant to embrace endogenous mediators produced by the cells of a subject.

The subject methods employ agents that modulate XBP-1 expression, processing, post-translational modification, or activity (or the expression, processing, post-translational modification, or activity of another molecule in an XBP-1 signaling pathway (e.g., IRE-1, ATF6α and/or PERK)) such that an XBP-1 and/or IRE-1 biological activity, e.g., de novo hepatic lipogenesis is modulated.

In one embodiment, the methods and compositions of the invention can be used to modulate XBP-1 expression, processing, post-translational modification, and/or activity in a cell. In one embodiment, the cell is a mammalian cell. In another embodiment, the cell is a human cell. In one embodiment, the cell is a hepatocyte. In one embodiment, the hepatocyte is an adult hepatocyte, i.e., a cell from a postnatal subject. Such modulation can occur in vitro or in vivo.

In one embodiment, cells in which, e.g., XBP-1, is modulated in vitro can be introduced, e.g., into an allogeneic subject, or e.g., reintroduced into a subject. In one embodiment, the invention also allows for modulation of XBP-1 in vivo, by administering to the subject an amount of a modulator of XBP-1 such that at least one symptom or indicator of de novo hepatic lipogenesis in a subject is modulated.

In one embodiment, a modulatory agent of the invention directly affects the expression, post-translational modification, and/or activity of XBP-1. In another embodiment, the expression of XBP-1 is modulated. In another embodiment, the post-translational modification of XBP-1 is modulated. In another embodiment, the activity of XBP-1 is modulated, e.g., de novo hepatic lipogenesis. In one embodiment, the agent modulates the interaction of XBP-1 with a DNA molecule to which XBP-1 binds, e.g., a Dgat2 promoter, a Scd1 promoter, an Acc2 promoter; and a PCSK9 promoter. In another embodiment, a modulatory agent of the invention indirectly affects the expression, post-translational modification, and/or activity of XBP-1.

The term "subject" is intended to include living organisms but preferred subjects are mammals. Examples of subjects include mammals such as, e.g., humans, monkeys, dogs, cats, mice, rats cows, horses, goats, and sheep.

Identification of compounds that modulate the biological effects of XBP-1 by directly or indirectly modulating XBP-1 activity allows for selective manipulation of these biological effects in a variety of clinical situations using the modulatory methods of the invention. For example, the stimulatory methods of the invention (i.e., methods that use a stimulatory agent) can result in increased expression, processing, post-translational modification, and/or activity of spliced XBP-1, which stimulates, e.g., de novo hepatic lipogenesis. In another embodiment, the stimulatory methods of the invention can be used to increase the expression, processing, post-translational modification, and/of activity of a negative regulator of XBP-1 (e.g., unspliced XBP-1 or a dominant negative form of XBP-1) to inhibit e.g., de novo hepatic lipogenesis.

In contrast, the inhibitory methods of the invention (i.e., methods that use an inhibitory agent) can inhibit the activity of spliced XBP-1 and inhibit, e.g., de novo hepatic lipogenesis.

In another embodiment, the inhibitory methods of the invention inhibit the activity of a negative regulator of XBP-1, e.g., unspliced XBP-1 or a dominant negative form of XBP-1. The XBP-1 unspliced protein is an example of an ubiquitinated and hence extremely unstable protein. XBP-1 spliced protein is not ubiquitinated, and has a much longer half life than unspliced XBP-1 protein. Proteasome inhibitors, for example, block ubiquitination, and hence stabilize XBP-1 unspliced but not spliced protein. Thus, the ratio of unspliced to spliced XBP-1 protein increases upon treatment with proteasome inhibitors. Since unspliced XBP-1 protein actually inhibits the function of the spliced protein, treatment with proteasome inhibitors blocks the activity of spliced XBP-1.

Modulation of XBP-1 activity, therefore, provides a means to regulate disorders arising from aberrant XBP-1 activity in various disease states. Thus, to treat and/or prevent a disorder wherein inhibition of a biological effect of spliced XBP-1 is desirable, such as a disorder that would benefit from reduced de novo hepatic lipogenesis is beneficial, an inhibitory method of the invention is selected such that spliced XBP-1 activity and/or expression is inhibited or a stimulatory method is selected which selectively stimulates the expression and/or activity of a negative regulator of XBP-1. Examples of disorders in which such inhibitory methods can be useful include, obesity (with or without effects of insulin resistance), diabetes, metabolic syndrome, hypertension, dyslipidemia associated with protease inhibitor treatment of HIV, dyslipidemia associated with antipsychotic treatment of schizophrenia, and chronic kidney disease. Dyslipidemia can lead to e.g., atherosclerosis, hepatic steatosis, steatohepatitis, and/or non-alcoholic steatohepatitis).

Alternatively, to treat and/or prevent a disorder wherein stimulation of a biological effect of spliced XBP-1 is desirable, such as a disorder that would benefit from increased de novo hepatic lipogenesis, a stimulatory method of the invention is selected such that spliced XBP-1 activity and/or expression is upregulated or an inhibitory method is selected such that the expression and/or activity of a negative regulator of XBP-1 is inhibited. Examples of disorders in which such stimulatory methods can be useful include hypothyroidism, chronic infections, malignancy, malnutrition, and malabsorption.

Application of the modulatory methods of the invention for the prevention, treatment, and/or amelioration of at least one symptom, or normalization of at least one indicator of a disorder can result in curing the disorder, a decrease in at least one symptom associated with the disorder, either in the long term or short term (i.e., amelioration of the condition) or simply a transient beneficial effect to the subject.

The methods of modulating XBP-1 can be practiced either in vitro or in vivo. For practicing the method in vitro, cells can be obtained from a subject by standard methods and incubated (i.e., cultured) in vitro with a stimulatory or inhibitory compound of the invention to stimulate or inhibit, respectively, the activity of XBP-1. Methods for isolating cells are known in the art.

Cells treated in vitro with either a stimulatory or inhibitory compound can be administered to a subject to influence the biological effects of XBP-1. For example, cells can be isolated from a subject, expanded in number in vitro and the activity of, e.g., spliced XBP-1, activity in the cells using a stimulatory agent, and then the cells can be readministered to the same subject, or another subject tissue compatible with the donor of the cells. Accordingly, in another embodiment, the modulatory method of the invention comprises culturing cells in vitro with e.g., an XBP-1 modulator and further comprises administering the cells to a subject. For administration of cells to a subject, it may be preferable to first remove residual compounds in the culture from the cells before administering them to the subject. This can be done for example by gradient centrifugation of the cells or by washing of the tissue. For further discussion of ex vivo genetic modification of cells followed by readministration to a subject, see also U.S. Pat. No. 5,399,346 by W. F. Anderson et al.

In other embodiments, a stimulatory or inhibitory compound is administered to a subject in vivo. Such methods can be used to treat disorders, e.g., as detailed above. In one embodiment, a stim or inhib compound is delivered directly to hepatocytes, e.g., adult hepatocytes, using methods known in the art.

For stimulatory or inhibitory agents that comprise nucleic acids (e.g., recombinant expression vectors encoding, e.g., XBP-1; antisense RNA; or e.g., XBP-1 derived peptides), the compounds can be introduced into cells of a subject using methods known in the art for introducing nucleic acid (e.g., DNA) into cells. Examples of such methods include:

Direct Injection: Naked DNA can be introduced into cells in vivo by directly injecting the DNA into the cells (see e.g., Acsadi et al. (1991) *Nature* 332:815-818; Wolff et al. (1990) *Science* 247:1465-1468). For example, a delivery apparatus (e.g., a "gene gun") for injecting DNA into cells in vivo can be used. Such an apparatus is commercially available (e.g., from BioRad).

Receptor-Mediated DNA Uptake: Naked DNA can also be introduced into cells in vivo by complexing the DNA to a cation, such as polylysine, which is coupled to a ligand for a cell-surface receptor (see for example Wu, G. and Wu, C. H. (1988) *J. Biol. Chem.* 263:14621; Wilson et al. (1992) *J. Biol. Chem.* 267:963-967; and U.S. Pat. No. 5,166,320). Binding of the DNA-ligand complex to the receptor facilitates uptake of the DNA by receptor-mediated endocytosis. A DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88:8850; Cristiano et al. (1993) *Proc. Natl. Acad. Sci. USA* 90:2122-2126).

Retroviruses: Defective retroviruses are well characterized for use in gene transfer for gene therapy purposes (for a review see Miller, A. D. (1990) *Blood* 76:271). A recombinant retrovirus can be constructed having a nucleotide sequences of interest incorporated into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include $\psi$Crip, $\psi$Cre, $\psi$2 and $\psi$Am. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150:4104-4115; U.S. Pat. Nos. 4,868,116; 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenoviruses: The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482-6486), hepatocytes (Herz and Gerard (1993) *Proc. Natl. Acad. Sci. USA* 90:2812-2816) and muscle cells (Quantin et al. (1992) *Proc. Natl. Acad. Sci. USA* 89:2581-2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use are deleted for all or parts of the viral E1 and E3 genes but retain as much as 80% of the adenoviral genetic material.

Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay.

In one embodiment, if the stimulatory or inhibitory compounds can be administered to a subject as a pharmaceutical composition. In one embodiment, the invention is directed to an active compound (e.g., a modulator of XBP-1) and a carrier. Such compositions typically comprise the stimulatory or inhibitory compounds, e.g., as described herein or as identified in a screening assay, e.g., as described herein, and a pharmaceutically acceptable carrier. Pharmaceutically acceptable carriers and methods of administration to a subject are described herein.

In one embodiment, the active compounds of the invention are administered in combination with other agents. For example, in one embodiment, an active compound of the invention, e.g., a compound that modulates an XBP-1 signal transduction pathway (e.g., by directly modulating XBP-1 activity) is administered with another compound known in the art to be useful in treatment of a particular condition or disease. For example, in one embodiment, an active compound of the invention (e.g., a proteasome inhibitor or a compound that directly modulates XBP-1 activity) can be administered or in combination with an agent that induces ER stress in cells (e.g., an agent such as tunicamycin, an agent that modulates Ca++ influx in cells, or an anti-angiogenic factor that increases hypoxia in the cells of a tumor). In another embodiment of the invention, a proteasome inhibitor can be used in combination with an agent that induces ER stress in cells to disrupt the UPR. In one embodiment, treatment of cells with a proteasome inhibitor and an agent that induces ER stress results in apoptosis of the cells. In one embodiment, an HMG-CoA reductase inhibitor can be used in combination with an agent, e.g., a nucleic acid molecule that downmodulated XBP-1 and/or IRE-1. HMG-CoA reductase inhibitors, also referred to as statins, are a class of hypolipidemic drugs used to lower cholesterol levels in subjects with or at risk of cardiovascular disease. They lower cholesterol by inhibiting the enzyme HMG-CoA reductase, which is the rate-limiting enzyme of the mevalonate pathway of cholesterol synthesis. Inhibition of this enzyme in the liver stimulates LDL receptors, resulting in an increased clearance of low-density lipoprotein (LDL) from the bloodstream and a decrease in blood cholesterol levels.

Statins are divided into two groups: fermentation-derived and synthetic which include, for example Atorvastatin, Cerivastatin, Fluvastatin, Lovastatin, Mevastatin, Pitavastatin, Pravastatin, Rosuvastatin, Simvastatin, Simvastatin+ Ezetimibe, Lovastatin+Niacin, Atorvastatin+Amlodipine, Simvastatin+Niacin.

Compounds that can be used in the methods of the invention is described in further detail below.

A. Stimulatory Compounds

The methods of the invention using spliced XBP-1 stimulatory compounds can be used in the prevention and/or treatment of disorders in which spliced XBP activity and/or expression is undesirably reduced, inhibited, downregulated, or the like. For example, dyslipidemia, e.g., hypolipidemia is associated with hypothyroidism, chronic infections, malignancy, malnutrition, and malabsorption. Accordingly, preferred disorders for treatment using a stimulatory compound of the invention include, e.g., hypolipidemia is associated with hypothyroidism, chronic infections, malignancy, malnutrition, and malabsorption. In one embodiment, the stimulatory methods of the invention, a subject is treated with a stimulatory compound that stimulates expression and/or activity of spliced XBP-1. In another embodiment, a stimulatory method of the invention can be used to stimulate the expression and/or activity of a negative regulator of spliced XBP-1 activity.

Examples of stimulatory compounds include XBP-1 polypeptides, proteins, or biologically active fragments thereof, nucleic acid molecules encoding XBP-1 proteins or biologically active fragments thereof, and chemical agents that stimulate expression and/or activity of the protein of interest.

In one embodiment, stimulatory compound is a nucleic acid molecule encoding unspliced XBP-1 that is capable of being spliced or spliced XBP wherein the nucleic acid molecule is introduced into the subject in a form suitable for expression of the protein in the cells of the subject. For example, an XBP-1 cDNA (full length or partial cDNA sequence) is cloned into a recombinant expression vector and the vector is transfected into cells using standard molecular biology techniques. The XBP-1 cDNA can be obtained, for example, by amplification using the polymerase chain reaction (PCR) or by screening an appropriate cDNA library. The nucleotide sequences of XBP-1 cDNA are known in the art and can be used for the design of PCR primers that allow for amplification of a cDNA by standard PCR methods or for the design of a hybridization probe that can be used to screen a cDNA library using standard hybridization methods. Another preferred stimulatory compound is a nucleic acid molecule encoding the spliced form of XBP-1.

Following isolation or amplification of XBP-1 cDNA or cDNA encoding a molecule in a signal transduction pathway involving XBP-1, the DNA fragment is introduced into a suitable expression vector, as described above. For example, nucleic acid molecules encoding XBP-1 in the form suitable for expression of the XBP-1 in a host cell, can be prepared as described above using nucleotide sequences known in the art. The nucleotide sequences can be used for the design of PCR primers that allow for amplification of a cDNA by standard PCR methods or for the design of a hybridization probe that can be used to screen a cDNA library using standard hybridization methods.

In one embodiment, a stimulatory agent can be present in an inducible construct. In another embodiment, a stimulatory agent can be present in a construct which leads to constitutive expression.

Another form of a stimulatory compound for stimulating expression of XBP-1 or a molecule in a signal transduction pathway involving XBP-1 in a cell is a chemical compound that specifically stimulates the expression, processing, post-translational modification, or activity of endogenous spliced XBP-1. Such compounds can be identified using screening assays that select for compounds that stimulate the expression of XBP-1 that can be spliced or activity of spliced XBP-1 as described herein.

B. Inhibitory Compounds

The methods of the invention using inhibitory compounds which inhibit the expression, processing, post-translational modification, or activity of spliced XBP-1 can be used in the prevention and/or treatment of disorders in which spliced XBP-1 activity is undesirably enhanced, stimulated, upregulated or the like, For example, dyslipidemia, e.g., hyperlipidemia, hepatic steatosis, non-alcoholic hepatic steatohepatitis, and steatohepatitis are associated with obesity (with or without effects of insulin resistance), diabetes, metabolic syndrome, hypertension, atherosclerosis, dyslipidemia associated with protease inhibitor treatment of HIV, dyslipidemia associated with antipsychotic treatment of schizophrenia, and chronic kidney disease. Accordingly, preferred disorders for prevention and/or treatment using an inhibitory compound of the invention include, e.g., obesity (with or without effects of insulin resistance), diabetes, metabolic syndrome, hypertension, atherosclerosis, dyslipidemia associated with protease inhibitor treatment of HIV, dyslipidemia associated with antipsychotic treatment of schizophrenia, and chronic kidney disease.

In a preferred embodiment, inhibitory compounds can be used to inhibit the expression, processing, post-translational modification, or activity of a negative regulator of XBP-1, e.g., unspliced XBP-1. Such compounds can be used in the treatment of disorders in which unspliced XBP-1 is undesirably elevated or when spliced XBP-1 expression and/or activity is undesirably reduced.

In one embodiment of the invention, an inhibitory compound can be used to inhibit (e.g., specifically inhibit) the expression, processing, post-translational modification, or activity of spliced XBP-1. Preferably, an inhibitory compound can be used to inhibit (e.g., specifically inhibit) the expression, processing, post-translational modification, or activity of unspliced XBP-1.

Inhibitory compounds of the invention can be, for example, intracellular binding molecules that act to specifically inhibit the expression, processing, post-translational modification, or activity e.g., of XBP-1 or a molecule in a signal transduction pathway involving XBP-1 (e.g., IRE-1). As used herein, the term "intracellular binding molecule" is intended to include molecules that act intracellularly to inhibit the processing expression or activity of a protein by binding to the protein or to a nucleic acid (e.g., an mRNA molecule) that encodes the protein. Examples of intracellular binding molecules, described in further detail below, include antisense nucleic acids, peptidic compounds that inhibit the interaction of XBP-1 with a target molecule and chemical agents that specifically inhibit XBP-1 activity.

i. Antisense or siRNA Nucleic Acid Molecules

In one embodiment, an inhibitory compound of the invention is an antisense nucleic acid molecule that is complementary to a gene encoding XBP-1, or to a portion of said gene, or a recombinant expression vector encoding said antisense nucleic acid molecule. The use of antisense nucleic acids to downregulate the expression of a particular protein in a cell is well known in the art (see e.g., Weintraub, H. et al., Antisense RNA as a molecular tool for genetic analysis, Reviews—Trends in Genetics, Vol. 1(1) 1986; Askari, F. K. and McDonnell, W. M. (1996) N. Eng. J. Med. 334:316-318; Bennett, M. R. and Schwartz, S. M. (1995) Circulation 92:1981-1993; Mercola, D. and Cohen, J. S. (1995) Cancer Gene Ther. 2:47-59; Rossi, J. J. (1995) Br. Med. Bull. 51:217-225; Wagner, R. W. (1994) Nature 372:333-335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA.

Given the known nucleotide sequence for the coding strand of the XBP-1 gene and thus the known sequence of the XBP-1 mRNA, antisense nucleic acids of the invention can be designed according to the rules of Watson and Crick base pairing. The antisense nucleic acid molecule can be complementary to the entire coding region of an mRNA, but more preferably is antisense to only a portion of the coding or noncoding region of an mRNA. For example, the antisense oligonucleotide can be complementary to the region surrounding the translation start site of an XBP-1 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl) uracil, (acp3) w, and 2,6-diaminopurine. To inhibit expression in cells, one or more antisense oligonucleotides can be used.

Alternatively, an antisense nucleic acid can be produced biologically using an expression vector into which all or a portion of a cDNA has been subcloned in an antisense orientation (i.e., nucleic acid transcribed from the inserted nucleic acid will be of an antisense orientation to a target nucleic acid of interest). Regulatory sequences operatively linked to a nucleic acid cloned in the antisense orientation can be chosen which direct the expression of the antisense RNA molecule in a cell of interest, for instance promoters and/or enhancers or other regulatory sequences can be chosen which direct constitutive, tissue specific or inducible expression of antisense RNA. The antisense expression vector is prepared according to standard recombinant DNA methods for constructing recombinant expression vectors, except that the cDNA (or portion thereof) is cloned into the vector in the antisense orientation. The antisense expression vector can be in the form of, for example, a recombinant plasmid, phagemid or attenuated virus. The antisense expression vector can be introduced into cells using a standard transfection technique.

The antisense nucleic acid molecules of the invention are typically administered to a subject or generated in situ such that they hybridize with or bind to cellular mRNA and/or genomic DNA encoding a protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of an antisense nucleic acid molecule of the invention includes direct injection at a tissue site. Alternatively, an antisense nucleic acid molecule can be modified to target selected cells and then administered systemically. For example, for systemic administration, an antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, an antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid molecule of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave mRNA transcripts to thereby inhibit translation mRNAs. A ribozyme having specificity e.g., for an XBP-1, IRE-1, or ATF6α-encoding nucleic acid can be designed based upon the nucleotide sequence of the cDNA. For example, a derivative of a *Tetrahymena* L-19 IVS RNA can be constructed in which the nucleotide sequence of the active site is complementary to the nucleotide sequence to be cleaved in, e.g., an XBP-1-encoding mRNA. See, e.g., Cech et al. U.S. Pat. No. 4,987,071 and Cech et al. U.S. Pat. No. 5,116,742. Alternatively, XBP-1 mRNA can be used to select a catalytic RNA having a specific ribonuclease activity from a pool of RNA molecules. See, e.g., Bartel, D. and Szostak, J. W. (1993) *Science* 261:1411-1418.

Alternatively, gene expression can be inhibited by targeting nucleotide sequences complementary to the regulatory region of a gene (e.g., an XBP-1 promoter and/or enhancer) to form triple helical structures that prevent transcription of a gene in target cells. See generally, Helene, C. (1991)*Anticancer Drug Des.* 6(6):569-84; Helene, C. et al. (1992) *Ann. N.Y. Acad. Sci.* 660:27-36; and Maher, L. J. (1992) *Bioassays* 14(12):807-15.

In another embodiment, a compound that promotes RNAi can be used to inhibit expression of XBP-1. RNA interference (RNAi is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. *Cell* 101, 25-33 (2000). Tuschl, T. et al. *Genes Dev.* 13, 3191-3197 (1999); Cottrell T R, and Doering T L. 2003. Trends Microbiol. 11:37-43; Bushman F. 2003. Mol. Therapy. 7:9-10; McManus M T and Sharp P A. 2002. Nat Rev Genet. 3:737-47). The process occurs when an endogenous ribonuclease cleaves the longer dsRNA into shorter, e.g., 21- or 22-nucleotide-long RNAs; termed small interfering RNAs or siRNAs. The smaller RNA segments then mediate the degradation of the target mRNA. Kits for synthesis of RNAi are commercially available from, e.g. New England Biolabsor Ambion. In one embodiment one or more of the chemistries described above or known in the art for use in antisense RNA can be employed in molecules that mediate RNAi. A working example of XBP-1 specific RNAi in which an XBP-1-specific RNAi vector was constructed by inserting two complementary oligonucleotides for 5'-GGGATTCAT-GAATGGCCCTTA-3' (SEQ ID NO:2) into the pBS/U6 vector.

Exemplary siRNA molecules specific for the unspliced form of murine XBP-1 are shown below:

```
Beginning at position 711:
Sense strand siRNA:
GUUGGACCCUGUCAUGUUUtt         (SEQ ID NO.: 3)

Antisense strand siRNA:
AAACAUGACAGGGUCCAACtt         (SEQ ID NO.: 4)

Beginning at position 853:
Sense strand siRNA:
GCCAUUAAUGAACUCAUUCtt         (SEQ ID NO.: 5)

Antisense strand siRNA:
GAAUGAGUUCAUUAAUGGCtt         (SEQ ID NO.: 6)
```

Exemplary siRNA molecules specific for the spliced form of murine XBP-1 are shown below:

```
Beginning at position 746:
Sense strand siRNA:
GAAGAGAACCACAAACUCCUU          (SEQ ID NO.: 7)

Antisense strand siRNA:
GGAGUUUGUGGUUCUCUUCUU          (SEQ ID NO.: 8)

Beginning at position 1307:
Sense strand siRNA:
GAGGAUCACCCUGAAUUCAUU          (SEQ ID NO.: 9)

Antisense strand siRNA:
UGAAUUCAGGGUGAUCCUCUU          (SEQ ID NO.: 10)
```

Exemplary siRNA molecules specific for the unspliced form of human XBP-1 are shown below:

```
Beginning at position 729:
Sense strand siRNA:
CUUGGACCCAGUCAUGUUCUU          (SEQ ID NO.: 11)

Antisense strand siRNA:
GAACAUGACUGGGUCCAAGUU          (SEQ ID NO.: 12)

Beginning at position 1079:
Sense strand siRNA:
AUCUGCUUUCAUCCAGCCAUU          (SEQ ID NO.: 13)

Antisense strand siRNA:
UGGCUGGAUGAAAGCAGAUUU          (SEQ ID NO.: 14)
```

Exemplary siRNA molecules specific for the spliced form of human XBP-1 are shown below:

```
Beginning at position 884:
Sense strand siRNA:
GCCCCUAGUCUUAGAGAUAUU          (SEQ ID NO.: 15)

Antisense strand siRNA:
UAUCUCUAAGACUAGGGGCUU          (SEQ ID NO.: 16)

Beginning at position 1108:
Sense strand siRNA:
GAACCUGUAGAAGAUGACCUU          (SEQ ID NO.: 17)

Antisense strand siRNA:
GGUCAUCUUCUACAGGUUCUU.         (SEQ ID NO.: 18)
```

Exemplary siRNA molecules specific for IRE-1 are shown below:

```
Beginning at position 345:
Sense strand siRNA: Sense strand siRNA:
UGAUGGCAGCCUGUAUACGUU          (SEQ ID NO.: 26)

Antisense strand siRNA:
CGUAUACAGGCUGCCAUCAUU          (SEQ ID NO.: 19)

Beginning at position 1161:
Sense strand siRNA:
CAAGCUCAACUACUUGAGGUU          (SEQ ID NO.: 20)

Antisense strand siRNA:
CCUCAAGUAGUUGAGCUUGUU.         (SEQ ID NO.: 21)
```

In one embodiment, an XBP-1 and/or IRE-1 siRNA molecule is specifically targeted to a hepatocyte by, for example coupling one or both strands of an XBP-1 siRNA molecule to cholesterol (see, e.g., Cheng, et al. (2006) *J Pharmacol Exp Ther* 317:797; Soutschek, et al. (2004) *Biochemistry* 43:13348, the contents of each of which are hereby incorporated by reference).

In one embodiment, therapeutic siRNA molecules are encapsulated in lipid particles. Methods for encapsulating nucleic acid molecules in lipids are known in the art and can be found in, for example, US20060051405, US20050175682, WO9851278, U.S. Pat. Nos. 6,534,484, 6,858,225, US20050008689

In another embodiment siRNA molecules are incorporated into lipid nanoparticles, e.g., SNALPs. For example, single-stranded RNAs are deprotection and purified of the crude oligoribonucleotides by anion exchange HPLC according to established procedures. siRNAs are subsequently generated by annealing equimolar amounts of complementary sense and antisense strands. Such siRNA are formulated into LNP Lipidoid Nanoparticles by, for example preparing stock solutions of lipidoid 98N12-5 (1)•4HCl, cholesterol, and mPEG2000-DMG MW 2660 in ethanol and mixing the solutions to yield a molar ratio of 42:48:10 (Akinc A, et al. (2008) Nat Biotechnol 26:561-569). siRNA are incorporated in the nanoparticles at 1:7.5 (wt:wt) siRNA:total lipids. Resulting particles had a mean particle diameter of {approx}50 nm and siRNA entrapment efficiency of >95%. For siRNA transfection experiments, cells, e.g., HepG2 or primary hepatocyte, are transfected by using Lipofectamine 2000.

ii. Peptidic Compounds

In another embodiment, an inhibitory compound of the invention is a peptidic compound derived from the XBP-1 amino acid sequence. For example, in one embodiment, the inhibitory compound comprises a portion of, e.g., XBP-1 (or a mimetic thereof) that mediates interaction of XBP-1 with a target molecule such that contact of XBP-1 with this peptidic compound competitively inhibits the interaction of XBP-1 with the target molecule.

The peptidic compounds of the invention can be made intracellularly in cells by introducing into the cells an expression vector encoding the peptide. Such expression vectors can be made by standard techniques using oligonucleotides that encode the amino acid sequence of the peptidic compound. The peptide can be expressed in intracellularly as a fusion with another protein or peptide (e.g., a GST fusion). Alternative to recombinant synthesis of the peptides in the cells, the peptides can be made by chemical synthesis using standard peptide synthesis techniques. Synthesized peptides can then be introduced into cells by a variety of means known in the art for introducing peptides into cells (e.g., liposome and the like).

In addition, dominant negative proteins (e.g., of XBP-1) can be made which include XBP-1 molecules (e.g., portions or variants thereof) that compete with native (i.e., wild-type) molecules, but which do not have the same biological activity. Such molecules effectively decrease, e.g., XBP-1 activity in a cell. For example, the peptide compound can be lacking part of an XBP-1 transcriptional activation domain, e.g., can consist of the portion of the N-terminal 136 or 188 amino acids of the spliced form of XBP-1.

iv. Other Agents that Act Upstream of XBP-1

In one embodiment, the expression of spliced XBP-1 can be inhibited using an agent that inhibits a signal that increases XBP-1 expression, processing, post-translational modification or activity in a cell. Both IL-4 and IL-6 have been shown to increase transcription of XBP-1 (Wen et al. 1999. Int. Journal of Oncology 15:173). Accordingly, in one embodiment, an agent that inhibits a signal transduced by IL-4 or IL-6 can be used to downmodulate XBP-1 expression and, thereby, decrease the activity of spliced XBP-1 in a cell. For example, in one embodiment, an agent that inhibits a STAT-6 dependent signal can be used to decrease the expression of XBP-1 in a cell.

Other inhibitory agents that can be used to specifically inhibit the activity of an XBP-1 or a molecule in a signal transduction pathway involving XBP-1 are chemical compounds that directly inhibit expression, processing, post-translational modification, and/or activity of, e.g., an XBP-1 target protein activity or inhibit the interaction between, e.g., XBP-1 and target molecules. Such compounds can be identified using screening assays that select for such compounds, as described in detail above as well as using other art recognized techniques.

III. Pharmaceutical Compositions

A pharmaceutical composition comprising a compound of the invention, e.g., a stimulatory or inhibitory molecule of the invention or a compound identified in the subject screening assays, is formulated to be compatible with its intended route of administration. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid; buffers such as acetates, citrates or phosphates and compounds for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition will preferably be sterile and should be fluid to the extent that easy syringability exists. It will preferably be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal compounds, for example, parabens, chlorobutanol, phenol, ascorbic acid, thimerosal, and the like. In many cases, it will be preferable to include isotonic compounds, for example, sugars, polyalcohols such as manitol, sorbitol, sodium chloride in the composition. Prolonged absorption of the injectable compositions can be brought about by including in the composition an compound which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

In one embodiment, the test compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from, e.g., Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In one embodiment, a modulatory agent of the invention is administered in amount sufficient to modulate de novo hepatic lipogenesis, e.g., such that at lest one indicator of de novo hepatic lipogenesis is brought within normal levels. Such indicators may be measured by analyzing serum lipid levels according to methods routine to one of ordinary skill in the art.

In one embodiment, a liposomal complex of an XBP-1 or IRE-1 siRNA is administered to a subject at about 0.05, 0.1, 0.5, 1, 1.5, 2, 2.5, 3, 3.5, 4, 4.5, 5, 5.5, 6, 6.5 7, 7.5, 8, 8.5, 9, 9.5, 10 mg/kg.

IV. Screening Assays

In one embodiment, the invention provides methods (also referred to herein as "screening assays") for identifying agents for preventing and/or treating (e.g., modulating at least one symptom of) dyslipidemia e.g., that can lead to atherosclerosis, hepatic steatosis, steatohepatitis, hypercholesteremia, obesity, insulin resistance, and/or non-alcoholic steatohepatitis, i.e., candidate or test compounds or agents (e.g., enzymes, peptides, peptidomimetics, small molecules, ribozymes, or antisense or siRNA molecules) which modulate de novo hepatic lipogenesis. The subject assays involve testing the effect of a candidate agent on de novo hepatic lipogenesis using methods known in the art or described herein. In one embodiment, the subject assays further comprise a step in which the effect of the agent on another activity of XBP-1 or on an activity or IRE-1 is measured, the ability to bind to XBP-1 is measured (e.g., in vitro or in silico), or an effect on the expression, processing (e.g., splicing), post-translational modification (e.g., glycosylation, ubiquitination, phosphorylation, or stability) is measured In one embodiment, the ability of a compound to modulate de novo hepatic lipogenesis is measured in a screening assay of the invention. In another embodiment, the ability of a compound to directly modulate the expression, processing (e.g., splicing), post-translational modification (e.g., glycosylation, ubiquitination, or phosphorylation), stability or activity of XBP-1 and/or IRE-1 alpha is measured in a screening assay of the invention.

The indicator composition can be a cell that expresses the XBP-1 and/or IRE-1 alpha protein, for example, a cell that naturally expresses or, more preferably, a cell that has been engineered to express the protein by introducing into the cell an expression vector encoding the protein. Preferably, the cell is a mammalian cell, e.g., a human cell. In another embodiment, the cell is a hepatocyte. In one embodiment, the hepatocyte is an adult hepatocyte, i.e., a cell from a postnatal subject. In another embodiment, the cell is a hepatoma cell, e.g., a human hepatoma cell, a rat hepatoma cell. In one embodiment, the cell is a HeLa cell. Alternatively, the indicator composition can be a cell-free composition that includes the protein (e.g., a cell extract or a composition that includes e.g., either purified natural or recombinant protein). In one embodiment, the cell is under ER stress.

Compounds identified as upmodulating the expression, activity, and/or stability of spliced XBP-1 and/or the expression and/or activity of IRE-1, and/or de novo hepatic lipogenesis using the assays described herein are useful for preventing and/or treating dyslipidemia, e.g., hypolipidemia.

Exemplary condition(s) that can benefit from upmodulation include, for example, hyperthyroidism, chronic infections, malignancy, malnutrition, and malabsorption, and symptoms associated therewith. Compounds identified as downmodulating the expression, activity, and/or stability of spliced XBP-1 and/or the expression and/or activity of IRE-1 using the assays described herein are useful for treating and/or preventing dyslipidemia, e.g., hyperlipidemia, atherosclerosis, hepatic steatosis, non-alcoholic hepatic steatohepatitis, and steatohepatitis. Exemplary condition(s) that can benefit from downmodulation include, for example, obesity (with or without effects of insulin resistance), diabetes, metabolic syndrome, diabetes, hypertension, atherosclerosis, dyslipidemia associated with protease inhibitor treatment of HIV, dyslipidemia associated with antipsychotic treatment of schizophrenia, and chronic kidney disease.

The subject screening assays can be performed in the presence or absence of other agents. In one embodiment, the subject assays are performed in the presence of an agent that affects the unfolded protein response, e.g., tunicamycin, which evokes the UPR by inhibiting N-glycosylation, or thapsigargin. In another embodiment, the subject assays are performed in the presence of an agent that inhibits degradation of proteins by the ubiquitin-proteasome pathway (e.g., peptide aldehydes, such as MG132). In another embodiment, the screening assays can be performed in the presence or absence of a molecule that enhances cell activation. In another embodiment, the subject cell assays are conducted in the presence of high concentrations of glucose.

In another aspect, the invention pertains to a combination of two or more of the assays described herein. For example, an agent that modulates de novo hepatic lipogenesis can be identified using a cell-based or a cell-free assay, and the ability of the agent to modulate the activity of XBP-1 or a molecule in a signal transduction pathway involving XBP-1 can be determined as described herein.

Similarly, a modulating agent can be identified using a cell-based or a cell-free assay, and the ability of the agent to modulate the activity of XBP-1 or a molecule in a signal transduction pathway involving XBP-1 can be confirmed in vivo, e.g., in an animal model for cardiovascular disease, atherosclerosis, diabetes, obesity and/or dyslipidemia.

For example, in one embodiment, a modulating agent identified using the cell-based or cell-free assays described herein may be assayed in a non-human animal model of obesity and/or insulin resistance, e.g., a genetic model of obesity and/or insulin resistance, e.g., ob, db animals, and/or dietary models of obesity and/or insulin resistance, e.g., a high carbohydrate diet. Such methods generally comprise administering the test compound to the non-human animal and determining the effect of the agent on for example, body weight, serum triglycerides, total cholesterol, blood glucose, glucose tolerance, insulin tolerance, and glucose-stimulated insulin secretion in the presence and absence of the test compound.

In another embodiment, a modulating agent identified using the cell-based or cell-free assays described herein may be assayed in a non-human animal model of non-alcoholic hepatosteatosis, e.g., a dietary induced model of non-alcoholic hepatosteatosis, e.g., a diet deficient in methionine and choline and/or with an atherogenic diet, e.g., a diet containing 1.25% cholesterol and 0.5% cholic acid (Matsuzawa N, et al. S. 2007. Hepatology 46: 1392-403). Such methods generally comprise providing an atherogenic and/or diet deficient in methionine and choline to the non-human animal, administering the test compound to the non-human animal, and determining the effect of the compound on, for example, aspartate aminotransferase level, alanine aminotransferase level, liver cell inflammation, and presence of triglyceride vacuoles in a liver cell.

In another embodiment, a modulating agent identified using the cell-based or cell-free assays described herein may be assayed in a non-human animal model of hypercholesterolemia and/or atherosclerosis, e.g. a genetic model of hypercholesterolemia and/or atherosclerosis, e.g., ApoE, ApoB, LDLR, and/or dietary models of hypercholesterolemia and/or atherosclerosis, e.g., a high fat diet. Such methods generally comprise administering the test compound to the non-human animal and determining the effect of the compound on, for example, serum triglycerides, total cholesterol, distribution of cholesterol among HDL, IDL, VLDL, and LDL, and presence of atherosclerotic lesions as assessed by standard hostologic analysis, as described in, for example, Palinski W, et al. Arterioscler Thromb. 1994; 14:605; Nunnari J J, et al. Exp Mol Pathol. 1989; 51:1.

Liver function tests can be performed on serum samples using an automated analyzer and can include, for example, measurement of serum lactate dehydrogenase (LDH), serum glutamic-oxaloacetic transaminase (SGOT), serum glutamic-pyruvate transaminase (SGPT), and serum bilirubin.

Figure 8A:
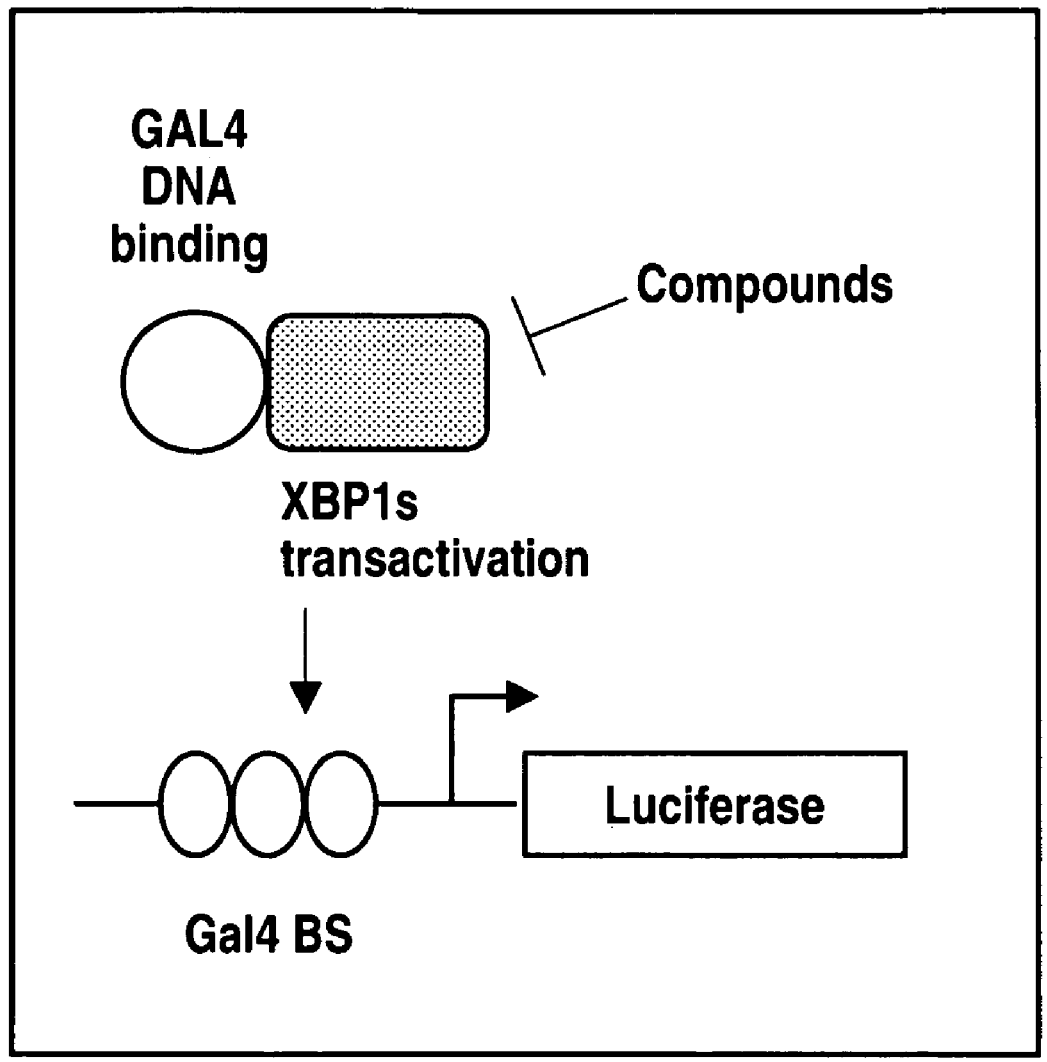
FIG. 8A is a shematic of an exemplary assay to identify compounds that modulate, e.g., inhibit, the activity of XBP-1 by, e.g., binding to the transactivation domain of XBP-1 and inhibiting the transactivation activity of XBP-1.
Figure 8B:
FIG. 8B is a graph depicting the results of such an assay. Fifty-five of 10,000 compounds identified by a small-molecule microarray assay were assayed as depicted in FIG. 8A and found to inhibit the expression of the reporter gene (shown in light gray).

In addition, a modulating agent can be identified using a cell-based or a cell-free assay, and the ability of the agent to modulate XBP-1 activity, IRE-1 activity de novo hepatic lipogeneis, and/or hepatic lipid metabolism, and/or endoplasmic reticulum (ER) stress, and/or the uncoupled protein response, may be further evaluated. For example, in one embodiment, a modulating agent identified as interacting with XBP-1, e.g., the transactivation domain, may be further assayed (e.g., in a secondary screen) for the ability to modulate the UPR using, for example, a UPR reporter assay (as described herein and known in the art (see, e.g., FIGS. 8A and 8B). Furthermore, agents identified in the secondary screen as inhibiting the transactivation of XBP-1 in a UPR reporter assay may be further assayed (e.g., in a tertiary screen) by determining the effect of the agents on hepatic lipogenesis by, for example determining the rate of free fatty acid synthesis and sterol synthesis in a cell based assay, such as in hepatoma cells. For example, the rate of fatty acid and sterol synthesis may be assayed by contacting a cell with an agent identified as interacting with XBP-1 and inhibiting the transactivation of XBP-1, which cell is incubated in the presence of radiolabeled acetate-1 (e.g., $C^{14}$) and identifying a compound which decreases or inhibits the incorporation of radiolabeled acetate into fatty acids and/or sterols in the cell. In another embodiment, a modulating agent identified as inhibiting the interaction of XBP-1 and IRE-1 (as determined by, for example, a reporter assay), may be further assayed (e.g., in a secondary screen) for the ability to modulate XBP-1 splicing. An agent identified as decreasing or inhibiting XBP-1 splicing may be further assayed to determine whether the compound further decreases or inhibits XBP-1 protein synthesis. In addition, such an agent identified as decreasing or inhibiting XBP-1 protein synthesis may be further assay to determine whether the compound identified as decreasing or inhibiting XBP-1 protein synthesis also decreases or inhibits the expression of XBP-1 target genes, e.g., lipogenic genes, e.g., DGAT, Scd1, Acc. Furthermore, agents identified in the secondary screens as inhibiting the splicing of XBP-1, XBP-1 protein synthesis and the expression of XBP-1 target genes may be further assayed (e.g., in a tertiary screen) by determining the effect of the agents on hepatic lipogenesis by, for example determining the rate of free fatty acid synthesis and sterol synthesis in a cell-based assay, such as in hepatoma cells.

Furthermore, a modulating agent may be identified in silico and the ability of the agent to modulate XBP-1 activity, IRE-1 activity de novo hepatic lipogeneis, and/or hepatic lipid metabolism, and/or endoplasmic reticulum (ER) stress, and/or the uncoupled protein response, may be further evaluated. For example, a program such as DOCK can be used to identify molecules which will bind to XBP-1 and/or IRE-1 and such molecules may be further evaluated as described herein. See DesJarlias et al. (1988) J. Med. Chem. 31:722; Meng et al. (1992) J. Computer Chem. 13:505; Meng et al. (1993) Proteins 17:266; Shoichet et al. (1993) Science 259:1445.

In another embodiment, a modulating agent may be identified as modulating, e.g., decreasing the amount of XBP-1s protein and/or the ration of spliced to upspliced XBP-1 mRNA and/or protein, and/or XBP-1 and/or IRE-1 activity and the ability of the agent to modulate de-novo hepatic lipogeneis, and/or hepatic lipid metabolism, and/or endoplasmic reticulum (ER) stress, and/or the uncoupled protein response, may be further evaluated.

Moreover, a modulator, identified as described herein (e.g., an enzyme, an antisense nucleic acid molecule, or a specific antibody, or a small molecule) can be used in an animal model to determine the efficacy, toxicity, or side effects of treatment with such a modulator. Alternatively, a modulator identified as described herein can be used in an animal model to determine the mechanism of action of such a modulator.

In another embodiment, it will be understood that similar screening assays can be used to identify compounds that indirectly modulate the activity and/or expression of XBP-1 and/or IRE-1 alpha, e.g., by performing screening assays such as those described above using molecules with which XBP-1 interacts, e.g., molecules that act either upstream or downstream of XBP-1 in a signal transduction pathway.

The cell based and cell free assays of the invention are described in more detail below.

A. Cell Based Assays

The indicator compositions of the invention can be a cell that expresses an XBP-1 and/or IRE-1 alpha protein, for example, a cell that naturally expresses endogenous XBP-1 or, more preferably, a cell that has been engineered to express an exogenous XBP-1 protein by introducing into the cell an expression vector encoding the protein. Alternatively, the indicator composition can be a cell-free composition that includes XBP-1 or a non-XBP-1 protein such as IRE-1, or a composition that includes purified XBP-1 or IRE-1.

Compounds that modulate expression and/or activity of XBP-1 and/or IRE-1 alpha and/or de novo hepatic lipogeneis can be identified using various "read-outs." In one embodiment, during the detecting step, one or more components is transformed (e.g., by labeling).

For example, an indicator cell can be transfected with an XBP-1 expression vector, incubated in the presence and in the absence of a test compound, and the effect of the compound on the expression of the molecule or on a biological response regulated by XBP-1 and/or de novo hepatic lipogenesis can be determined. In one embodiment, unspliced XBP-1 (e.g., capable of being spliced so that the cell will make both forms, or incapable of being spliced so the cell will make only the unspliced form) can be expressed in a cell. In another embodiment, spliced XBP-1 can be expressed in a cell. The biological activities of XBP-1 include activities determined in vivo, or in vitro, according to standard techniques. An XBP-1 activity can be a direct activity, such as an association with an XBP-1-target molecule (e.g., a nucleic acid molecule to which XBP-1 binds such as the transcriptional regulatory region of a chaperone gene and/or a lipogenic gene) or a protein such as the IRE-1 protein. Alternatively, an XBP-1 activity is an indirect activity, such as a cellular signaling activity or alteration in gene expression occurring downstream of the interaction of the XBP-1 protein with an XBP-1 target molecule or a biological effect occurring as a result of the signaling cascade triggered by that interaction. For example, biological activities of XBP-1 described herein include: modulation of de novo hepatic lipogenesis, modulation of ER stress, modulation of the UPR, modulation of cellular differentiation, modulation of the proteasome pathway, modulation of protein folding and transport, modulation of apoptosis, and modulation of a dyslipidemia, e.g., hyperlipidemia, hepatic steatosis, non-alcoholic hepatic steatohepatitis, and steatohepatitis, atherosclerosis.

The biological activities of IRE-1 alpha include activities determined in vivo, or in vitro, according to standard techniques. An IRE-1 alpha activity can be a direct activity, such as an association with an IRE-1 alpha-target molecule (e.g., a nucleic acid molecule to which IRE-1 alpha binds or a protein such as the XBP-1 protein. Alternatively, an IRE-1 alpha activity is an indirect activity, such as a cellular signaling activity or alteration in gene expression occurring downstream of the interaction of the IRE-1 alpha protein with an IRE-1 alpha target molecule or a biological effect occurring as a result of the signaling cascade triggered by that interaction. For example, biological activities of IRE-1 alpha described herein include: modulation of de novo hepatic lipogenesis, modulation of the UPR, modulation of cellular differentiation, modulation of the proteasome pathway, modulation of protein folding and transport, modulation of apoptosis, and modulation of a dyslipidemia, e.g., hyperlipidemia, hepatic steatosis, non-alcoholic hepatic steatohepatitis, and steatohepatitis, atherosclerosis.

To determine whether a test compound modulates de novo hepatic lipogeneis, assays to measuring serum cholesterol and/or triglyceride levels may be used. In one embodiment, the determination of cholesterol is determined by measuring total cholesterol, LDL, HDL, IDL, and/or VLDL. Modulation of de novo hepatic lipogenesis may also be determined by determining the expression of transcription factors that activate genes encoding enzymes involved in glycolysis, fatty acid and cholesterol synthesis, e.g., SREBP-1c and SREBP-2, ChREBP, the rate of free fatty acid and sterol synthesis, etc. Modulation of de novo hepatic lipogenesis may also be determined by determining the expression of a lipogenic gene, e.g., fasn, stearyl coA desaturase, diacyl glycerol acetyltransferase 2, and acetyl coA carboxylase 2 and proprotein convertase subtilisin/kexin type 9 (PCSK9) using art recognized techniques, such as RT-PCR, Northern blot and/or microarray analysis. Additionally, modulation of de novo hepatic lipogenesis may be determined by assaying the direct expression and/or activity of an XBP-1 polypeptide, e.g., by assaying the ability of an XBP-1 polypeptide to bind to a binding partner, e.g., an IRE-1 polypeptide, and/or the promoter of a gene directly regulated by XBP-1, e.g., a lipogenic gene, and/or to activate a reporter gene operably linked to a regulatory element responsive to the XBP-1 polypeptide.

In another embodiment, the invention provides methods for identifying compounds that modulate cellular responses in which XBP-1 and/or IRE-1 is involved. For example, in one embodiment, modulation of the UPR can be determined and used as an indicator of modulation of XBP-1 and/or IRE-1 activity.

To determine whether a test compound modulates XBP-1 and/or IRE-1 protein expression, in vitro transcriptional assays can be performed. In one example of such an assay, the full length XBP-1 gene or promoter and enhancer of XBP-1 operably linked to a reporter gene such as chloramphenicol acetyltransferase (CAT) or luciferase and introduced into host cells. The expression or activity of XBP-1 or the reporter gene can be measured using techniques known in the art. The ability of a test compound to regulate the expression or activity of a molecule in a signal transduction pathway involving XBP-1 can be similarly tested.

As used interchangeably herein, the terms "operably linked" and "operatively linked" are intended to mean that the nucleotide sequence is linked to a regulatory sequence in a manner which allows expression of the nucleotide sequence in a host cell (or by a cell extract).

In another embodiment, modulation of expression of a protein whose expression is regulated by XBP-1 is measured. Regulatory sequences are art-recognized and can be selected to direct expression of the desired protein in an appropriate host cell. The term regulatory sequence is intended to include promoters, enhancers, polyadenylation signals and other expression control elements. Such regulatory sequences are known to those skilled in the art and are described in Goeddel, *Gene Expression Technology: Methods in Enzymology* 185, Academic Press, San Diego, Calif. (1990). It should be understood that the design of the expression vector may depend on such factors as the choice of the host cell to be transfected and/or the type and/or amount of protein desired to be expressed.

Exemplary constructs can include, for example, an XBP-1 target sequence TGGATGACGTGTACA (SEQ ID NO:22) fused to the minimal promoter of the mouse RANTES gene (Clauss et al. Nucleic Acids Research 1996. 24:1855) or the ATF6/XBP-1 target TCGAGACAGGTGCTGACGTGGC-GATTCC (SEQ ID NO:23) and comprising −53/+45 of the cfos promoter (*J. Biol. Chem.* 275:27013) fused to a reporter gene. In one embodiment, multiple copies of the XBP-1 target sequence can be included.

In another embodiment, to determine whether a test compound modulates de novo hepatic lipogeneis and/or XBP-1 activity, a test compound may be assayed by determining the effect of the compound on the ability of XBP-1 to transactivate a reporter gene. For example, a recombinant expression vector comprising a DNA binding region of e.g., a GAL4 protein (e.g., amino acids 1-147), can be operably linked to XBP-1 or a fragment thereof, e.g., the transactivation domain, e.g., amino acid residues 159-371 of spliced human XBP-1 protein, and the effect of a test compound can be assayed by determining whether XBP-1 can transactivate a reporter construct comprising e.g., a regulatory element responsive to the DNA binding region, e.g., a promoter or consensus binding sites(s) of e.g., GAL4 operably linked to a reporter gene, e.g., luciferase.

In another embodiment, a test compound may be assayed by determining the effect of the compound on the ability of glucose to activate a glucose-dependent-promoter operably linked to a repoter gene. For example, as described in the appended examples, high glucose concentrations increase XBP-1 spliced protein. Therefore the ability of a compound to modulate glucose concentration in a cell can be used as an indicator of modulation of de novo hepatic lipogeneis and/or XBP-1 and/or IRE-1 activity. Glucose dependent promoters are known in the art and include, for example, a L-type pyruvate kinase promoter (see, e.g., Chen R, et al. FEBS Lett. 1995 May 29; 365 (2-3):223-6), a sterol regulatory element-binding protein (SREBP)-1 promoter (see, e.g., Alyssa H. HastyDagger et al. J. Biol. Chem., Vol. 275, Issue 40, 31069-31077, Oct. 6, 2000).

A variety of reporter genes are known in the art and are suitable for use in the screening assays of the invention. Examples of suitable reporter genes include those which encode chloramphenicol acetyltransferase, beta-galactosidase, alkaline phosphatase or luciferase. Standard methods for measuring the activity of these gene products are known in the art.

A variety of cell types are suitable for use as an indicator cell in the screening assay. Preferably a cell line is used which expresses low levels of endogenous XBP-1 and/or IRE-1, and is then engineered to express recombinant XBP-1 and/or IRE-1. Cells for use in the subject assays include both eukaryotic and prokaryotic cells. For example, in one embodiment, a cell is a bacterial cell. In another embodiment, a cell is a fungal cell, such as a yeast cell. In another embodiment, a cell is a vertebrate cell, e.g., an avian cell or a mammalian cell (e.g., a murine cell, or a human cell).

In one embodiment, the level of expression of the reporter gene in the indicator cell in the presence of the test compound is higher than the level of expression of the reporter gene in the indicator cell in the absence of the test compound and the test compound is identified as a compound that stimulates the expression of the molecule. In another embodiment, the level of expression of the reporter gene in the indicator cell in the presence of the test compound is lower than the level of expression of the reporter gene in the indicator cell in the absence of the test compound and the test compound is identified as a compound that inhibits the expression of the molecule.

In another embodiment, the level of expression of genes whose expression is regulated by XBP-1 (e.g., lipogenic gene, e.g., fasn, stearyl coA desaturase, diacyl glycerol acetyltransferase 2, acetyl coA carboxylase 2, proprotein convertase subtilisin/kexin type 9 (PCSK9), e.g., chaperone genes, e.g., ERdj4, p58$^{IPK}$, EDEM, PDI-P5, RAMP4, HEDJ, BiP, Armet, DNAJB9, CHOP, or ATF6a) can be measured using standard techniques. The sequences of such genes are known in the art. See, e.g., fasn (gi:41872630, gi:93102408); stearyl coA desaturase (gi:53759150, gi:118130513); diacyl glycerol acetyltransferase 2 (gi:26024196; gi:118129808); gi:134142061, gi:48976024); proprotein convertase subtilisin/kexin type 9 (gi:31317306, gi:23956351); ERdj4 (e.g., NM_012328 [gi:9558754]), p58$^{ipk}$ (e.g., XM_209778 [gi: 2749842] or NM_006260 [gi:24234721] ( ), EDEM (e.g., NM_014674 [gi:7662001], PD1-P5 (e.g., D49489 [gi: 1136742]), RAMP4 (e.g., AF136975 [gi:12239332] ( ), HEDJ (e.g., AF228505 [gi: 7385134]), BiP (e.g., X87949 [gi: 1143491]), ATF6α (e.g., NM_007348 [gi:6671584], XBP-1 (e.g., NM_005080 [gi:14110394]), Armet e.g., NM_006010 [gi:51743920]) and/or DNAJB9 (which encodes mDj7) e.g., (NM_012328 [gi:9558754]), the MHC class II genes (various MHC class II gene sequences are known in the art) and the IL-6 gene (e.g., MN_000600 [gi 10834983]).

In another embodiment, modulation of the UPR or ER stress can also be determined and used as an indicator of modulation of XBP-1 and/or IRE-1 activity. Transcription of genes encoding molecular chaperones and folding enzymes in the endoplasmic reticulum (ER) is induced by accumulation of unfolded proteins in the ER. This intracellular signaling, known as the unfolded protein response (UPR), is mediated by the cis-acting ER stress response element (ERSE) in mammals. In addition to ER chaperones, the mammalian transcription factor CHOP (also called GADD153) is induced by ER stress. XBP-1, when induced by ER stress, is accompanied by the induction of CHOP which is mediated by ERSE. The ERSE consensus sequence is CCAAT-N(9)-CCACG (SEQ ID NO.:27). As the general transcription factor NF-Y (also known as CBF) binds to CCAAT, CCACG is considered to provide specificity in the mammalian UPR.

The processing of ATF6 alpha can also be measured to determine whether an agent modulates ER stress. The basic leucine zipper protein ATF6 alpha isolated as a CCACG-binding the protein is synthesized as a transmembrane protein in the ER, and ER stress-induced proteolysis produces a soluble form of ATF6 alpha that translocates into the nucleus.

In another embodiment, the expression of molecular chaperones such as CHOP, GRP78 or BIP can be measured.

In one embodiment, compounds that modulate de novo hepatic lipogenesis and do not activate ER stress and/or the UPR are identified. In another embodiment, compounds that modulate de novo hepatic lipogenesis and do activate ER stress and/or the UPR are identified.

Modulation of XBP-1 and/or IRE-1 activity (modulation of UPR) can also be measured by, for example, measuring the changes in the endogenous levels of mRNA and the transcription or production of proteins such as ERdj4, p58$^{ipk}$, EDEM, PD1-P5, RAMP4, HEDJ, BiP, ATF6α, XBP-1, Armet and DNAJB9 or folding catalysts using routine ELISA, Northern and Western blotting techniques. In addition, the attenuation of translation associated with the UPR can be measured, e.g., by measuring protein production (Ruegsegger et al. 2001. Cell 107:103). Preferred proteins for detection are expressed on the cell surface or are secreted. In another embodiment, the phosphorylation of IRE-1α, PERK and/or eukaryotic initiation factor 2 (eIF2a) can be measured. In another embodiment, the accumulation of aggregated, misfolded, or damaged proteins in a cell can be monitored (Welch, W. J. 1992 *Physiol. Rev.* 72:1063; Gething and Sambrook. 1992. *Nature.* 355:33; Kuznetsov et al. 1997. J. Biol. Chem. 272:3057).

In one embodiment, modulation of XBP-1 activity can be measured by determining the phosphorylation status of IRE-1, PERK or eIF2α, e.g., using commercially available antibodies that specifically recognize phosphorylated forms of the proteins. Increased phosphorylation of these molecules is observed under conditions of ER stress and the UPR.

In one embodiment differentiation of cells can be used as an indicator of modulation of XBP-1 or a signal transduction pathway involving XBP-1. Cell differentiation can be monitored directly (e.g. by microscopic examination of the cells for monitoring cell differentiation), or indirectly, e.g., by monitoring one or more markers of cell differentiation (e.g. an increase in mRNA for a gene product associated with cell differentiation, or the secretion of a gene product associated with cell differentiation, such as the secretion of a protein (e.g., the secretion of immunoglobulin by differentiated plasma cells) or the expression of a cell surface marker (such as Syndecan expression by plasma cells) Reimold et al. 2001. Nature 412:300). Standard methods for detecting mRNA of interest, such as reverse transcription-polymerase chain reaction (RT-PCR) and Northern blotting, are known in the art. Standard methods for detecting protein secretion in culture supernatants, such as enzyme linked immunosorbent assays (ELISA), are also known in the art. Proteins can also be detected using antibodies, e.g., in an immunoprecipitation reaction or for staining and FACS analysis.

In one embodiment, the ability of a compound to induce terminal B cell differentiation can be determined. As described herein, terminal B cell differentiation can be measured in a variety of ways. Cells can be examined microscopically for the presence of the elaborate ER system characteristic of plasma cells. The secretion of immunoglobulin is also hallmark of plasma cell differentiation. Alternatively, the expression of a cell surface marker can be detected, e.g., surface IgM or Syndecan.

In one embodiment, the ability of a compound to modulate IL-6 production can be determined. Production of IL-6 can be monitored, for example, using Northern or Western blotting. IL-6 can also be detected using an ELISA assay or in a bioassay, e.g., employing cells which are responsive to IL-6 (e.g., cells which proliferate in response to the cytokine or which survive in the presence of the cytokine), such as plasma cells or multiple myeloma cells using standard techniques.

In another embodiment, the ability of a compound to modulate the proteasome pathway of a cell can be determined using any of a number of art-recognized techniques. For example, in one embodiment, the half life of normally short-lived regulatory proteins (e.g., NF-kB, cyclins, oncogenic products or tumor suppressors) can be measured to measure the degradation capacity of the proteasome. In another embodiment, the presentation of antigen in the context of MHC molecules on the surface of cells can be measured (e.g., in an in vitro assay of T cell activation) as proteasome degradation of antigen is important in antigen processing and presentation. In another embodiment, threonine protease activity associated with the proteasome can be measured. Agents that modulate the proteasome pathway will affect the normal degradation of these proteins.

In another embodiment, the modulation of the proteasome pathway can be measured indirectly by measuring the ratio of spliced to unspliced XBP-1 or the ratio of unspliced to spliced XBP-1. Inhibition of the proteasome pathway, e.g., by the inhibitor MG-132, leads to an increase in the level of unspliced XBP-1 as compared to spliced XBP-1.

The techniques for assessing the ratios of unspliced to spliced XBP-1 and spliced to unspliced XBP-1 are routine in the art. For example, the two forms can be distinguished based on their size, e.g., using northern blots or western blots. Because the spliced form of XBP-1 comprises an exon not found in the unspliced form, in another embodiment, antibodies that specifically recognize the spliced or unspliced form of XBP-1 can be developed using techniques well known in the art (Yoshida et al. 2001. Cell. 107:881). In addition, PCR can be used to distinguish spliced from unspliced XBP-1. For example, as described herein, primer sets can be used to amplify XBP-1 where the primers are derived from positions 410 and 580 of murine XBP-1, or corresponding positions in related XBP-1 molecules, in order to amplify the region that encompasses the splice junction. A fragment of 171 base pairs corresponds to unspliced XBP-1 mRNA. An additional band of 145 bp corresponds to the spliced form of XBP-1. The ratio of the different forms of XBP-1 can be determined using these or other art recognized methods.

Compounds that alter the ratio of unspliced to spliced XBP-1 or spliced to unspliced XBP-1 can be useful to modulate de novo hepatic lipogeneis and/or the activity of XBP-1, and the levels of these different forms of XBP-1 can be measured using various techniques described above, or known in the art, and a ratio determined.

In one embodiment, the ability of a compound to modulate protein folding or transport can be determined. The expression of a protein on the surface of a cell or the secretion of a secreted protein can be measured as indicators of protein folding and transport. Protein expression on a cell can be measured, e.g., using FACS analysis, surface iodination, immunoprecipitation from membrane preparations. Protein secretion can be measured, for example, by measuring the level of protein in a supernatant from cultured cells. The production of any secreted protein can be measured in this manner. The protein to be measured can be endogenous or exogenous to the cell. In preferred embodiment, the protein is selected from the group consisting of: a-fetoprotein, a1-antitrypsin, albumin, luciferase and immunoglobulins. The production of proteins can be measured using standard techniques in the art.

In another embodiment, the ability of a compound to modulate apoptosis, e.g., modulate apoptosis by disrupting the UPR, can be determined. In one embodiment, the ability of a compound to modulate apoptosis in a secretory cell or a cell under ER stress is determined. Apoptosis can be measured in the presence or the absence of Fas-mediated signals. In one embodiment, cytochrome C release from mitochondria during cell apoptosis can be detected, e.g., plasma cell apoptosis (as described in, for example, Bossy-Wetzel E. et al. (2000) *Methods in Enzymol.* 322:235-42). Other exemplary assays include: cytofluorometric quantitation of nuclear apoptosis induced in a cell-free system (as described in, for example, Lorenzo H. K. et al. (2000) *Methods in Enzymol.* 322:198-201); apoptotic nuclease assays (as described in, for example, Hughes F. M. (2000) *Methods in Enzymol.* 322:47-62); analysis of apoptotic cells, e.g., apoptotic plasma cells, by flow and laser scanning cytometry (as described in, for example, Darzynkiewicz Z. et al. (2000) *Methods in Enzymol.* 322:18-39); detection of apoptosis by annexin V labeling (as described in, for example, Bossy-Wetzel E. et al. (2000) *Methods in Enzymol.* 322:15-18); transient transfection assays for cell death genes (as described in, for example, Miura M. et al. (2000) *Methods in Enzymol.* 322:480-92); and assays that detect DNA cleavage in apoptotic cells, e.g., apoptotic plasma cells (as described in, for example, Kauffman S. H. et al. (2000) *Methods in Enzymol.* 322:3-15). Apoptosis can also be measured by propidium iodide staining or by TUNEL assay. In another embodiment, the transcription of genes associated with a cell signaling pathway involved in apoptosis (e.g., JNK, caspases) can be detected using standard methods.

In yet another embodiment, the ability of a compound to modulate translocation of spliced XBP-1 to the nucleus can be determined. Translocation of spliced XBP-1 to the nucleus can be measured, e.g., by nuclear translocation assays in which the emission of two or more fluorescently-labeled species is detected simultaneously. For example, the cell nucleus can be labeled with a known fluorophore specific for DNA, such as Hoechst 33342. The spliced XBP-1 protein can be labeled by a variety of methods, including expression as a fusion with GFP or contacting the sample with a fluorescently-labeled antibody specific spliced XBP-1. The amount spliced XBP-1 that translocates to the nucleus can be determined by determining the amount of a first fluorescently-labeled species, i.e., the nucleus, that is distributed in a correlated or anti-correlated manner with respect to a second fluorescently-labeled species, i.e., spliced XBP-1, as described in U.S. Pat. No. 6,400,487, the contents of which are hereby incorporated by reference.

In another embodiment, the ability of XBP-1 and/or IRE-1 to be acted on by an enzyme or to act on a substrate can be measured. For example, in one embodiment, the effect of a compound on the phosphorylation of IRE-1, the ability of IRE-1 to process XBP-1, the ability of PERK to phosphorylate a substrate can be measured using techniques that are known in the art.

The ability of the test compound to modulate XBP-1 and/or IRE-1 binding to a substrate or target molecule can also be determined. Determining the ability of the test compound to modulate XBP-1 (or IRE-1) binding to a target molecule (e.g., a binding partner such as a substrate) can be accomplished, for example, by coupling the target molecule with a radioisotope or enzymatic label such that binding of the target molecule to XBP-1 can be determined by detecting the labeled XBP-1 (or IRE-1) target molecule in a complex. Alternatively, XBP-1 could be coupled with a radioisotope or enzymatic label to monitor the ability of a test compound to modulate XBP-1 binding to a target molecule in a complex. Determining the ability of the test compound to bind to XBP-1 can be accomplished, for example, by coupling the compound with a radioisotope or enzymatic label such that binding of the compound to XBP-1 can be determined by detecting the labeled compound in a complex. For example, targets can be labeled with $^{125}I$, $^{35}S$, $^{14}C$, or $^{3}H$, either directly or indirectly, and the radioisotope detected by direct counting of radio emmission or by scintillation counting. Alternatively, compounds can be labeled, e.g., with, for example, horseradish peroxidase, alkaline phosphatase, or luciferase, and the enzymatic label detected by determination of conversion of an appropriate substrate to product.

It is also within the scope of this invention to determine the ability of a compound to interact with XBP-1 and/or IRE-1 without the labeling of any of the interactants. For example, a microphysiometer can be used to detect the interaction of a compound with XBP-1 without the labeling of either the compound or the XBP-1 (McConnell, H. M. et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and XBP-1.

Exemplary target molecules of XBP-1 include: XBP-1-responsive elements, for example, upstream regulatory regions from genes such as Dgat2, Scd1, and Acc2, PCSK9, or a-1 antitrypsin, a-fetoprotein, HLA DRa, as well as the 21 base pair repeat enhancer of the HTLV-1 LTR. An example of an XBP-1-responsive reporter construct is the HLA DRa-CAT construct described in Ono, S. J. et al. (1991) Proc. Natl. Acad. Sci. USA 88:4309-4312. Other examples can include regulatory regions of the chaperone genes such as members of the family of Glucose Regulated Proteins (GRPs) such as GRP78 (BiP) and GRP94 (endoplasmin), as well as other chaperones such as calreticulin, protein disulfide isomerase, and ERp72. XBP-1 targets are taught, e.g. in Clauss et al. Nucleic Acids Research 1996. 24:1855 also include CRE and TRE sequences.

In another embodiment, a different (i.e., non-XBP-1) molecule acting in a pathway involving XBP-1 that acts upstream (e.g., IRE-1) or downstream (e.g., ATF6a or cochaperone proteins that activate ER resident HspTO proteins, such as p58IPK) of XBP-1 can be included in an indicator composition for use in a screening assay. Compounds identified in a screening assay employing such a molecule would also be useful in modulating XBP-1 activity, albeit indirectly. IRE-1 is one exemplary IRE-1 substrate (e.g., the autophosphorylation of IRE-1). In another embodiment, the endoribonuclease activity of IRE-1 can be measured, e.g., by detecting the splicing of XBP-1 using techniques that are known in the art. The activity of IRE-1 can also be measured by measuring the modulation of biological activity associated with XBP-1.

In another embodiment, a different (i.e., non-XBP-1) molecule acting in a pathway involving XBP-1 that acts upstream (e.g., IRE-1) or downstream (e.g., ATF6α or cochaperone proteins that activate ER resident HspTO proteins, such as $p58^{IPK}$) of XBP-1 can be included in an indicator composition for use in a screening assay.

The cells used in the instant assays can be eukaryotic or prokaryotic in origin. For example, in one embodiment, the cell is a bacterial cell. In another embodiment, the cell is a fungal cell, e.g., a yeast cell. In another embodiment, the cell is a vertebrate cell, e.g., an avian or a mammalian cell. In a preferred embodiment, the cell is a human cell. In another preferred embodiment the cell is a hepatocyte, e.g., a primary hepatocyte. In another embodiment, cells for use in the instant assays is a HeLa cells. In another embodiment, the cell is a hepatoma cell, e.g., a human HepG2 hepatoma cell and/or a McArdle-RH777 rat hepatoma cell.

The cells of the invention can express endogenous XBP-1 and/or IRE-1, or can be engineered to do so. For example, a cell that has been engineered to express the XBP-1 protein and/or a non XBP-1 protein can be produced by introducing into the cell an expression vector encoding the protein.

In one embodiment, to specifically assess the role of agents that modulate the expression and/or activity of unspliced or spliced XBP-1 protein, retroviral gene transduction of cells deficient in XBP-1 with spliced XBP-1 or a form of XBP-1 which cannot be spliced can be performed. For example, a construct in which mutations at in the loop structure of XBP-1 (e.g., positions −1 and +3 in the loop structure of XBP-1) can be generated. Expression of this construct in cells results in production of the unspliced form of XBP-1 only. Using such constructs, the ability of a compound to modulate a particular form of XBP-1 can be detected. In one embodiment, a compound modulates one form of XBP-1, e.g., spliced XBP-1, without modulating the other form, e.g., unspliced XBP-1.

Recombinant expression vectors that can be used for expression of XBP-1, IRE-1, or a molecule in a signal transduction pathway involving XBP-1 (e.g., a protein which acts upstream or downstream of XBP-1) or a molecule in a signal transduction pathway involving XBP-1 in the indicator cell are known in the art. For example, the XBP-1 cDNA is first introduced into a recombinant expression vector using standard molecular biology techniques. A cDNA can be obtained, for example, by amplification using the polymerase chain reaction (PCR) or by screening an appropriate cDNA library. The nucleotide sequences of cDNAs for XBP-1 or a molecule in a signal transduction pathway involving XBP-1 (e.g., human, murine and yeast) are known in the art and can be used for the design of PCR primers that allow for amplification of a cDNA by standard PCR methods or for the design of a hybridization probe that can be used to screen a cDNA library using standard hybridization methods.

Following isolation or amplification of a cDNA molecule encoding, for example, XBP-1, the DNA fragment is introduced into an expression vector. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid molecule in a form suitable for expression of the nucleic acid molecule in a host cell, which means that the recombinant expression vectors include one or more regulatory sequences, selected on the basis of the host cells to be used for expression and the level of expression desired, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell, those which direct expression of the nucleotide sequence only in certain host cells (e.g., tissue-specific regulatory sequences) or those which direct expression of the nucleotide sequence only under certain conditions (e.g., inducible regulatory sequences).

When used in mammalian cells, the expression vector's control functions are often provided by viral regulatory elements. For example, commonly used promoters are derived from polyoma virus, adenovirus, cytomegalovirus and Simian Virus 40. Non-limiting examples of mammalian expression vectors include pCDM8 (Seed, B., (1987) *Nature* 329: 840) and pMT2PC (Kaufman et al. (1987), *EMBO J.* 6:187-195). A variety of mammalian expression vectors carrying different regulatory sequences are commercially available. For constitutive expression of the nucleic acid in a mammalian host cell, a preferred regulatory element is the cytomegalovirus promoter/enhancer. Moreover, inducible regulatory systems for use in mammalian cells are known in the art, for example systems in which gene expression is regulated by heavy metal ions (see e.g., Mayo et al. (1982) *Cell* 29:99-108; Brinster et al. (1982) *Nature* 296:39-42; Searle et al. (1985) *Mol. Cell. Biol.* 5:1480-1489), heat shock (see e.g., Nouer et al. (1991) in *Heat Shock Response*, e.d. Nouer, L., CRC, Boca Raton, Fla., pp 167-220), hormones (see e.g., Lee et al. (1981) *Nature* 294:228-232; Hynes et al. (1981) *Proc. Natl. Acad. Sci. USA* 78:2038-2042; Klock et al. (1987) *Nature* 329:734-736; Israel & Kaufman (1989) *Nucl. Acids Res.* 17:2589-2604; and PCT Publication No. WO 93/23431), FK506-related molecules (see e.g., PCT Publication No. WO 94/18317) or tetracyclines (Gossen, M. and Bujard, H. (1992) *Proc. Natl. Acad. Sci. USA* 89:5547-5551; Gossen, M. et al. (1995) *Science* 268:1766-1769; PCT Publication No. WO 94/29442; and PCT Publication No. WO 96/01313). Still further, many tissue-specific regulatory sequences are known in the art, including the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916) and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

Vector DNA can be introduced into mammalian cells via conventional transfection techniques. As used herein, the various forms of the term "transfection" are intended to refer to a variety of art-recognized techniques for introducing foreign nucleic acid (e.g., DNA) into mammalian host cells, including calcium phosphate co-precipitation, DEAE-dextran-mediated transfection, lipofection, or electroporation. Suitable methods for transfecting host cells can be found in Sambrook et al. (*Molecular Cloning: A Laboratory Manual*, 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on a separate vector from that encoding XBP-1 or, more preferably, on the same vector. Cells stably transfected with the introduced nucleic acid can be identified by drug selection (e.g., cells that have incorporated the selectable marker gene will survive, while the other cells die).

In one embodiment, within the expression vector coding sequences are operatively linked to regulatory sequences that allow for constitutive expression of the molecule in the indicator cell (e.g., viral regulatory sequences, such as a cytomegalovirus promoter/enhancer, can be used). Use of a recombinant expression vector that allows for constitutive expression of, for example, XBP-1 and/or IRE-1 in the indicator cell is preferred for identification of compounds that enhance or inhibit the activity of the molecule. In an alternative embodiment, within the expression vector the coding sequences are operatively linked to regulatory sequences of the endogenous gene for XBP-1 (i.e., the promoter regulatory region derived from the endogenous gene). Use of a recombinant expression vector in which expression is controlled by the endogenous regulatory sequences is preferred for identification of compounds that enhance or inhibit the transcriptional expression of the molecule.

C. Cell-free Assays

In another embodiment, the indicator composition is a cell free composition. XBP-1 and/or IRE-1 protein expressed by recombinant methods in a host cells or culture medium can be isolated from the host cells, or cell culture medium using standard methods for protein purification. For example, ion-exchange chromatography, gel filtration chromatography, ultrafiltration, electrophoresis, and immunoaffinity purification with antibodies can be used to produce a purified or semi-purified protein that can be used in a cell free composition. Alternatively, a lysate or an extract of cells expressing the protein of interest can be prepared for use as cell-free composition.

In one embodiment, compounds that specifically modulate XBP-1 and/or IRE-1 activity are identified based on their ability to modulate the interaction of XBP-1 and/or IRE-1 with a target molecule to which XBP-1 binds. The target molecule can be a DNA molecule, e.g., an XBP-1-responsive element, such as the regulatory region of a chaperone gene, lipogenic gene) or a protein molecule. Suitable assays are known in the art that allow for the detection of protein-protein interactions (e.g., immunoprecipitations, two-hybrid assays and the like) or that allow for the detection of interactions between a DNA binding protein with a target DNA sequence (e.g., electrophoretic mobility shift assays, DNAse I footprinting assays, chromatin immunoprecipitations assays and the like). By performing such assays in the presence and absence of test compounds, these assays can be used to identify compounds that modulate (e.g., inhibit or enhance) the interaction of XBP-1 and/or IRE-1 with a target molecule.

In one embodiment, the amount of binding of XBP-1 and/or IRE-1 to the target molecule in the presence of the test compound is greater than the amount of binding of XBP-1 and/or IRE-1 to the target molecule in the absence of the test compound, in which case the test compound is identified as a compound that enhances binding of XBP-1 (or IRE-1) to a target. In another embodiment, the amount of binding of the XBP-1 (or IRE-1) to the target molecule in the presence of the test compound is less than the amount of binding of the XBP-1 (or IRE-1) to the target molecule in the absence of the test compound, in which case the test compound is identified as a compound that inhibits binding of XBP-1 (or IRE-1) to the target.

Binding of the test compound to XBP-1 and/or IRE-1 can be determined either directly or indirectly as described above. Determining the ability of XBP-1 (or IRE-1) protein to bind to a test compound can also be accomplished using a technology such as real-time Biomolecular Interaction Analysis (BIA) (Sjolander, S. and Urbaniczky, C. (1991) *Anal. Chem.* 63:2338-2345; Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In the methods of the invention for identifying test compounds that modulate an interaction between XBP-1 (or IRE-1) protein and a target molecule, the complete XBP-1 (or IRE-1) protein can be used in the method, or, alternatively, only portions of the protein can be used. For example, an isolated XBP-1 b-ZIP structure (or a larger subregion of XBP-1 that includes the b-ZIP structure) can be used. In another example, a form of XBP-1 comprising the splice junction can be used (e.g., a portion including from about nucleotide 506 to about nucleotide 532). The degree of interaction between the protein and the target molecule can be determined, for example, by labeling one of the proteins with a detectable substance (e.g., a radiolabel), isolating the non-labeled protein and quantitating the amount of detectable substance that has become associated with the non-labeled protein. The assay can be used to identify test compounds that either stimulate or inhibit the interaction between the XBP-1 (or IRE-1) protein and a target molecule. A test compound that stimulates the interaction between the protein and a target molecule is identified based upon its ability to increase the degree of interaction between, e.g., spliced XBP-1 and a target molecule as compared to the degree of interaction in the absence of the test compound and such a compound would be expected to increase the activity of spliced XBP-1 in the cell. A test compound that inhibits the interaction between the protein and a target molecule is identified based upon its ability to decrease the degree of interaction between the protein and a target molecule as compared to the degree of interaction in the absence of the compound and such a compound would be expected to decrease spliced XBP-1 activity.

In one embodiment of the above assay methods of the present invention, it may be desirable to immobilize either XBP-1 (and/or IRE-1) or a respective target molecule for example, to facilitate separation of complexed from uncomplexed forms of one or both of the proteins, or to accommodate automation of the assay. Binding of a test compound to, for example, an XBP-1 protein, or interaction of an XBP-1 protein with a target molecule in the presence and absence of a test compound, can be accomplished in any vessel suitable for containing the reactants. Examples of such vessels include microtitre plates, test tubes, and micro-centrifuge tubes. In one embodiment, a fusion protein can be provided in which a domain that allows one or both of the proteins to be bound to a matrix is added to one or more of the molecules. For example, glutathione-S-transferase fusion proteins or glutathione-S-transferase/target fusion proteins can be adsorbed onto glutathione sepharose-beads (Sigma Chemical, St. Louis, Mo.) or glutathione derivatized microtitre plates, which are then combined with the test compound or the test compound and either the non-adsorbed target protein or XBP-1 (or IRE-1) protein, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of binding or activity determined using standard techniques.

Other techniques for immobilizing proteins on matrices can also be used in the screening assays of the invention. For example, either an XBP-1 protein or a molecule in a signal transduction pathway involving XBP-1, or a target molecule can be immobilized utilizing conjugation of biotin and streptavidin. Biotinylated protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies which are reactive with protein or target molecules but which do not interfere with binding of the protein to its target molecule can be derivatized to the wells of the plate, and unbound target or XBP-1 (or IRE-1) protein is trapped in the wells by antibody conjugation. Methods for detecting such complexes, in addition to those described above for the GST-immobilized complexes, include immunodetection of complexes using antibodies reactive with XBP-1 or a molecule in a signal transduction pathway involving XBP-1 or target molecule, as well as enzyme-linked assays which rely on detecting an enzymatic activity associated with the XBP-1 or IRE-1, protein or target molecule.

In yet another aspect of the invention, the XBP-1 protein (or IRE-1) or fragments thereof can be used as "bait proteins" e.g., in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with XBP-1 ("binding proteins" or "bp") and are involved in XBP-1 activity. Such XBP-1-binding proteins are also likely to be involved in the propagation of signals by the XBP-1 proteins or XBP-1 targets such as, for example, downstream elements of an XBP-1-mediated signaling pathway. Alternatively, such XBP-1-binding proteins can be XBP-1 inhibitors.

The two-hybrid system is based on the modular nature of most transcription factors, which consist of separable DNA-binding and activation domains. Briefly, the assay utilizes two different DNA constructs. In one construct, the gene that codes for an XBP-1 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an XBP-1 dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the XBP-1 protein or a molecule in a signal transduction pathway involving XBP-1.

C. Assays Using Knock-Down or Knock-Out Cells

In another embodiment, the invention provides methods for identifying compounds that modulate a biological effect of XBP-1 or a molecule in a signal transduction pathway involving XBP-1 using cells deficient in XBP-1 (or e.g., IRE-1). Cells deficient in XBP-1 or a molecule in a signal transduction pathway involving XBP-1 or in which XBP-1 or a molecule in a signal transduction pathway involving XBP-1 is knocked down can be used to identify agents that modulate a biological response regulated by XBP-1 by means other than modulating XBP-1 itself (i.e., compounds that "rescue" the XBP-1 deficient phenotype). Alternatively, a "conditional knock-out" system, in which the gene is rendered non-functional in a conditional manner, can be used to create deficient cells for use in screening assays. For example, a tetracycline-regulated system for conditional disruption of a gene as described in WO 94/29442 and U.S. Pat. No. 5,650,298 can be used to create cells, or animals from which cells can be isolated, be rendered deficient in XBP-1 (or a molecule in a signal transduction pathway involving XBP-1 e.g., IRE-1) in a controlled manner through modulation of the tetracycline concentration in contact with the cells.

In the screening method, cells deficient in XBP-1 or a molecule in a signal transduction pathway involving XBP-1 can be contacted with a test compound and a biological response regulated by XBP-1 or a molecule in a signal transduction pathway involving XBP-1 can be monitored. Modulation of the response in cells deficient in XBP-1 or a molecule in a signal transduction pathway involving XBP-1 (as compared to an appropriate control such as, for example, untreated cells or cells treated with a control agent) identifies a test compound as a modulator of the XBP-1 (or e.g., IRE-1) regulated response. In another embodiment, to specifically assess the role of agents that modulate unspliced or spliced XBP-1 protein, retroviral gene transduction of cells deficient in XBP-1, to express spliced XBP-1 or a form of XBP-1 which cannot be spliced can be performed. For example, a construct in which mutations at in the loop structure of XBP-1 (e.g., positions −1 and +3 in the loop structure of XBP-1) can be generated. Expression of this construct in cells results in production of the unspliced form of XBP-1 only. Using such constructs, the ability of a compound to modulate a particular form of XBP-1 can be detected. For example, in one embodiment, a compound modulates one form of XBP-1 without modulating the other form.

In one embodiment, the test compound is administered directly to a non-human knock out animal, preferably a mouse (e.g., a mouse in which the XBP gene or a gene in a signal transduction pathway involving XBP-1 is conditionally disrupted by means described above, or a chimeric mouse in which the lymphoid organs are deficient in XBP-1 as described above), to identify a test compound that modulates the in vivo responses of cells deficient in XBP-1 (or e.g., IRE-1). In another embodiment, cells deficient in XBP-1 (or e.g., IRE-1) are isolated from the non-human XBP-1 or a molecule in a signal transduction pathway involving XBP-1 deficient animal, and contacted with the test compound ex vivo to identify a test compound that modulates a response regulated by XBP-1 (or e.g., IRE-1) in the cells Cells deficient in XBP-1 or a molecule in a signal transduction pathway involving XBP-1 can be obtained from a non-human animals created to be deficient in XBP-1 or a molecule in a signal transduction pathway involving XBP-1 Preferred non-human animals include monkeys, dogs, cats, mice, rats, cows, horses, goats and sheep. In preferred embodiments, the deficient animal is a mouse. Mice deficient in XBP-1 or a molecule in a signal transduction pathway involving XBP-1 can be made using methods known in the art. Non-human animals deficient in a particular gene product typically are created by homologous recombination. Briefly, a vector is prepared which contains at least a portion of the gene into which a deletion, addition or substitution has been introduced to thereby alter, e.g., functionally disrupt, the endogenous XBP-1 (or e.g., IRE-1 gene). The gene preferably is a mouse gene. For example, a mouse XBP-1 gene can be isolated from a mouse genomic DNA library using the mouse XBP-1 cDNA as a probe. The mouse XBP-1 gene then can be used to construct a homologous recombination vector suitable for modulating an endogenous XBP-1 gene in the mouse genome. In a preferred embodiment, the vector is designed such that, upon homologous recombination, the endogenous gene is functionally disrupted (i.e., no longer encodes a functional protein; also referred to as a "knock out" vector).

Alternatively, the vector can be designed such that, upon homologous recombination, the endogenous gene is mutated or otherwise altered but still encodes functional protein (e.g., the upstream regulatory region can be altered to thereby alter the expression of the endogenous XBP-1 protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced gene has homologously recombined with the endogenous gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, retroviral transduction of donor bone marrow cells from both wild type and null mice can be performed, e.g., with the XBP-1 unspliced, DN or spliced constructs to reconstitute irradiated RAG recipients. This will result in the production of mice whose lymphoid cells express only unspliced, or only spliced XBP-1 protein, or which express a dominant negative version of XBP-1. Cells from these mice can then be tested for compounds that modulate a biological response regulated by XBP-1.

In another embodiment, XBP-1 may be temporally deleted to, for example, circumvent embryonic lethality. For example, as described herein and in C. Hetz et al. (2008) *Proc Natl Acad Sci USA* In Press, XBP-1 was specifically deleted using XBP-1$^{flox}$ mice bred with Mx1-cre mice (R. Kuhn, et al. (2995) *Science* 269, 1427) to generate XBP-1$^{f/f}$; Mx1-cre mice, and subsequently treated with poly(I:C) to induce cre expression and excision of the floxed exon 2 of XBP-1.

In another embodiment, a molecule which mediates RNAi, e.g., double stranded RNA can be used to knock down expression of XBP-1 or a molecule in a signal transduction pathway involving XBP-1. For example, an XBP-1-specific RNAi vector has been constructed by inserting two complementary oligonucleotides 5'-GGGATTCATGAATGGCCCTTA-3' (SEQ ID NO.:24) into the pBS/U6 vector as described (Sui et al. 2002 *Proc Natl Acad Sci USA* 99: 5515-5520).

In one embodiment of the screening assay, compounds tested for their ability to modulate a biological response regulated by XBP-1 or a molecule in a signal transduction pathway involving XBP-1 are contacted with deficient cells by administering the test compound to a non-human deficient animal in vivo and evaluating the effect of the test compound on the response in the animal.

The test compound can be administered to a non-knock out animal as a pharmaceutical composition. Such compositions typically comprise the test compound and a pharmaceutically acceptable carrier. As used herein the term "pharmaceutically acceptable carrier" includes any and all solvents, dispersion media, coatings, antibacterial and antifungal compounds, isotonic and absorption delaying compounds, and the like, compatible with pharmaceutical administration. The use of such media and compounds for pharmaceutically active substances is well known in the art. Except insofar as any conventional media or compound is incompatible with the active compound, use thereof in the compositions is contemplated. Supplementary active compounds can also be incorporated into the compositions. Pharmaceutical compositions are described in more detail below.

In another embodiment, compounds that modulate a biological response regulated by XBP-1 or a signal transduction pathway involving XBP-1 are identified by contacting cells deficient in XBP-1 ex vivo with one or more test compounds, and determining the effect of the test compound on a read-out. In one embodiment, XBP-1 deficient cells contacted with a test compound ex vivo can be re-administered to a subject.

For practicing the screening method ex vivo, cells deficient, e.g., in XBP-1, IRE-1, can be isolated from a non-human XBP-1, IRE-1, deficient animal or embryo by standard methods and incubated (i.e., cultured) in vitro with a test compound. Cells (e.g., B cells, hepatocytes, MEFs) can be isolated from e.g., XBP-1, IRE-1 deficient animals by standard techniques.

In another embodiment, cells deficient in more than one member of a signal transduction pathway involving XBP-1 can be used in the subject assays.

Following contact of the deficient cells with a test compound (either ex vivo or in vivo), the effect of the test compound on the biological response regulated by XBP-1 or a molecule in a signal transduction pathway involving XBP-1 can be determined by any one of a variety of suitable methods, such as those set forth herein, e.g., including light microscopic analysis of the cells, histochemical analysis of the cells, production of proteins, induction of certain genes, e.g., chaperone genes, lipogenic genes.

D. Test Compounds

A variety of test compounds can be evaluated using the screening assays described herein. The term "test compound" includes any reagent or test agent which is employed in the assays of the invention and assayed for its ability to influence the expression and/or activity of XBP-1 and/or IRE-1. More than one compound, e.g., a plurality of compounds, can be tested at the same time for their ability to modulate the expression and/or activity of, e.g., XBP-1, in a screening assay. The term "screening assay" preferably refers to assays which test the ability of a plurality of compounds to influence the read-out of choice rather than to tests which test the ability of one compound to influence a readout. Preferably, the subject assays identify compounds not previously known to have the effect that is being screened for. In one embodiment, high throughput screening can be used to assay for the activity of a compound.

In certain embodiments, the compounds to be tested can be derived from libraries (i.e., are members of a library of compounds). While the use of libraries of peptides is well established in the art, new techniques have been developed which have allowed the production of mixtures of other compounds, such as benzodiazepines (Bunin et al. (1992). *J. Am. Chem. Soc.* 114:10987; DeWitt et al. (1993). *Proc. Natl. Acad. Sci. USA* 90:6909) peptoids (Zuckermann. (1994). *J. Med. Chem.* 37:2678) oligocarbamates (Cho et al. (1993). *Science.* 261: 1303), and hydantoins (DeWitt et al. supra). An approach for the synthesis of molecular libraries of small organic molecules with a diversity of 104-105 as been described (Carell et al. (1994). *Angew. Chem. Int. Ed. Engl.* 33:2059; Carell et al. (1994) *Angew. Chem. Int. Ed. Engl.* 33:2061-).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145). Other exemplary methods for the synthesis of molecular libraries can be found in the art, for example in: Erb et al. (1994). *Proc. Natl. Acad. Sci. USA* 91:11422; Horwell et al. (1996) *Immunopharmacology* 33:68-; and in Gallop et al. (1994); *J. Med. Chem.* 37:1233.

Libraries of compounds can be presented in solution (e.g., Houghten (1992) *Biotechniques* 13:412-421), or on beads (Lam (1991)*Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310). In still another embodiment, the combinatorial polypeptides are produced from a cDNA library.

Exemplary compounds which can be screened for activity include, but are not limited to, peptides, nucleic acids, carbohydrates, small organic molecules, and natural product extract libraries.

Candidate/test compounds include, for example, 1) peptides such as soluble peptides, including Ig-tailed fusion peptides and members of random peptide libraries (see, e.g., Lam, K. S. et al. (1991) *Nature* 354:82-84; Houghten, R. et al. (1991) *Nature* 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) *Cell* 72:767-778); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); 4) small organic and inorganic molecules (e.g., molecules obtained from combinatorial and natural product libraries); 5) enzymes (e.g., endoribonucleases, hydrolases, nucleases, proteases, synthetases, isomerases, polymerases, kinases, phosphatases, oxido-reductases and ATPases), and 6) mutant forms of XBP-1 (or e.g., IRE-1 molecules, e.g., dominant negative mutant forms of the molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

Compounds identified in the subject screening assays can be used in methods of modulating one or more of the biological responses regulated by XBP-1. It will be understood that it may be desirable to formulate such compound(s) as pharmaceutical compositions (described supra) prior to contacting them with cells.

Once a test compound is identified that directly or indirectly modulates, e.g., XBP-1 expression or activity, by one of the variety of methods described hereinbefore, the selected test compound (or "compound of interest") can then be further evaluated for its effect on cells, for example by contacting the compound of interest with cells either in vivo (e.g., by administering the compound of interest to a subject) or ex vivo (e.g., by isolating cells from the subject and contacting the isolated cells with the compound of interest or, alternatively, by contacting the compound of interest with a cell line) and determining the effect of the compound of interest on the cells, as compared to an appropriate control (such as untreated cells or cells treated with a control compound, or carrier, that does not modulate the biological response).

E. Computer Assisted Design of Modulators of XBP-1 and/or IRE-1

Computer-based analysis of a protein with a known structure can also be used to identify molecules which will bind to the protein. Such methods rank molecules based on their shape complementary to a receptor site. For example, using a 3-D database, a program such as DOCK can be used to identify molecules which will bind to XBP-1 or a molecule in a signal transduction pathway involving XBP-1. See DesJarlias et al. (1988) *J. Med. Chem.* 31:722; Meng et al. (1992) *J. Computer Chem.* 13:505; Meng et al. (1993) *Proteins* 17:266; Shoichet et al. (1993) *Science* 259:1445. In addition, the electronic complementarity of a molecule to a targeted protein can also be analyzed to identify molecules which bind to the target. This can be determined using, for example, a molecular mechanics force field as described in Meng et al. (1992) *J. Computer Chem.* 13:505 and Meng et al. (1993) *Proteins* 17:266. Other programs which can be used include CLIX which uses a GRID force field in docking of putative ligands. See Lawrence et al. (1992) *Proteins* 12:31; Goodford et al. (1985) *J. Med. Chem.* 28:849; Boobbyer et al. (1989) *J. Med. Chem.* 32:1083.

The instant invention also pertains to compounds identified in the subject screening assays.

V. Kits of the Invention

Another aspect of the invention pertains to kits for carrying out the screening assays or modulatory methods of the invention. For example, a kit for carrying out a screening assay of the invention can include an indicator composition comprising XBP-1 and/or IRE-1, means for measuring a readout (e.g., protein secretion) and instructions for using the kit to identify modulators of biological effects of XBP-1. In another embodiment, a kit for carrying out a screening assay of the invention can include cells deficient in XBP-1 or a molecule in a signal transduction pathway involving XBP-1, means for measuring the readout and instructions for using the kit to identify modulators of a biological effect of XBP-1.

In another embodiment, the invention provides a kit for carrying out a modulatory method of the invention. The kit can include, for example, a modulatory agent of the invention (e.g., XBP-1 inhibitory or stimulatory agent) in a suitable carrier and packaged in a suitable container with instructions for use of the modulator to modulate a biological effect of XBP-1.

This invention is further illustrated by the following examples which should not be construed as limiting. The contents of all references, patents and published patent applications cited throughout this application are hereby incorporated by reference.

EXAMPLES

The following materials and methods were used in the Examples.

Generation of Mice Lacking XBP-1 in the Liver (XBP-1Δ)

XBP-1$^{flox}$ mice that have two loxP sites in intron 2 and 3 are described elsewhere (C. Hetz et al. (2008) *Proc Natl Acad Sci USA* In Press). XBP-1$^{flox}$ mice were bred with Mx1-cre mice (R. Kuhn, et al. (2995) Science 269, 1427) to generate XBP-1$^{f/f}$; Mx1-cre mice. 5-6 weeks old mice were intraperitoneally injected 1 or 3 times with 250 μg of poly(I:C) each time with 2 days intervals to induce the cre expression. Mice were used for experiments at least 2-3 weeks after the final poly(I:C) injection. Mice backcrossed for more than five generations onto C57BL/6 background were used in most experiments, except for those in Table 1, FIGS. 2a and 2b, where mice on a SV129 and C57BL/6 mixed background were used.

Tunicamycin Injections

Tunicamycin diluted in 150 mM dextrose at 100 μg/ml was intraperitoneally injected at 1 g/Kg body weight.

Diet Studies

Mice were housed in a specific pathogen free facility at the Harvard School of Public Health on a 12 h light/dark cycle and had free access to standard rodent chow diet or 60% fructose diet (Harlan Teklad TD.8820).

Northern Blot and Real Time PCR Analysis.

Total RNA isolation, Northern blot and real time PCR analysis were performed as described previously (A. H. Lee, et al. (2003) *Mol Cell Biol* 23, 7448; A. H. Lee, et al. (2005) *Embo J* 24, 4368). Primers for the real time PCR analysis are described in TABLE 3 or elsewhere (A. H. Lee; et al. (2005) *Embo J* 24, 4368). Probes for Northern blot were generated with PCR amplified cDNA pieces for each gene by using primers shown in TABLE 4. IRE-1 splicing of XBP-1 mRNA was measured by RT-PCR analysis as described previously (A. H. Lee, et al. (2003) *Proc Natl Acad Sci USA* 100, 9946).

Nuclear Extracts and Western Blot

Nuclear extracts from the liver were prepared as described with modifications (M. Hattori, A et al. (1990) *DNA Cell Biol* 9, 777). Briefly, pieces of the liver (~0.5 g) were homogenized in 3 ml homogenization buffer (10 mM Hepes, pH 7.9, 10 mM KCl, 0.1 mM EDTA, 0.74 mM Spermidine, 1 mM DTT, 0.3 M sucrose, protease inhibitor mix (Roche)) with Polytron, mixed with 6 ml of the cushion buffer (10 mM Hepes, pH 7.9, 0.1 mM EDTA, 0.74 mM Spermidine, 1 mM DTT, 2.2 M sucrose, 2 µg/ml aprotinin, 2 µg/ml leupeptin) and then overlayed on 2 ml cushion buffer. Nuclei were precipitated by 60 min centrifugation at 77,000 g, and lysed in RIPA buffer (50 mM Tris pH 7.4, 150 mM NaCl, 0.1 mM EDTA, 1% Triton X-100, 1% sodium deoxycholate, 0.1% SDS). Lysates were briefly sonicated and cleared by centrifugation for 5 min. Nuclear extracts from cultured hepatocytes were prepared as described previously (E. Schreiber, et al. (1989) *Nucleic Acids Res* 17, 6419). Western blot analyses on nuclear extracts were performed with rabbit polyclonal anti-XBP-1, ATF6a, Sp1 (Santa cruz), SREBP-1 and SREBP-2 antibodies. IRE-1 alpha proteins in the liver were detected by Western blot with rabbit polyclonal anti-IRE-1 alpha antibody following immunoprecipitation with the same antibody from 500 µg of the liver lysates prepared in a lysis buffer (1% NP-40, 30 mM Tris, pH 7.5, 150 mM NaCl, 50 mM sodium fluoride, 10 mM sodium orthophosphate, 1 µg/ml aprotinin, 2 µg/ml leupeptin). In some experiments, immunoprecipitation products were resuspended in a buffer for λ phosphatase (NEB) treatment for 30 min before Western blot analysis. Whole liver lysates prepared in 1% NP-40 lysis buffer were used for the western blot of total and phospho-JNK with specific antibodies (Cell signaling). ApoB-100 protein species in the plasma were detected by using monoclonal ApoB-100 antibody (A. T. Nguyen et al. (2006) *Biochim Biophys Acta* 1761, 182).

Histology and TEM

Pieces of the liver fixed in 10% neutral buffered formalin were embedded in paraffin and stained with hematoxylin and eosin. Frozen sections were stained with oil Red O. TEM was performed as described previously (A. H. Lee, et al. (2005) *Embo J* 24, 4368).

Blood Chemistries and Lipid Analysis

Plasma triglyceride and cholesterol were measured by using commercial kits (Sigma). Blood glucose concentrations were measured by using ACCU-Check glucometer (Roche). Serum ALT and albumin levels were measured by using commercial reagents (Bioquant). For VLDL secretion assays, mice were fasted for 4 hrs, and retro-orbitally injected with 0.5 mg/Kg Tyloxapol (Sigma). Tail bleedings were performed at indicated time points for plasma triglyceride measurements. The distribution of cholesterol in plasma was determined by fast performance liquid chromatography (FPLC) separation followed by cholesterol assays of each fraction. Lipid composition in the liver was determined by TrueMass Lipomics analysis (Lipomics) after pooling liver pieces from 4 mice/group.

Mouse Primary Hepatocytes and Pulse-chase Experiments

Mouse primary hepatocytes were isolated by perfusion followed by collagenase digestion by using commercial reagents (Invitrogen). Cells were resuspended in M199 media supplemented with 5% fetal bovine serum, plated at a density of $9 \times 10^5$ cells per 60 mm positively-charged Primaria® dish (Becton Dickinson) and allowed to attach for ~6 hrs. Cells were washed and cultured for 30 min in methionine and cysteine-free DMEM supplemented with 10% dialysed fetal bovine serum, and then labeled with the same media containing 100 µCi/ml $^{35}$S-methionine/cysteine for 60 min. Media was changed with DMEM containing both methionine and cysteine and 10% fetal bovine serum. Media and cells were harvested at the indicated times for immunoprecipitation. Cells were lysed in RIPA buffer. ApoB protein species were immunoprecipitated with goat anti-ApoB antibody (Chemicon), washed three times with lysis buffer, and run on 6% SDS-PAGE gels. Gels were treated with Amplify® (Amersham), dried and exposed to x-ray film.

Recombinant Adenoviruses

XBP-1s cDNA was cloned into pAdTRACK-cmv shuttle vector (T. C. He et al. (1998) *Proc Natl Acad Sci USA* 95, 2509). Recombinant adenoviral DNA was generated by homologous recombination by transforming BJ5183-AD1 competent cells (Stratagene) with the shuttle vector. Adenoviral DNAs were linearized using PacI and then transfected into HEK-293 cells with Lipofectamine 2000 reagents (Invitrogen) to produce recombinant viruses. Infected cells were lysed by three cycles of freezing and thawing and then centrifuged. Viral titer was determined by infecting HEK-293 cells with serially diluted viral stock and counting GFP positive cells 24 hrs after infection. Primary hepatocytes were infected with recombinant adenoviruses at 2 or 10 pfu per cell. Total RNAs were prepared from virus-infected hepatocytes 24 hrs later by using Trizol reagent (Invitrogen).

Chromatin Immunoprecipitation (CHIP) Assay

Nuclei were isolated from ~0.5 g of liver tissue by centrifugation on 2.2 M sucrose cushion as described above. CHIP assays were performed as described previously (J. D. Nelson, et al. (2006) *Nat Protoc* 1, 179) with some modifications. Briefly, purified nuclei were resuspended in 1 ml PBS containing 1.4% formaldehyde and incubated at room temperature for 15 min to cross-link protein to DNA. Cross-linked nuclei were washed twice with PBS and once with IP buffer (1% NP-40, 30 mM Tris, pH 7.5, 150 mM NaCl, 1 µg/ml aprotinin, 2 µg/ml leupeptin). Lysates were sonicated and immunoprecipitated with rabbit polyclonal anti-XBP-1 antibody or control rabbit serum. Immune complexes were precipitated by using protein A-agarose (Roche) and washed 5 times with IP buffer. Immunoprecipitated genomic. DNA was eluted by boiling for 10 min in 10% Chlex 100 beads (Bio-Rad) and then used for real time PCR with primers designed to amplify proximal promoter regions (Supplementary Table 4). Acc2 promoter II was predicted by aligning the mouse genomic DNA sequences with the reported human Acc2 promoter sequences (S. Y. Oh et al. (2003) *J Biol Chem* 278, 28410).

Example 1

Generation of Mice Deficient in Liver XBP-1

Figure 6:
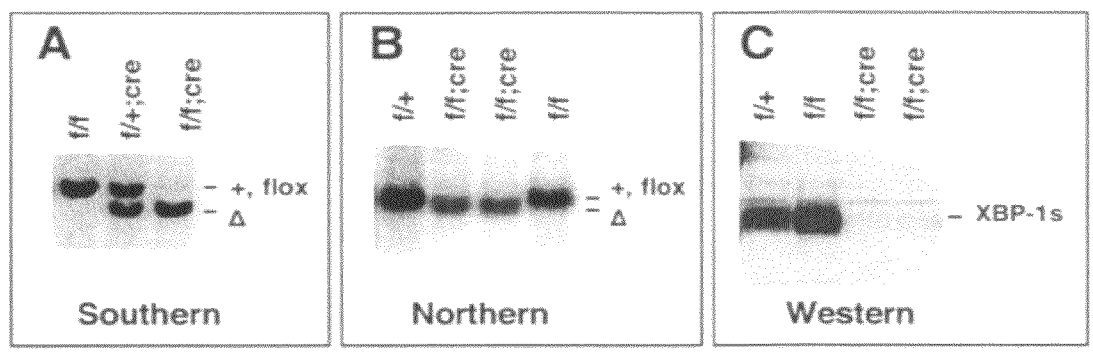
FIGS. 6A-6C depicts Southern blot analysis of genomic DNA from liver. XBP-1$^{f/f}$, XBP-1$^{f/+}$; Mx1-cre and XBP-1$^{f/f}$; Mx1-cre mice were injected three times with poly(I:C) and genomic DNA were prepared two weeks later. Bands representing the floxed, WT (+), and deleted allele of the XBP-1 gene by cre-mediated recombination are indicated. (B) Northern blot analysis of the RNA from mice with indicated genotypes. Total liver RNAs were prepared two weeks after poly(I:C) injections. The mutant XBP-1 mRNA from the XBP-1Δ Knock-out) allele is smaller than the WT due to the lack of the floxed exon 2 sequences (97 nt). (C) Liver nuclear extracts were prepared from poly(I:C) injected mice as in (B) and subjected to a western blot analysis with anti-XBP-1 antibody.

To investigate the role of XBP-1 in postnatal hepatic function, XBP-1$^{flox}$ mice harboring loxP sites in the first and second intron of the XBP-1 gene were used (C. Hetz et al. (2008) *Proc Natl Acad Sci USA* In Press). To circumvent the embryonic lethality caused by XBP-1 deletion in liver, XBP-1$^{flox}$ mice were crossed with Mx1-cre mice that express cre recombinase in an interferon dependent manner. Cre recombinase-mediated recombination removes exon 2, to induce alternative splicing between exon 1 and 3 of XBP-1 mRNA, resulting in a reading frame shift and introduction of a translational termination codon (21). Intraperitoneal injection of poly(I:C) efficiently deleted the floxed exon 2 of the XBP-1 gene in the liver as determined by Southern blot (FIG. S1a). The mutant XBP-1 mRNA produced from XBP-1$^{f/f}$; Mx1-cre (XBP-1Δ, XBP-1 knock-out) mice was slightly smaller than the WT mRNA due to the lack of exon 2, as confirmed by Northern blot and RT-PCR followed by DNA sequencing analysis of the mutant XBP-1 transcript (FIG. 6b). Lack of XBP-1 protein in XBP-1Δ liver was also confirmed by Western blot (FIG. 6c).

Example 2

Role of XBP-1 in Hepatic Secretory Function

Figure 1C:
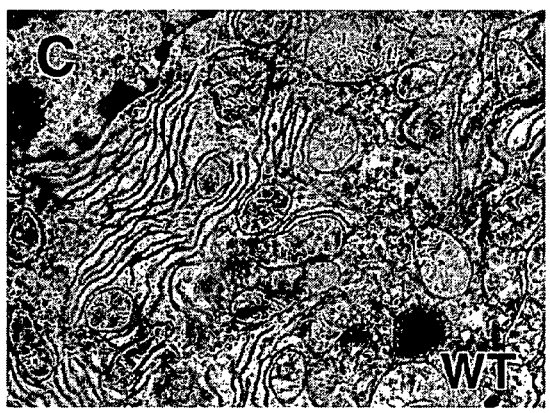
Figure 1D:
Figure 1E:
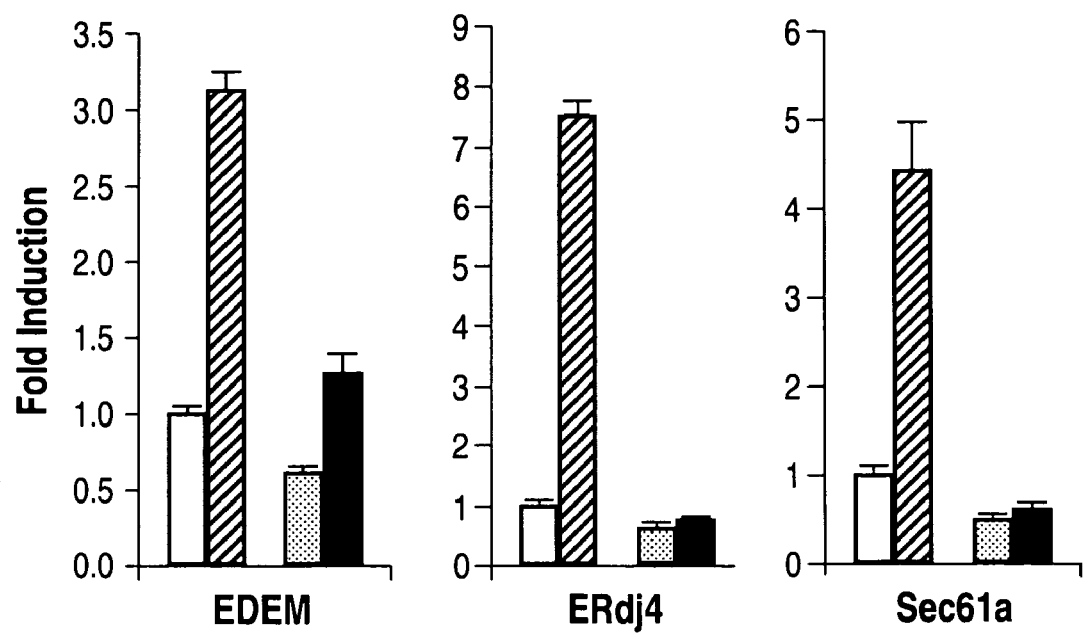
Figure 1E:
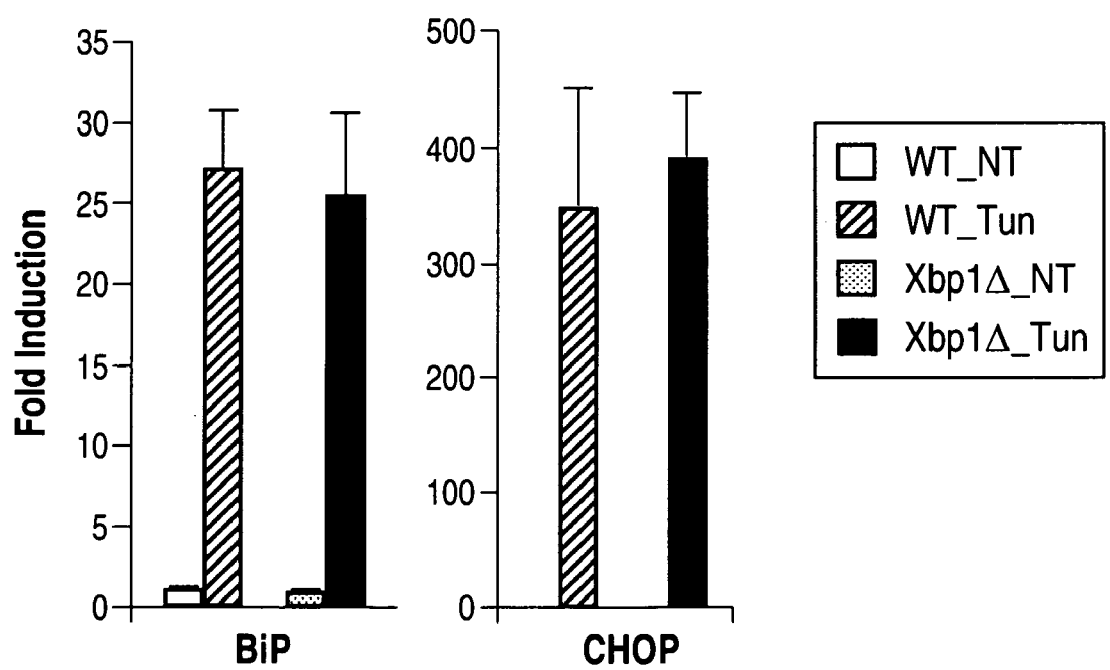
Figure 1F:
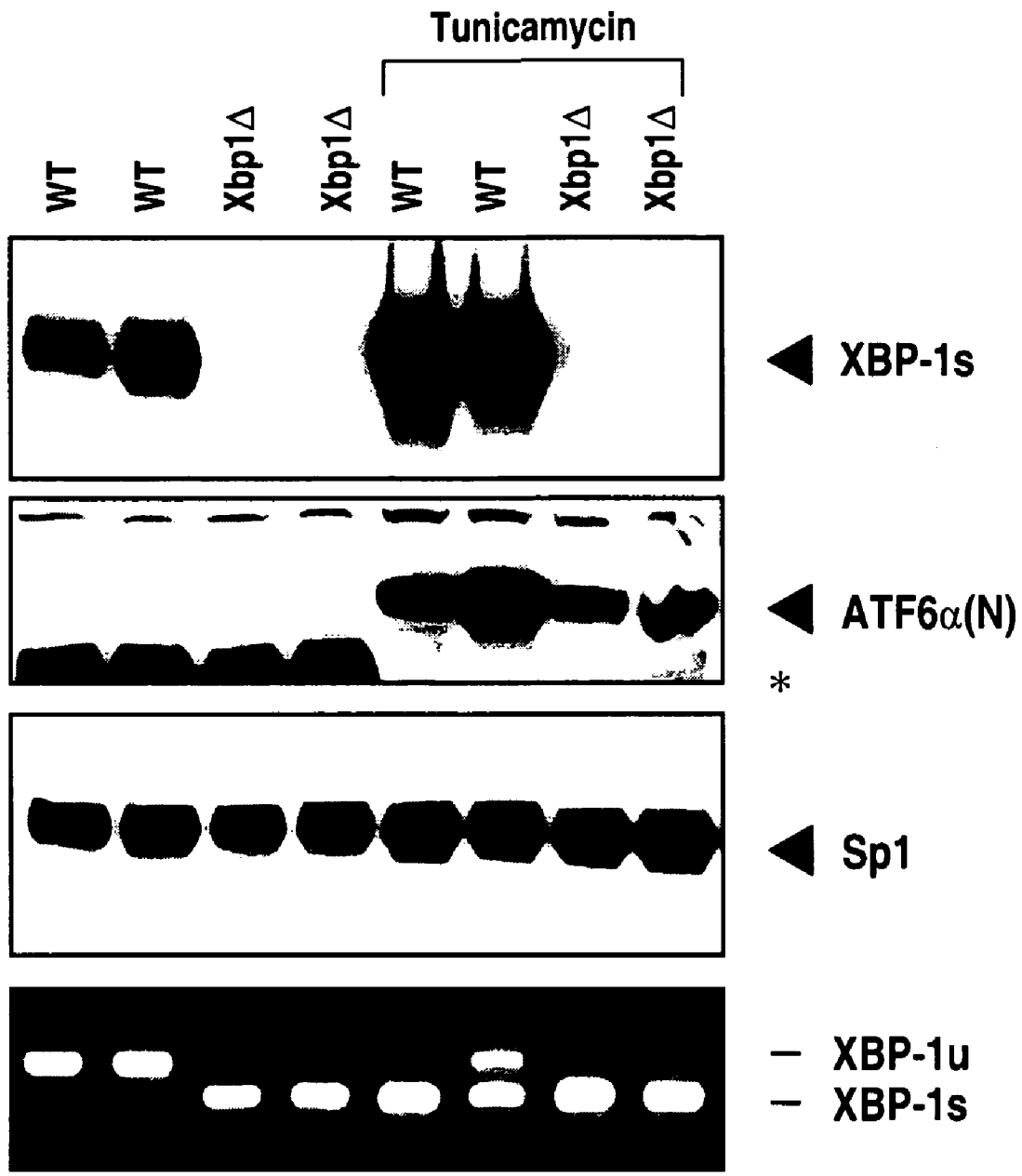
Figure 1G:
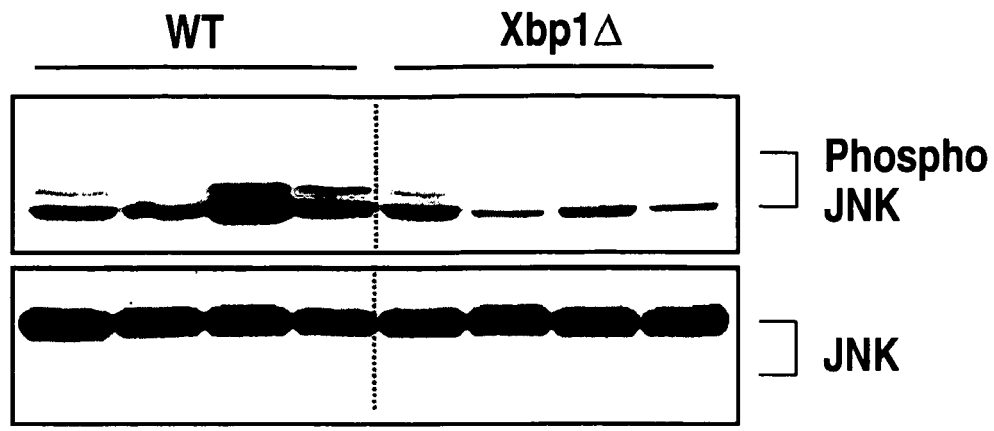
Figure 1H:
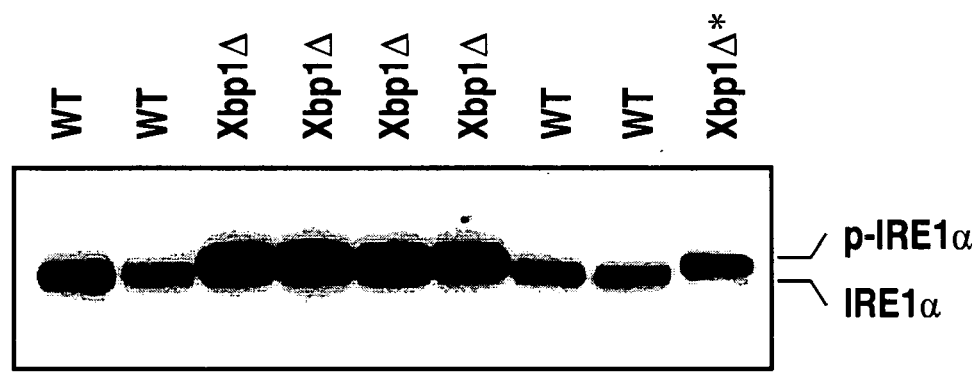
Figure 1I:
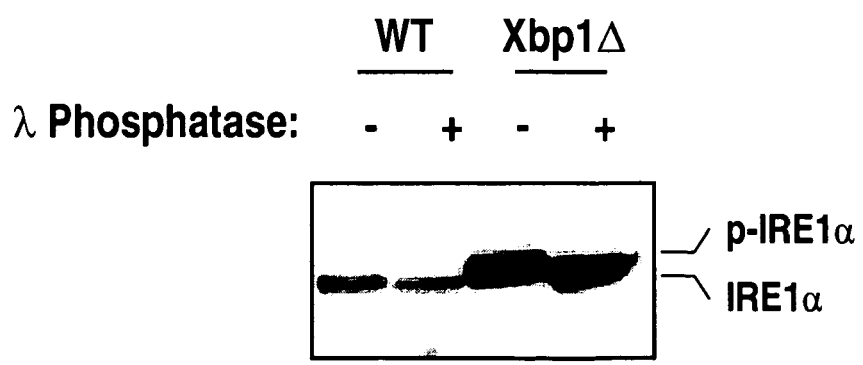

It has been previously established that XBP-1 is essential for embryonic liver development (A. M. Reimold et al. (2000) *Genes Dev* 14, 152). Given that the adult liver is a secretory organ that produces multiple plasma proteins, it was speculated that XBP-1 would also be required for adult hepatocyte secretory function and survival. However, no noticeable abnormalities in body weight or liver mass were observed in XBP-1Δ mice (Table 1) and liver damage was not present in the mutant mice as determined by serum ALT level and histological analysis (Table 1 and FIG. 1a, b). The ultrastructure of the ER appeared to be normal, although it was somewhat less abundant in the mutant hepatocytes (FIG. 1c,d). The role of XBP-1 in the secretory function of the liver was next examined. The liver produces various protein species that constitute the majority of plasma proteins, including albumin. Serum albumin and total protein levels were decreased slightly in XBP-1Δ mice, suggesting some minor compromise in hepatic protein secretory function in the absence of XBP-1 (Table 1). Surprisingly, XBP-1 dependent UPR target genes such as EDEM, ERdj4 and Sec61a were only modestly down regulated in XBP-1Δ liver in the basal state (FIG. 1e). Further, the absence of XBP-1 in liver did not itself evoke an ER stress response as evidenced by the lack of ATF6a processing together with normal levels of the PERK regulated BiP and CHOP mRNAs, as well as basal amounts of phosphorylated c-Jun N-terminal Kinase (JNK), a downstream target of IRE-1 (FIG. 1e-g). Microarray analysis also confirmed the normal expression of XBP-1-independent stress markers in XBP-1Δ liver (Table 2). As a control, the pharmacological ER stress inducer tunicamycin normally activated ATF6a processing and PERK-dependent UPR gene expression in XBP-1Δ liver, excluding the possibility that the hepatocytes had adapted to a putative stress milieu. As expected, XBP-1-dependent UPR target genes such as EDEM, ERdj4 and Sec61a were not induced by tunicamycin treatment in XBP-1. liver (FIGS. 1e and f). Interestingly, however, the absence of XBP-1 led to the constitutive activation of its upstream activator IRE-1 alpha as evidenced by robust splicing of the mutant XBP-1 mRNA and induction of both IRE-1 alpha protein and its phosphorylation, as shown by a band shift, which was eliminated by phosphatase treatment (FIGS. 1f, h and i). Hence, IRE-1 alpha, but not PERK or ATF6, is activated in XBP-1 deficient liver, suggesting feedback regulation of IRE-1 alpha by its downstream target XBP-1 in an ER stress independent manner.

Example 3

Decreased Level of Plasma Lipids in XBP-1Δ Mice

Figure 2A:
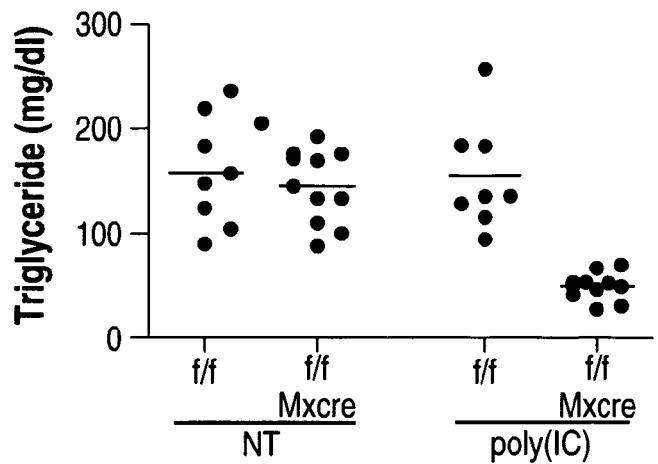
FIGS. 2A-2G show the plasma and hepatic lipid profiles of XBP-1 deficient mice. XBP-1$^{f/f}$ and XBP-1$^{f/f}$; Mx1-cre mice were injected 3× with poly(I:C). Three weeks after the last injection, (A) plasma TG, (B) plasma cholesterol, and (C) serum free fatty acid levels were measured. (D) Plasma TG levels were measured over time in mice that received a single injection of 250 μg of poly(I:C). Error bars represent SEM. N=6-7 (E) Distribution of plasma cholesterol was determined by FPLC separation of lipoprotein particles. (F) Fat content in the liver was determined by oil red O staining. (G) Lipid composition in the liver was determined by Lipomics analysis. N=4/group.
Figure 2B:
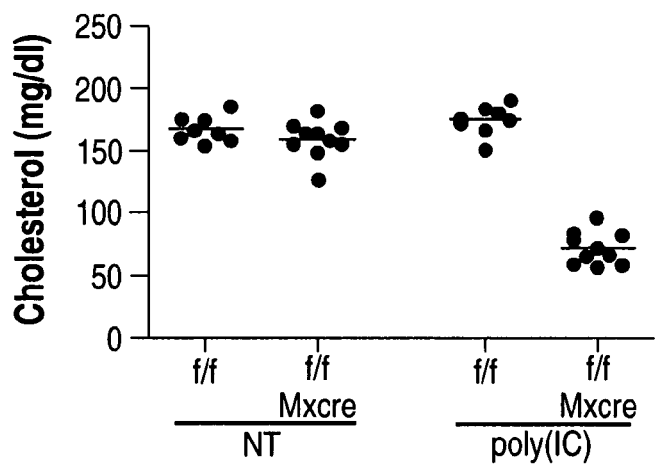
Figure 2C:
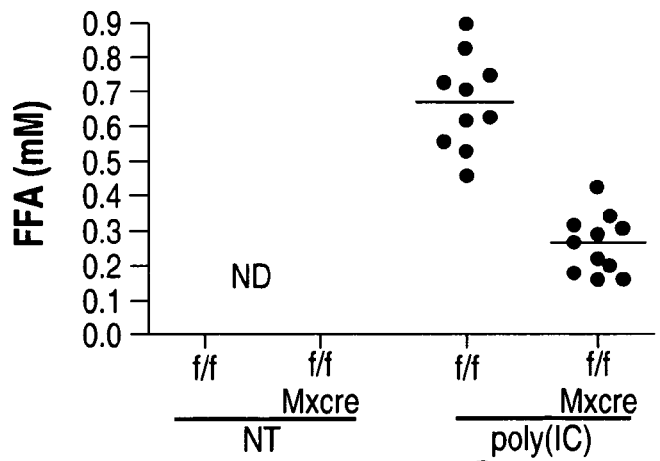
Figure 2D:
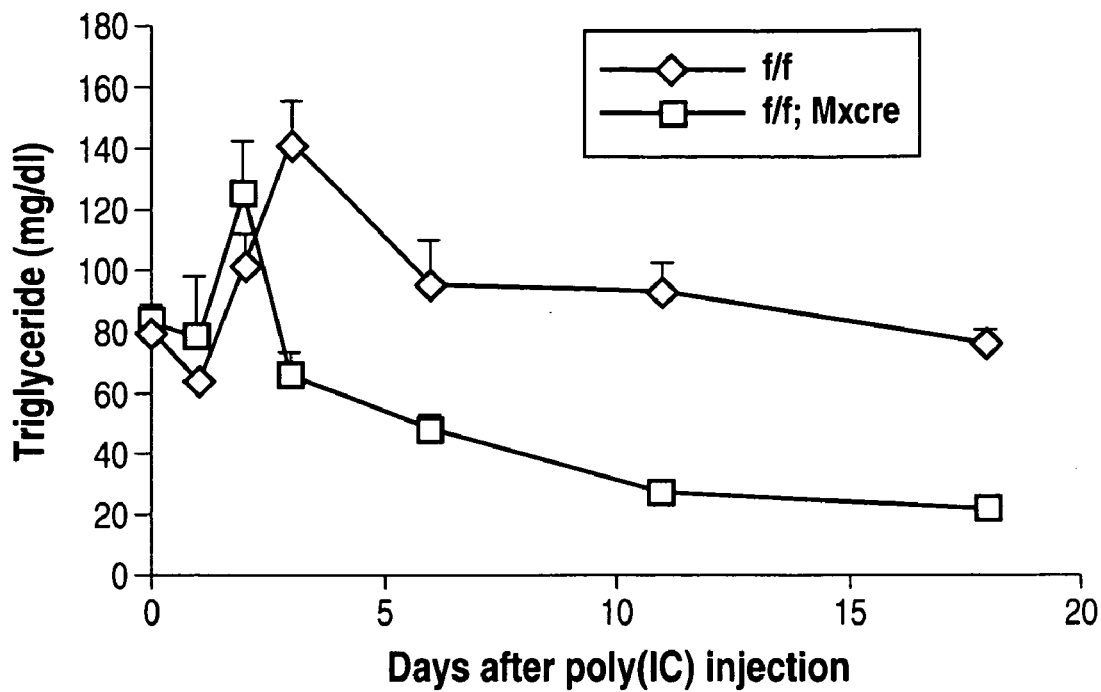
Figure 2E:
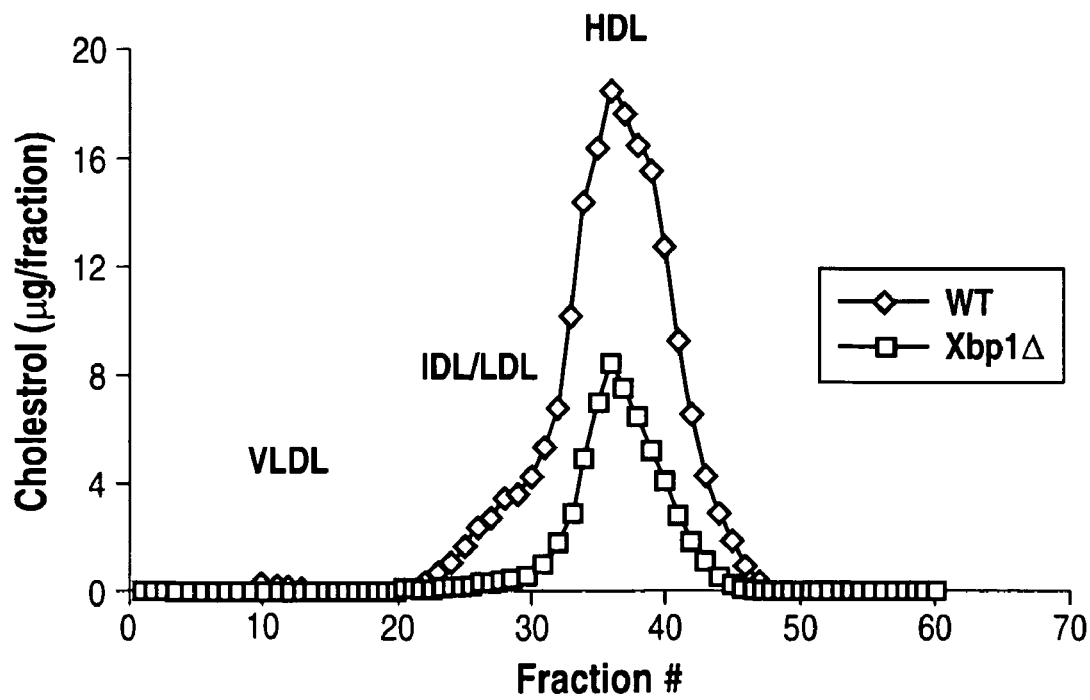
Figure 2F:
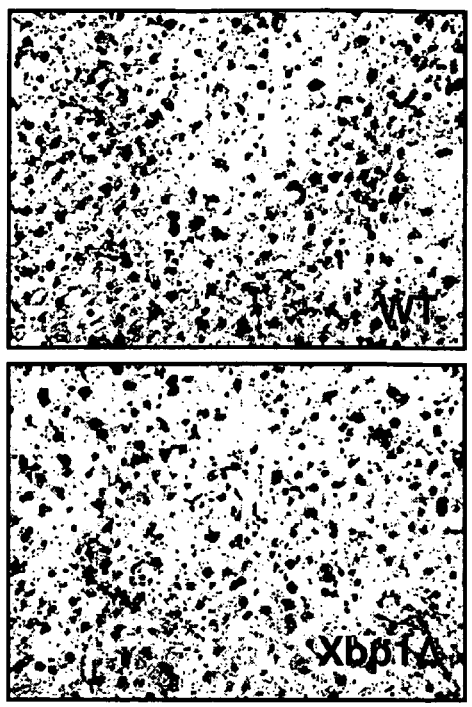
Figure 2G:
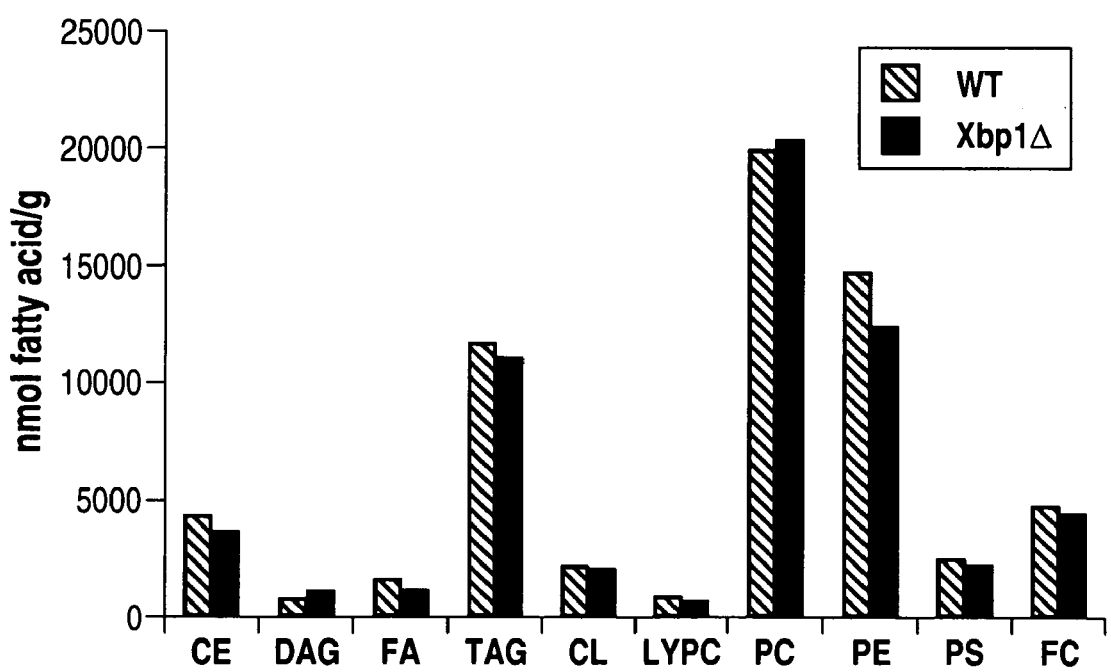

The presence of significant amounts of XBP-1s protein in hepatocytes in the basal state suggests some function for this transcription factor that may be unrelated to secretory protein synthesis or the ER stress response. Recent work has demonstrated that XBP-1 increases phospholipid biosynthesis to allow ER expansion, partly through posttranscriptional activation of enzymes in the phosphatidylcholine synthesis pathway (R. Sriburi, et al. (2004) *J Cell Biol* 167, 35). Since XBP-1 plays an important role in membrane lipid synthesis in the ER, it was determined whether it might play a role in fatty acid synthesis in the liver. Remarkably, injection of poly(I:C) into XBP-1$^{f/f}$; Mx1cre mice resulted in dramatic decreases of plasma TG, cholesterol and free fatty acids (FIG. 2a-c). In a time course experiment, the plasma TG level was lower compared to WT as early as three days after a single injection of poly(I:C) into XBP-1$^{f/f}$; Mx1cre mice (FIG. 2d) and further decreased over time. An early transient spike in TG in both strains was observed likely due to an inflammatory response to poly(I:C). XBP-1 deletion also caused striking changes in the distribution of cholesterol, resulting in an almost complete absence of LDL and VLDL-associated cholesterol (FIG. 2e). In contrast, the content and composition of hepatic lipids were not significantly changed in XBP-1Δ mice (FIG. 2f, g), indicating that low plasma lipid levels were not due to retention of lipids in the liver.

Example 4

Decreased TG Secretion from XBP-1Δ Liver

Figure 3A:
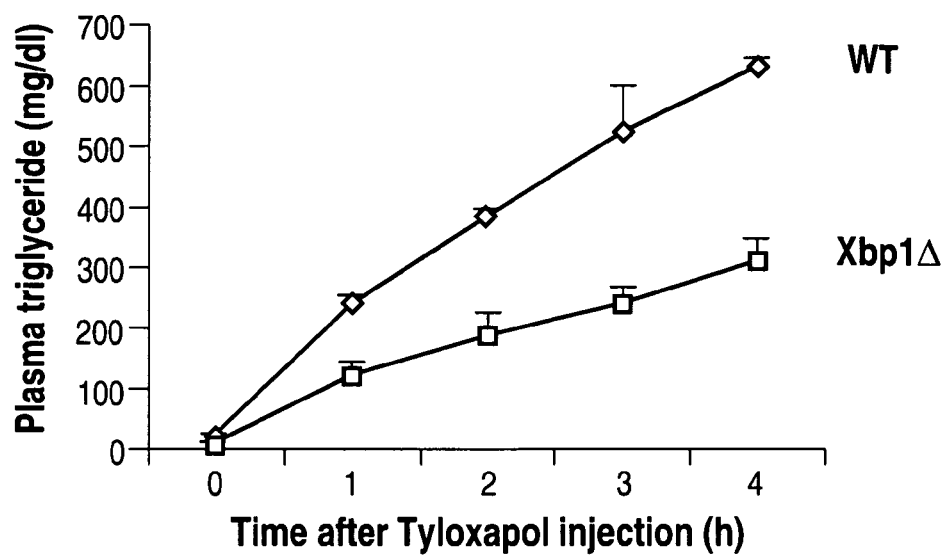
FIGS. 3A-3C show diminished hepatic TG secretion, but normal turnover of apoB-100 in the absence of XBP-1. (A) Mice were injected with Tyloxapol after a four-hour fast and plasma triglyceride levels measured over time. N=4/group. (B) Western blot analysis of plasma apoB-100 before and after poly(I:C) injection. (C) Primary hepatocytes from WT and XBP-1Δ (XBP-1 knock-out) mice were labeled with $^{35}$S-methionine/cysteine for 60 min and then chased for indicated times. Radiolabeled apoB-100 protein species were immunoprecipitated and revealed by fluorography.

The liver secretes VLDL lipoprotein particles that transport fatty acids and cholesterol to peripheral tissues (N. O. Davidson, G. S. Shelness (2000) *Annu Rev Nutr* 20, 169; M. M. Hussain, et al. (2003) *Front Biosci* 8, s500). To test whether VLDL-associated TG secretion was impaired in the absence of XBP-1, mice were injected with Tyloxapol (M. C. Schotz, et al. (1957) *Am J Physiol* 188, 399), a compound that inhibits the breakdown of VLDL lipids (FIG. 3a). XBP-1Δ mice displayed a significantly decreased rate of plasma TG accumulation, indicating impaired TG secretion from liver.

Figure 3B:
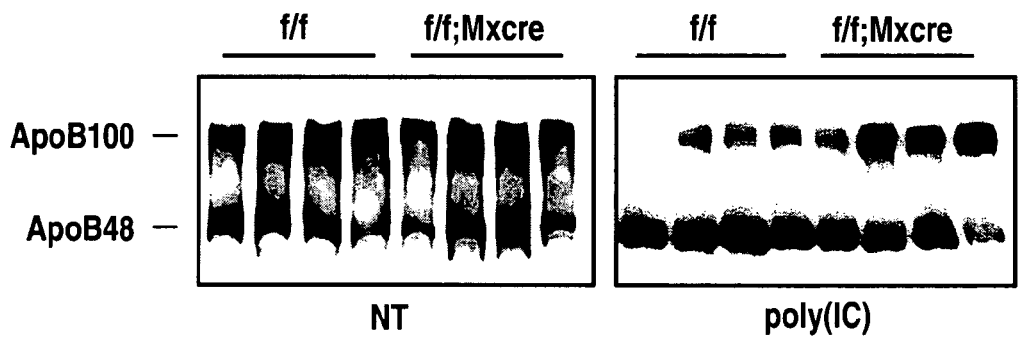
Figure 3C:
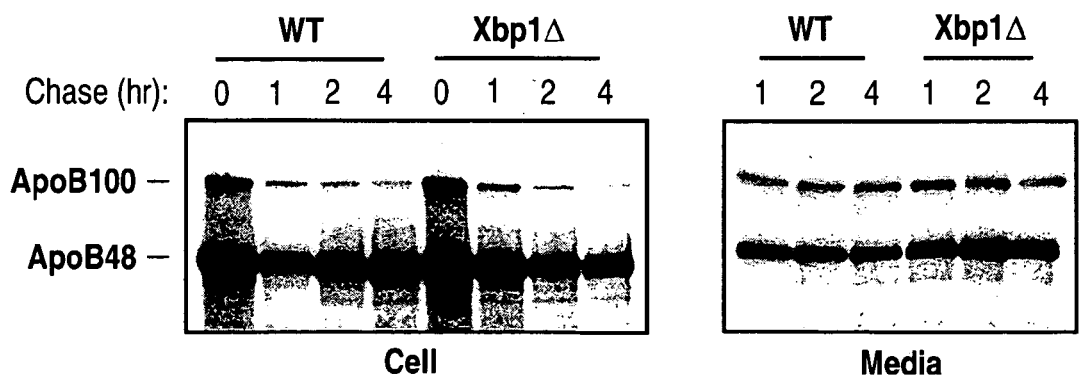

Apolipoprotein B-100 (ApoB-100) is a major protein component of VLDL, which is cotranslationally translocated into the ER lumen for association with triglyceride (O. Davidson, G. S. Shelness (2000) *Annu Rev Nutr* 20, 169). Inefficient folding and lipidation of apoB-100 leads to its ubiquitination followed by proteasomal degradation via the ER associated degradation pathway (ERAD) (E. A. Fisher et al. (2001) *J Biol Chem* 276, 27855). Since XBP-1 regulates the expression of genes facilitating ER folding and ERAD under ER stress conditions (P. Cohen et al. (2002) *Science* 297, 240)-albeit those genes (such as EDEM and Erdj4) were only modestly down-regulated in XBP-1Δ liver in the basal state, it was determined whether apoB-100 folding and secretion were affected by the absence of XBP-1. Steady state plasma apoB-100 levels as measured by western blot were not significantly changed in XBP-1Δ mice (FIG. 3b). Similarly, the stability and secretion of the newly synthesized radiolabeled apoB-100 protein from primary hepatocytes were not altered by loss of XBP-1 (FIG. 3c), demonstrating that ApoB-100 is not the target of XBP-1 action on plasma lipids.

Example 5

Role of XBP-1 in Lipogenic Gene Expression in the Liver

Figure 4A:
FIGS. 4A-4C depict the expression of lipogenic genes in the XBP-1 deficient liver. Total RNAs were prepared from livers of mice fed a standard rodent chow diet. (A) Northern blot analysis performed to measure the expression of Dgat2, Scd1 and Fasn genes. Ethidium bromide staining of the gel is shown as a loading control. (B) Expression of lipogenic genes was measured by quantitative real time PCR with actin mRNA as an internal control. Values represent relative amounts of each mRNA compared to WT. Statistical significance of differences between WT and XBP-1Δ was determined by student T tests. *, p<0.005; **, p<0.0001. (C) Liver nuclear extracts from: WT and XBP-1Δ mice were subjected to western blot analysis with XBP-1, SREBP-1 and SREBP2 antibodies.
Figure 4C:
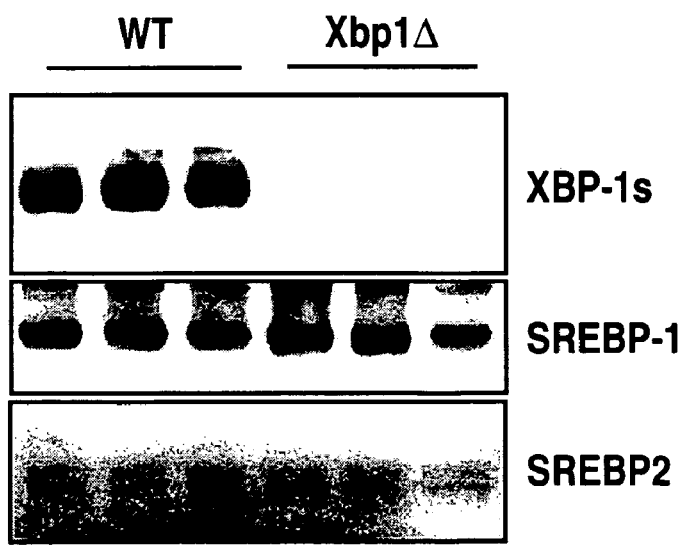
Figure 4B:
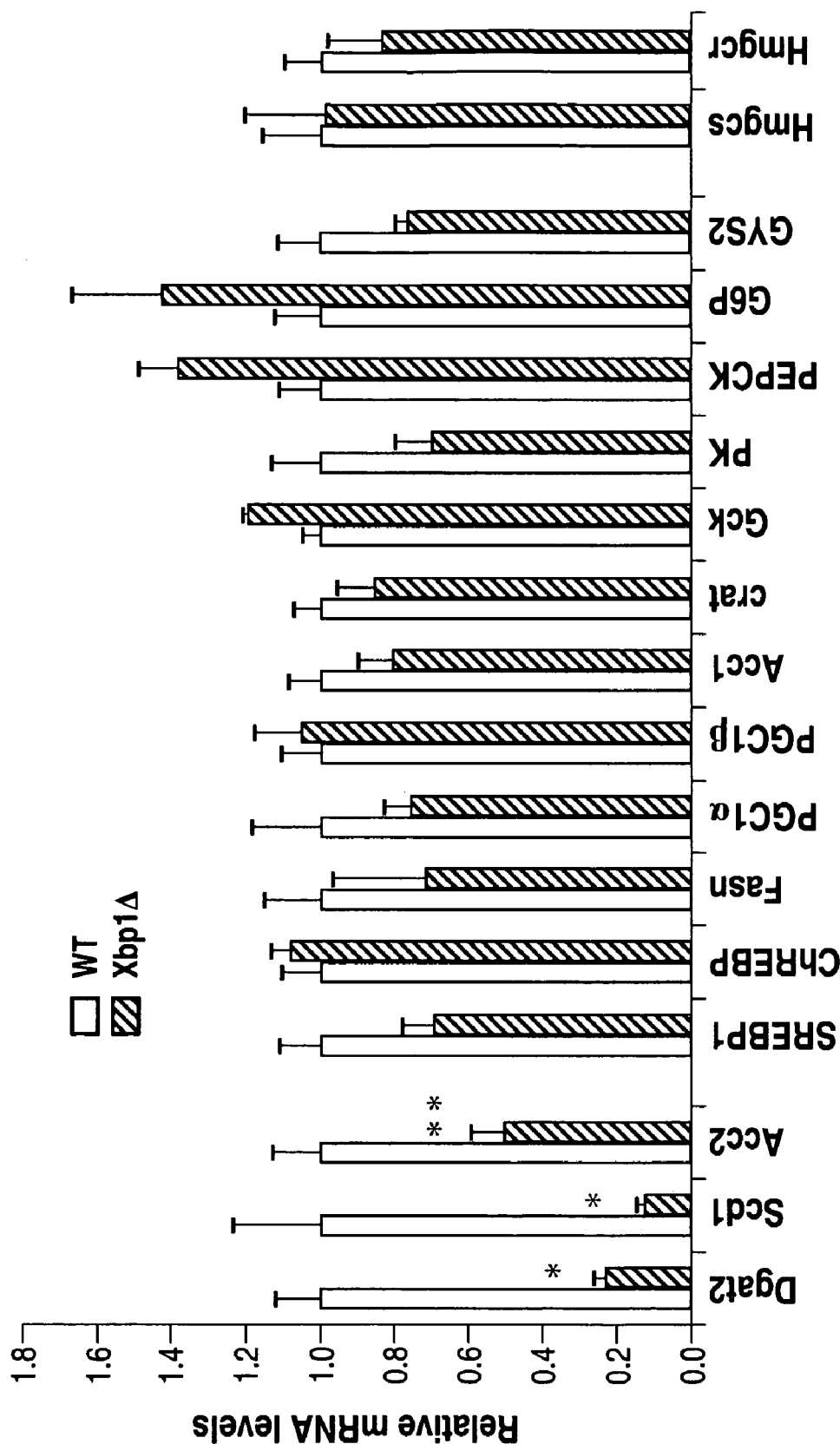

Reduced TG secretion that is unaccompanied by lipid accumulation in the liver suggests that de novo lipid synthesis might be compromised in XBP-1Δ liver. Therefore, it was determined whether XBP-1 regulates the expression of genes involved in glycolysis and lipid synthesis pathways. Gene expression profiling revealed that critical lipogenic genes such as stearyl coA desaturase 1 (Scd1), diacyl glycerol acetyltransferase 2 (Dgat2), and acetyl coA carboxylase 2 (Acc2) were significantly downregulated in XBP-1Δ liver, and these observations were verified by Northern blot and real time RT-PCR analyses (FIGS. 4a and b). It is noteworthy that genetic ablation or inhibition using antisense oligonucleotides of these genes has profound effects on hepatic lipid metabolism, lowering TG production and increasing fatty acid oxidation (P. Cohen et al. (2002) *Science* 297, 240; S. J. Stone et al. (2004) *J Biol Chem* 279, 11767; X. X. Yu et al. (2005) *Hepatology* 42, 362; J. M. Ntambi et al. (2002) *Proc Natl Acad Sci USA* 99, 11482; L. Abu-Elheiga, et al. (2003) *Proc Natl Acad Sci USA* 100, 10207). In contrast, expression of fatty acid synthase (Fasn), HMG-CoA synthase (Hmgcs) and HMG-CoA reductase (Hmgcr), genes regulated by SREBP family transcription factors, was not altered in XBP-1 genes has profound effects on hepatic lipid metabolism, lowering TG production and increasing fatty acid oxidation. In contrast, expression of fatty acid synthase (Fasn), HMG-CoA synthase (Hmgcs) and HMG-CoA reductase (Hmgcr) (J. D. Horton, J. L. Goldstein, M. S. Brown (2002) *J Clin Invest* 109, 1125), genes regulated by SREBP family transcription factors, was not altered in XBP-1Δ mice, consistent with the normal levels of SREBP-1 and SREBP-2 mRNAs and the processed nuclear protein species (FIGS. 4b and 4c). ChREBP expression was also normal in XBP-1Δ liver. These results provide evidence that XBP-1 regulates the expression of a subset of lipogenic genes in an SREBP and ChREBP independent manner.

Example 6

Dietary Regulation of XBP-1 and Lipogenic Genes in the Liver

Figure 5A:
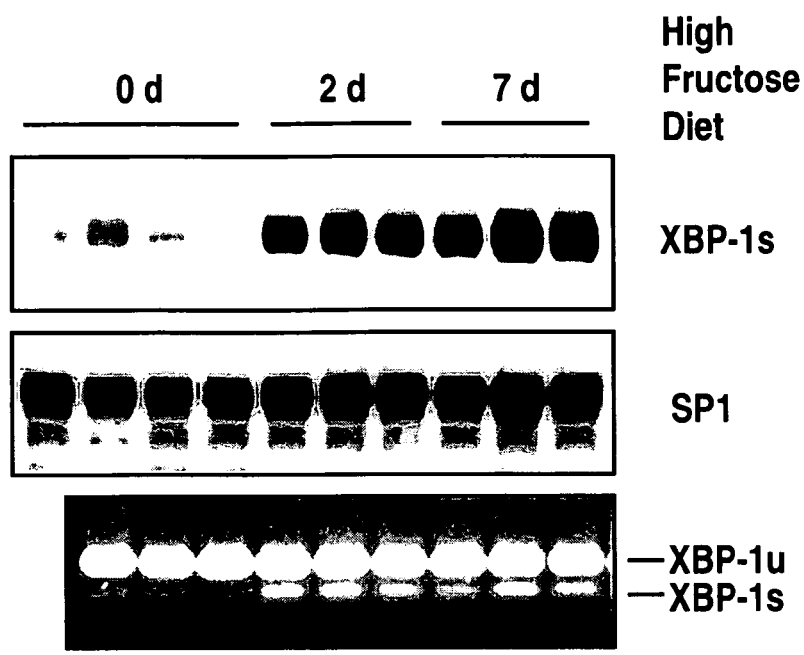
Figure 5B:
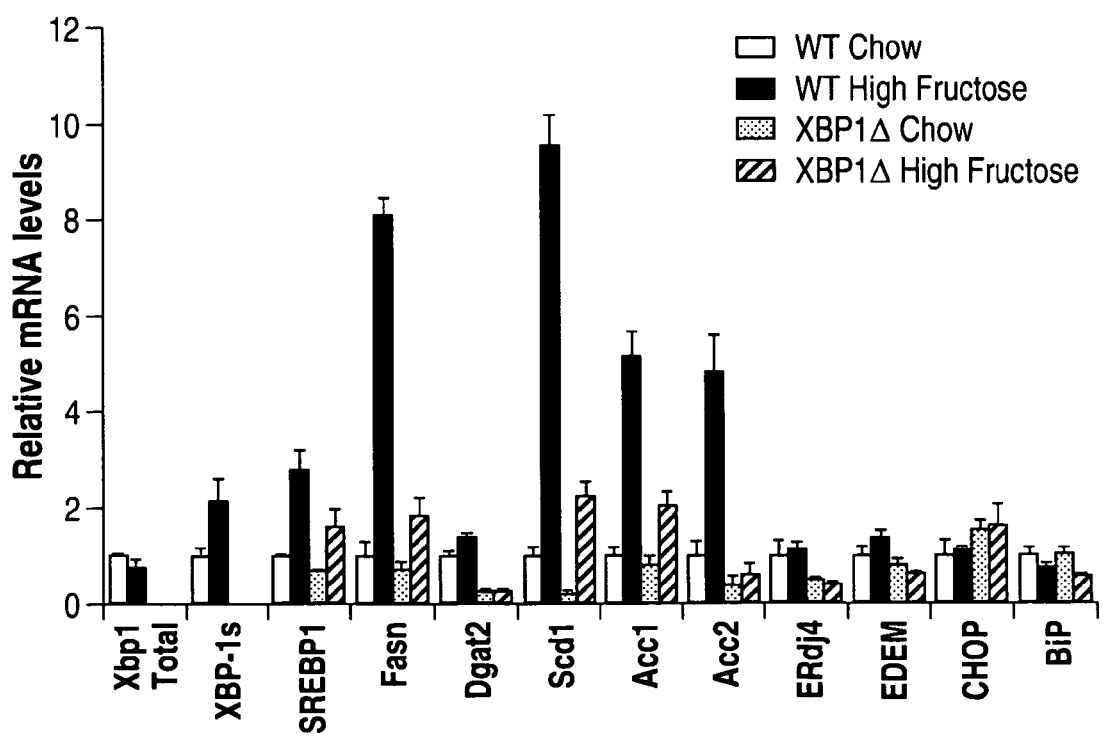

Prolonged feeding of high carbohydrate diets increases lipid synthesis in the liver through induction of genes encoding lipogenic enzymes (H. C. Towle, et al. (1997) *Annu Rev Nutr* 17, 405; M. Miyazaki et al. (2004) *J Biol Chem* 279, 25164). Fructose is a particularly strong inducer of lipogenic gene expression and de novo lipid synthesis in the liver that predisposes toward development of metabolic syndrome (M. Miyazaki et al. (2004) *J Biol Chem* 279, 25164; H. Basciano, L. Federico, K. Adeli, (2005) *Nutr Metab* (Lond) 2, 5). Interestingly, it was observed that hepatic XBP-1s protein was dramatically induced in mice fed a 60% fructose diet, along with a modest increase of its mRNA reflecting increased splicing by IRE-1 alpha (FIGS. 5a and 5b). Neither ATF6a processing nor representative UPR target genes such as CHOP and BiP were induced under the same conditions. Consistent with the results above, XBP-1s was also induced in primary hepatocytes cultured in medium containing high concentrations of glucose, suggesting that the increased glucose availability in the diet induces XBP-1 activation in the liver. These results suggest the presence of a novel mechanism of XBP-1 activation in the liver under carbohydrate-induced lipogenic conditions that is unrelated to the conventional ER stress response. As expected, the high fructose diet significantly increased the mRNA levels of lipogenic genes such as Fasn, Scd1, Acc1 and Acc2 in WT liver (FIG. 5b). Dgat2 was only slightly increased by high fructose diet feeding. Notably, expression of these same lipogenic genes was severely compromised in the liver of XBP-1Δ mice fed the high fructose diet (FIG. 5b). Hence, XBP-1 is required for the expression of a subset of critical lipogenic genes in the setting of high carbohydrate intake.

Example 7

Direct Regulation of Lipogenic Genes by XBP-1

Figure 5D:
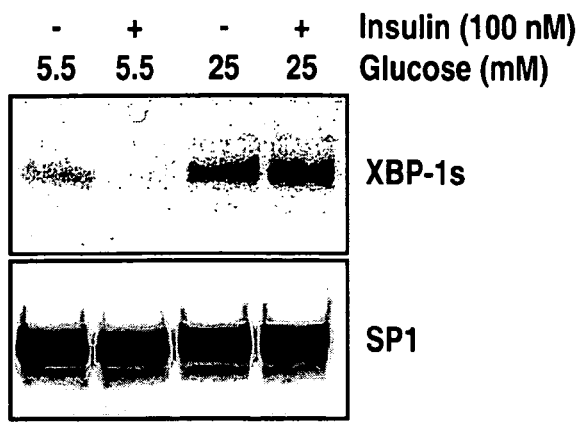
Figure 5D:
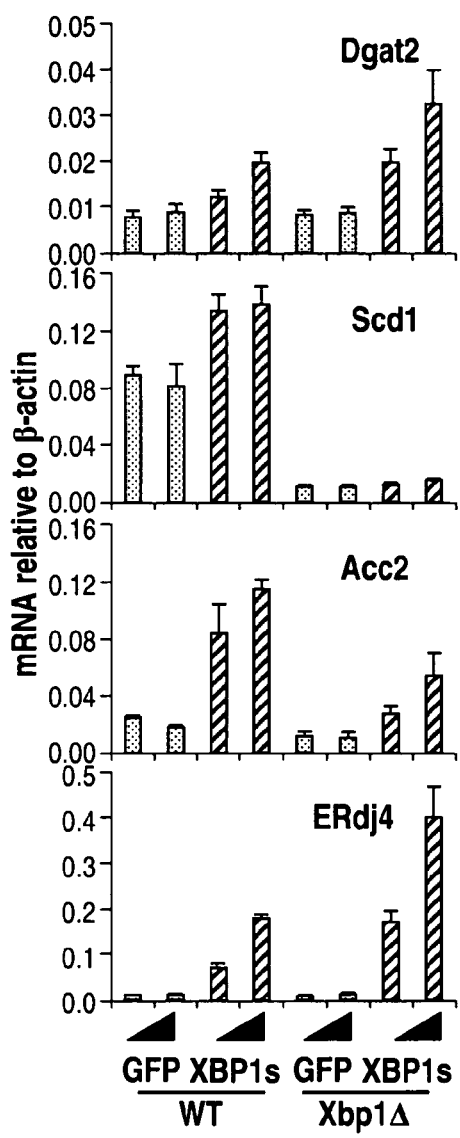
Figure 5E:
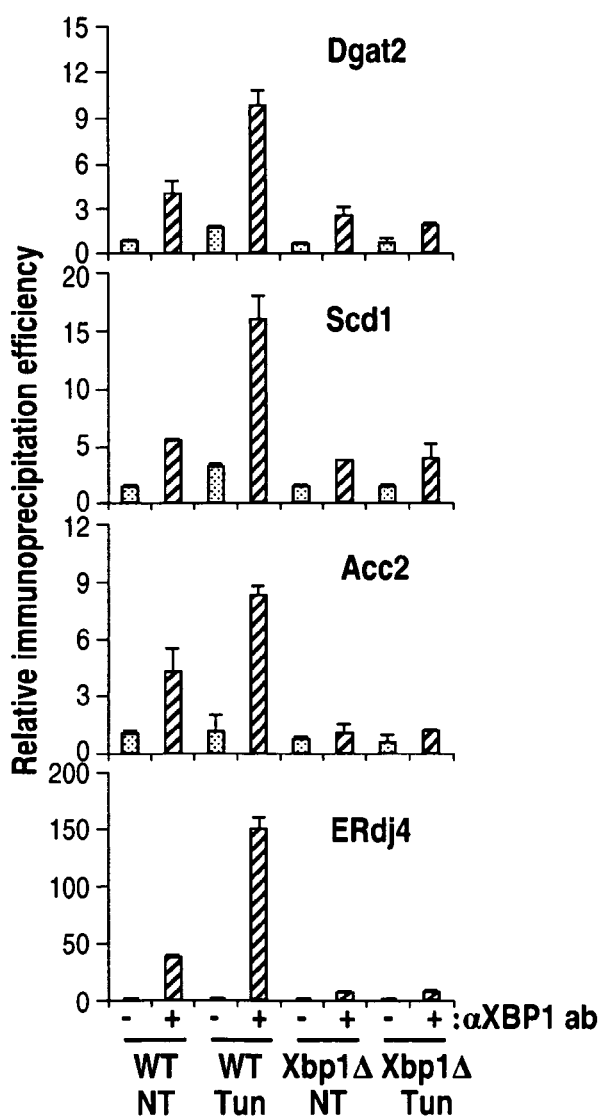

Since IRE-1 alpha was constitutively active in XBP-1Δ liver, it was determined whether the compromised expression of lipogenic genes was due directly to the lack of XBP-1 or indirectly to the hyperactivation of the upstream activator, IRE-1 alpha. To test whether XBP-1s is sufficient to induce these lipogenic genes, XBP-1s was over-expressed in primary mouse hepatocytes using recombinant adenoviruses. Enforced expression of XBP-1s significantly increased the expression of Dgat2 and Acc2 mRNAs, as well as the known XBP-1 target gene, ERdj4 both in WT and XBP-1 deficient hepatocytes (FIG. 5c). Further, chromatin immunoprecipitation (CHIP) assays using liver nuclear extracts from mice fed a high fructose diet demonstrated direct binding of XBP-1 to promoter regions of the Dgat2, Scd1 and Acc2 genes (FIG. 5d). Specific binding of XBP-1 to the promoter of these lipogenic genes was further increased by tunicamycin treatment, which increased the level of nuclear XBP-1s. Taken together, these data establish XBP-1 as a novel transcription factor governing hepatic lipogenesis by directly controlling the expression of critical lipogenic genes.

The SREBP transcription factor family and the more recently discovered factor ChREBP are required for lipid synthesis in the liver (J. D. Horton, J. L. Goldstein, M. S. Brown (2002) *J Clin Invest* 109, 1125; K. Uyeda, J. J. Repa (2006) *Cell Metab* 4, 107). These transcription factors bind to specific promoter elements to cooperatively activate genes encoding enzymes in glycolytic and lipogenic pathways. SREBP-1c and SREBP-2 primarily regulate genes involved in fatty acid and cholesterol synthesis pathways, respectively while ChREBP regulates genes involved in glycolysis and fatty acid synthesis. Upon carbohydrate intake, insulin produced from the pancreas transcriptionally activates SREBP-1c, while glucose promotes ChREBP dephosphorylation and its subsequent nuclear translocation (K. Uyeda, J. J. Repa (2006) *Cell Metab* 4, 107). SREBP-1c and ChREBP are also transcriptionally activated by the nuclear receptor LXR which appears to serve as a glucose sensor (N. Mitro et al. (2007) *Nature* 445, 219). Here an essential role for the transcription factor, XBP-1, in controlling hepatic lipogenesis was demonstrated. Hence XBP-1 has at least two distinct functions: in some organs and cells, it is required for protein secretory function (plasma cells, pancreatic exocrine cells) and in others, such as adult liver, it does not substantially affect protein secretory function but rather controls lipogenesis. Remarkably, deficiency of XBP-1 in the liver led to profound decreases in serum TG, cholesterol and free fatty acids without causing hepatic steatosis. XBP-1 was induced upon high carbohydrate diet feeding and directly activated key lipogenic genes in the liver. These data reveal an unexpected and biologically critical function of XBP-1 in hepatic lipogenesis, quite separate from its function as a mediator of the ER stress response (D. Ron, P. Walter (2007) *Nat Rev Mol Cell Biol* 8, 519).

Given XBP-1's known function as a key mediator of the UPR, it was surprising that its function in regulating lipogenesis was unrelated to the ER stress response. However, ablation of XBP-1 did not activate the two other arms of the UPR, ATF6 or PERK signaling pathways, in the liver, indicating the absence of increased ER stress. Indeed, the folding and lipidation of apoB-100 protein, the building block of VLDL particles, that occurs in the ER (N. O. Davidson, G. S. Shelness (2060) *Annu Rev Nutr* 20, 169; M. M. Hussain, et al. (2003) *Front Biosci* 8, s500), was not compromised in XBP-1 deficient hepatocytes. Similarly, overall hepatocyte protein secretory function was minimally compromised by loss of XBP-1, likely because XBP-1 independent basal chaperone gene expression is sufficient to accommodate moderate secretory loads. Instead, as shown herein, XBP-1 directly transactivates the expression of select lipogenic genes. Therefore, the low plasma lipid levels observed in XBP-1Δ mice are primarily due to decreased de novo synthesis of lipids in the liver, rather than to defective assembly and secretion of VLDL particles, consistent with the normal folding and secretion of apoB-100.

Figure 7:
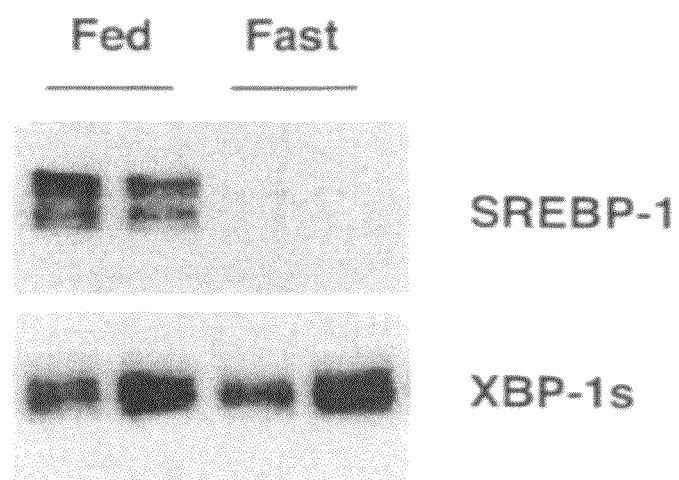
FIG. 7 depicts liver nuclear extracts prepared from mice fed or fasted for 12 h and subjected to western blot analysis with anti-XBP-1 or anti-SREBP-1 antibodies. Two C57BL/6 mice were used per group.

Interestingly, IRE-1 alpha, the upstream activator of XBP-1, was constitutively active in the XBP-1Δ liver, suggesting the presence of a feedback loop that precisely maintains XBP-1s protein levels. These findings demonstrate the existence of a signal that is linked to levels of XBP-1s protein, for the selective activation of IRE-1 alpha even in the absence of ER stress. The nature of this signal and its relationship to the ER stress response and the activation of XBP-1 in the liver by carbohydrate feeding are unknown. However, the profound increase in XBP-1s protein in the liver of mice fed a high fructose diet suggests that the rheostat that adjusts levels of XBP-1s may react to the abundance of ingested carbohydrate. Glucose itself, but not insulin, appeared to be the sensor since XBP-1s protein levels did not change in either fasted mouse liver (FIG. 7) or hepatocytes treated with insulin. In contrast, XBP-1s protein was significantly induced in hepatocytes cultured under high glucose conditions, suggesting that XBP-1 is controlled by glucose at least partly through IRE-1 alpha activation.

In both yeast and mammals, XBP-1 (Hac1p) is thought to regulate membrane lipid biosynthesis and ER biogenesis (R. Sriburi, et al. (2004) *J Cell Biol* 167, 35; J. S. Cox, et al. (1997) *Mol Biol Cell* 8, 1805). It is intriguing to speculate that mammals have evolved to employ XBP-1 for both phospholipid biosynthesis during the development of professional secretory cells and triglyceride synthesis in the liver for long-term energy storage. It is not fully understood how Hac1p and XBP-1 regulate phospholipid synthesis but in yeast it appears that Hac1p antagonizes the transcriptional repressor Opi1p, allowing the activation of genes encoding phospholipid biosynthesis enzymes (J. S. Cox, et al. (1997) *Mol Biol Cell* 8, 1805). XBP-1 increases enzymatic activities in the phospholipid biosynthesis pathway, although its direct transcriptional target (s) are not known (R. Sriburi, et al. (2004) *J Cell Biol* 167, 35). Previous work has shown a modest activation of IRE-1 by extracellular glucose in pancreatic beta cells (K. L. Lipson et al. (2006) *Cell Metab* 4, 245). Similarly, it is noted that XBP-1s mRNA was modestly increased under the same conditions in hepatocytes. However, the far more marked induction of XBP-1s protein by high fructose diet feeding implies the importance of post-translational modifications. Glucose has been shown to induce dephosphorylation and subsequent nuclear translocation of ChREBP through activation of protein phosphatase2A (K. Uyeda, J. J. Repa (2006) *Cell Metab* 4, 107). The phosphorylation of cellular XBP-1s may be similarly regulated by glucose.

It has been previously shown that ER stress is present in the liver of genetically manipulated or high fat diet induced obese mice, likely from increased free fatty acids or TG (U. Ozcan et al. (2004) *Science* 306, 457; D. Wang, Y et al. (2006) *Endocrinology* 147, 943; T. Ota, et al. (2007) *J Clin Invest*; G. S. Hotamisligil (2005) *Diabetes* 54 Suppl 2, S73). In this setting, ER stress-mediated JNK activation inhibited insulin signaling, linking obesity with the development of hepatic insulin resistance. The data presented herein reveals that XBP-1 deficiency does not induce noticeable ER stress in the liver, but does profoundly reduce fatty acid production. Finally, the XBP-1Δ liver displays a qualitatively and quantitatively normal lipid profile with no hepatic steatosis in the presence of profoundly decreased LDL cholesterol levels. This is in contrast to Mttp and Apob mutant mice where lipid accumulates in the liver due to impaired VLDL assembly/ secretion (M. Raabe, et al. (1998) *Proc Assoc Am Physicians* 110, 521), and to mutant mice lacking SREBPs where hepatic lipids are diminished (J. D. Horton, J. L. Goldstein, M. S. Brown (2002) *J Clin Invest* 109, 1125). Preservation of the normal hepatic lipid profile suggests that compounds that inhibit XBP-1 activation in the liver may reduce serum lipids without causing hepatic steatosis in patients with dyslipidemia.

Example 8

Role of XBP-1 in vivo in de novo Hepatic Lipogenesis in Dietary and Genetic Models of Metabolic Disorders Dysregulation of lipid metabolism manifested by hyperlipidaemia and hepatic steatosis is closely associated with the development of insulin resistance, type 2 diabetes, and atherosclerosis. The consequences of deleting Xbp1 in liver are profound with marked hypocholesterolemia and hypotriglyceridemia at baseline. Notably, this phenotype is not accompanied by abnormalities in hepatic lipid levels or hepatic lipid composition. However, these results, as described above, were obtained in mice fed standard rodent chow diet. Therefore, to determine whether blockade of XBP-1 in liver is protective in the setting of conditions that predispose to hyperlipidemia, hepatic steatosis, insulin resistance, NASH and atherosclerosis, the role of XBP-1 in these disease states induced in mice either by diet or by genetic mutation is investigated.

A. Obesity, Insulin Resistance and Hepatic Steatosis.

It has been shown that germline deletion or reduction of several key lipogenic genes downstream of XBP1 not only reduced lipid accumulation in the liver, but also displayed increased insulin sensitivity. Therefore, the effects of high carbohydrate diet on obesity, hepatic steatosis and insulin resistance in XBP-1Δ mice are determined as follows. At 4 weeks of age, XBP-1 is deleted in the liver of XBP-1 flox/floxMXcre (XBP-1Δ) by poly(IC) injection (3×over 1 week). At 6 weeks of age, mice are divided into three groups, 12 mice/group. Experimental (XBP-1Δ) and control mice are fed either a standard rodent chow or high carbohydrate (70% Kcal) (RD12450B, Research Diets) diet. Body weight, fed serum triglycerides, total cholesterol and blood glucose levels are measured weekly (body weight) or bi-weekly (serum triglycerides, total cholesterol and blood glucose levels) from the initiation of the lipogenic diet. To determine the insulin sensitivity of these mice, Glucose tolerance test (GTT), glucose-stimulated insulin secretion (GSIS) and insulin tolerance tests (ITT) are performed every 4 weeks.

As compared to control mice, XBP-1Δ mice fed a high carbohydrate diet have reduced body weight, serum triglycerides, total cholesterol and blood glucose level increases, and reduced symptoms of hepatic insulin resistance.

B. Non-alcoholic Hepatosteatitis (NASH).

The prevalence of NASH is growing worldwide, in association with the staggering increases in obesity and insulin resistance. It is generally believed that "two-hits", the accumulation of fatty acids in the liver, and oxidative stress are required. In order to determine whether XBP1 plays a role in the development of NASH, XBP-1Δ XBP-1Δ mice are fed a methionine/choline-efficient (MCD) diet. The well-characterized MCD rodent model displays histologic features comparable to human NASH as well as a similar mechanistic involvement of impaired mitochondria β-oxidation. Phosphatidylcholine is the major phospholipid component of the VLDL particle, and dietary choline deficiency results in hepatic steatosis secondary to impaired VLDL assembly and secretion. Choline and methionine deficiency also results in increased generation of reactive oxygen species (ROS) that leads to oxidative damage to the cell. Cyp2E1 and CYP4A play an important role in the generation of ROS in MCD-fed rodents.

The hepatic gene expression profile of XBP-1Δ liver shows that XBP1 deficiency exerts a protective effect on the development of NASH via multiple mechanisms. First, XBP1 deletion results in decreased de novo synthesis of fatty acids by suppressing expression of lipogenic genes. Second, decreased expression of Acc2 in XBP-1Δ liver shows an increased removal of hepatic fatty acids via beta-oxidation, given the inhibitory effect of malonyl-CoA, a product of Acetyl-coA carboxylase, on fatty acid oxidation. Third, Cyp2E1 is significantly down-regulated in XBP-1Δ liver, demonstrating a decreased production of ROS.

Methionine/choline-deficient (MCD, 960439) and methionine/choline-control diets (MCC, 960441) are purchased from MP Biochemicals (Cleveland, Ohio). XBP-1Δ and control mice (Xbp1flox/flox and Xbp1flox/+; Mxcre) mice are generated by poly(IC) injection, as described above. Beginning at 6 weeks of age, mice are divided into two groups, 12 mice/group. Experimental (XBP-1Δ) and control mice are fed either a MCD or MCC diet for 2 or 6 weeks. Serum samples are used to measure aspartate aminotransferase (AST)—and alanine aminotransferase (ALT) levels as markers of liver damage. Livers will be examined by standard hostoligical techniques.

As compared to control mice, XBP-1Δ fed an MCD diet display reduced liver injury and reduced serum alanine aminotransferase and aspartate aminotransferase levels C. Hypercholesterolemia and Atherosclerosis.

The role of XBP1 in atherosclerosis induced in mice by apoE mutation and/or high dietary cholesterol was investigated as follows. At 4 weeks of age, Xbp1 was deleted in liver by poly(IC) injection (3× over 1 week). Beginning at 6 weeks of age, mice were divided into four groups, 12 mice/group. Experimental (XBP-1Δ; ApoE−/−) and control (Xbp1wt; ApoE−/−) mice were fed either a standard rodent chow containing 0.02% cholesterol or an atherogenic diet, e.g., containing 1.25% cholesterol (Test Diet, 1810830), containing 0.96% cholesterol, also referred to as a Paigen diet.

In addition, the effect of XBP-1 deletion on the standard of care, e.g., statins, is determined in this animal model of atherosclerosis by administering, e.g., a statin, to animals deficient in XBP-1 fed a standard rodent chow diet and to animals deficient in XBP-1 fed an atherogenic diet.

Serum triglycerides and total cholesterol were measured weekly. Distribution of cholesterol among HDL, IDL and LDL and IDL was determined every four weeks by FPLC analysis. After 16-24 weeks, the mice were fasted overnight and sacrificed to quantify atherosclerotic lesions by standard histological analysis.

As compared to control mice, XBP-1Δ; ApoE/− have reduced serum triglycerides and total cholesterol and reduced development of atherosclerotic lesions.

The following materials and methods were used in the foregoing Example.

Plasma triglyceride and cholesterol levels in the fed state were measured using commercial kits (Sigma, TR0100; Molecular probes, A12216). Blood glucose concentrations were measured by using ACCU-Check glucometer (Roche). Serum ALT and albumin levels were measured using commercial reagents (Bioquant). The distribution of cholesterol in plasma was determined by fast performance liquid chromatography (FPLC) separation followed by triglyceride and cholesterol assays of each fraction ausing standard techniques. Lipid composition in the liver was also determined as described above.

Figures 10A, 10B:
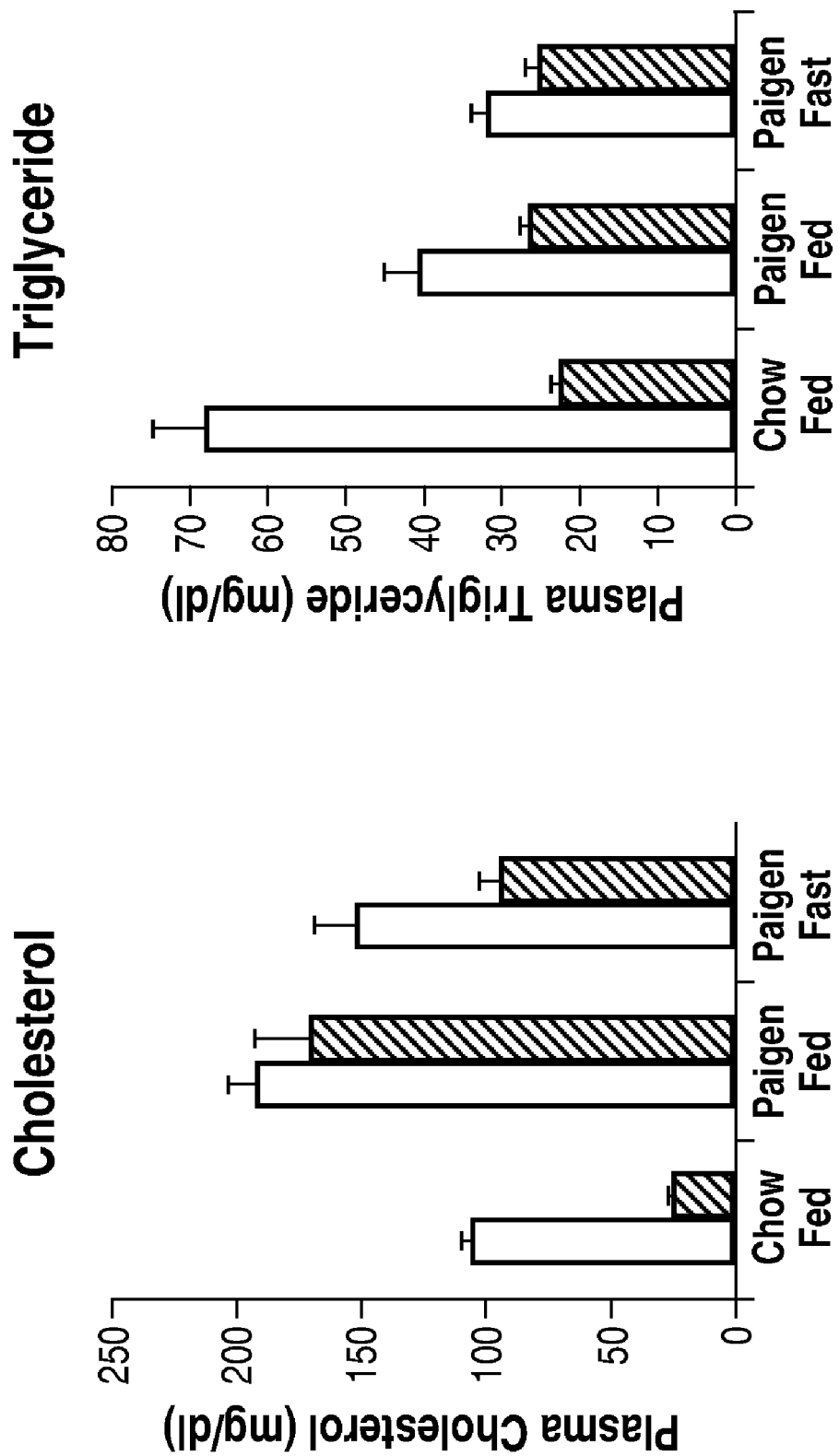
FIGS. 10A and 10B are graphs depicting the effect of XBP-1 deficiency and atherogenic diets on (A) serum cholesterol and (B) triglyceides, respectively.
Figures 11A, 11B, 11C, 11D:
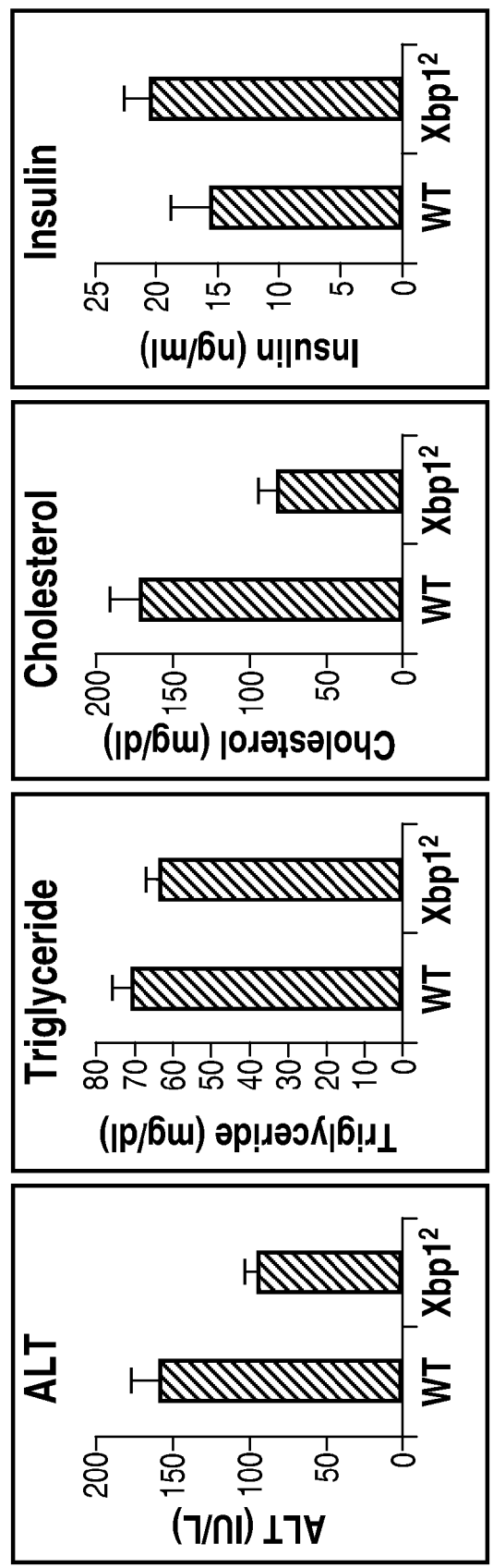
FIGS. 11A-D are graphs depicting the effect of XBP-1 deficiency and an atherogenic diet (high fat diet) on (A) serum alanine aminotransferase (ALT), (B) triglyceides, (C) cholesterol and (D) insulin.
Figure 12A:
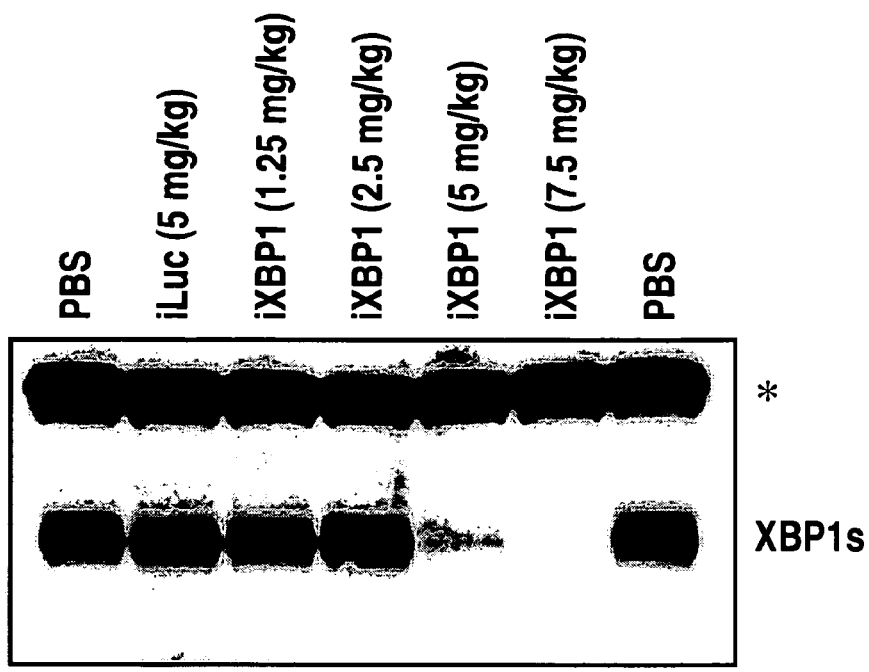
FIGS. 12A-C show that lipidoid formulated XBP-1 siR-NAs knock-down XBP1 mRNA in the liver. Mice were injected with PBS or siRNAs diluted in PBS at different doses through tail vain. Two days later, the liver was removed and the levels of (A) XBP1s is protein and (B) the total XBP1 mRNA were determined by western blot and the quantitative RT-PCR. (C) The status of IRE1 activation was determined by western blot. IRE1 protein is induced in XBP1 knock-down mouse liver, which displayed mobility shift on the gel, due to the constitutive phosphorylation and activation as in Xbp1 knock-out-mouse liver.
Figure 12B:
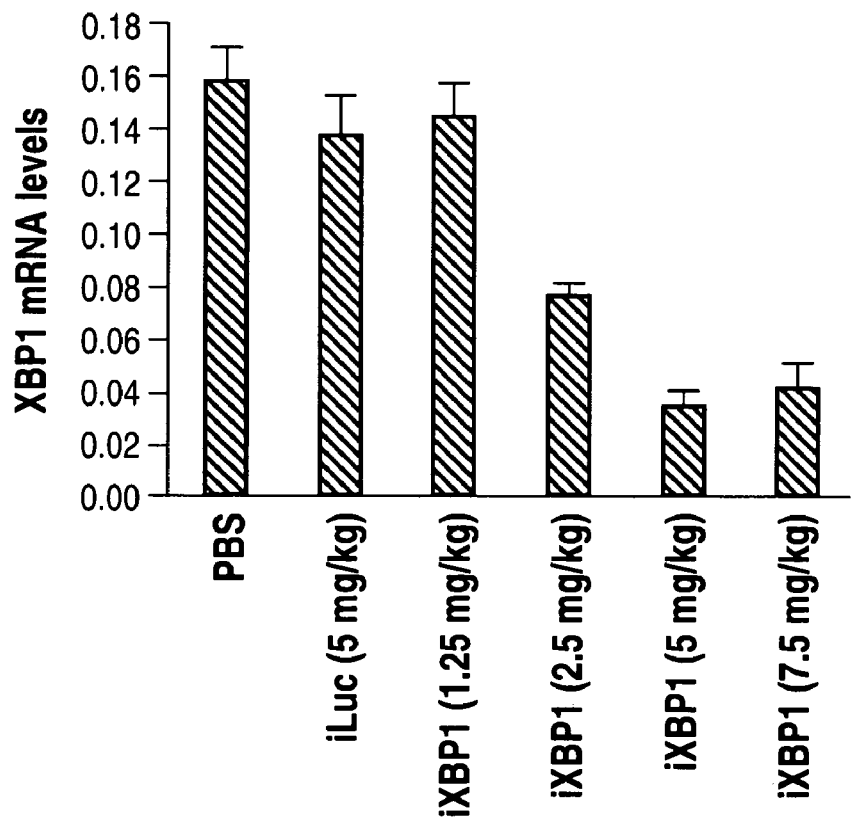
Figure 12C:
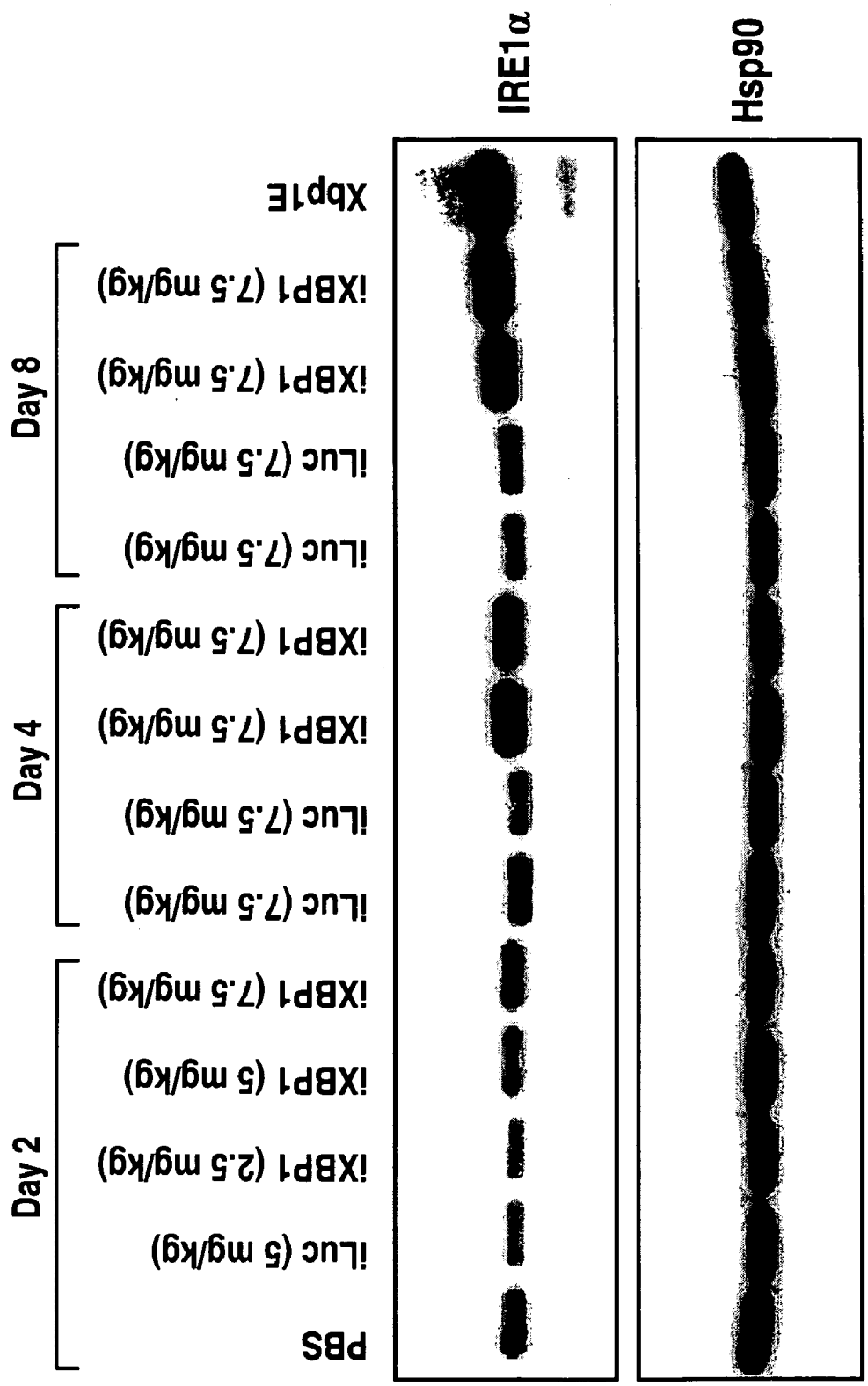
Figure 13A:
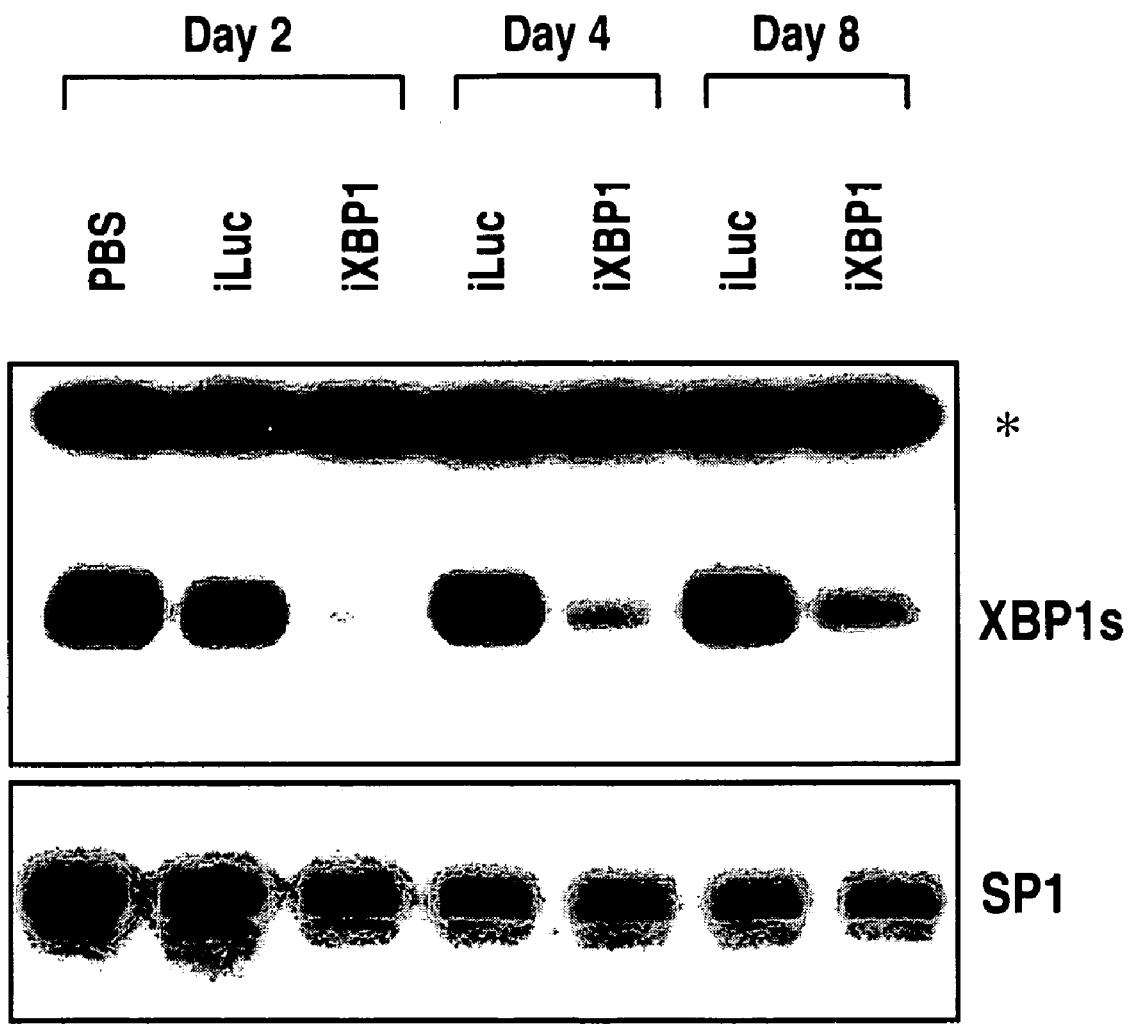
FIGS. 13A-B show that XBP1 silencing by siRNA and its effects on hepatic gene expression is durable. (A) Mice were intravenously injected with the control siRNA (luciferase) or XBP1 siRNA at 7.5 mg/kg. XBP1s protein levels at the indicated time points were determined by western blot in the liver nuclear extracts. SP1 protein serves as a loading control. (B) mRNA levels of indicated genes were determined by quantitative RT-PCR.
Figure 13B:
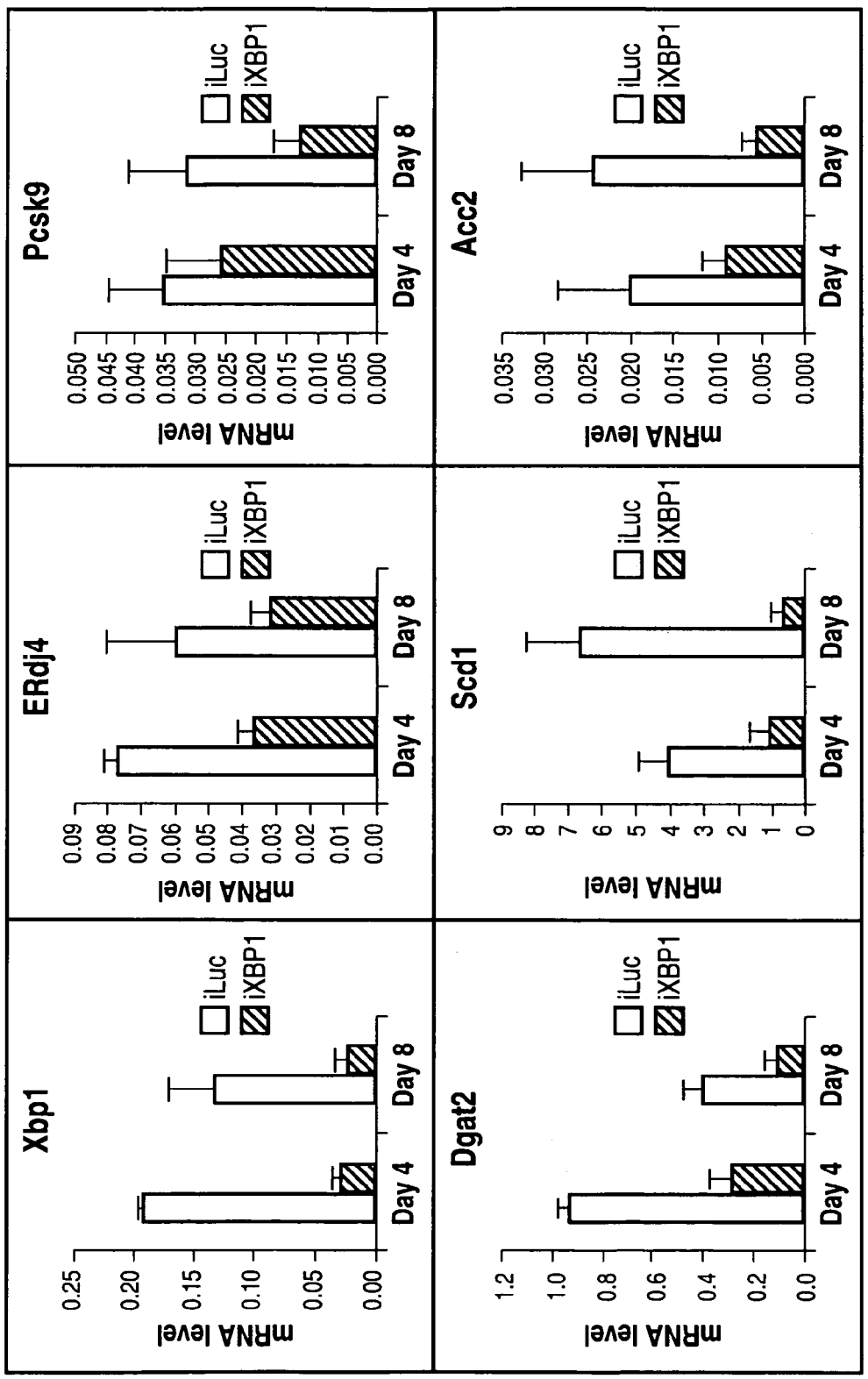
Figure 14B:
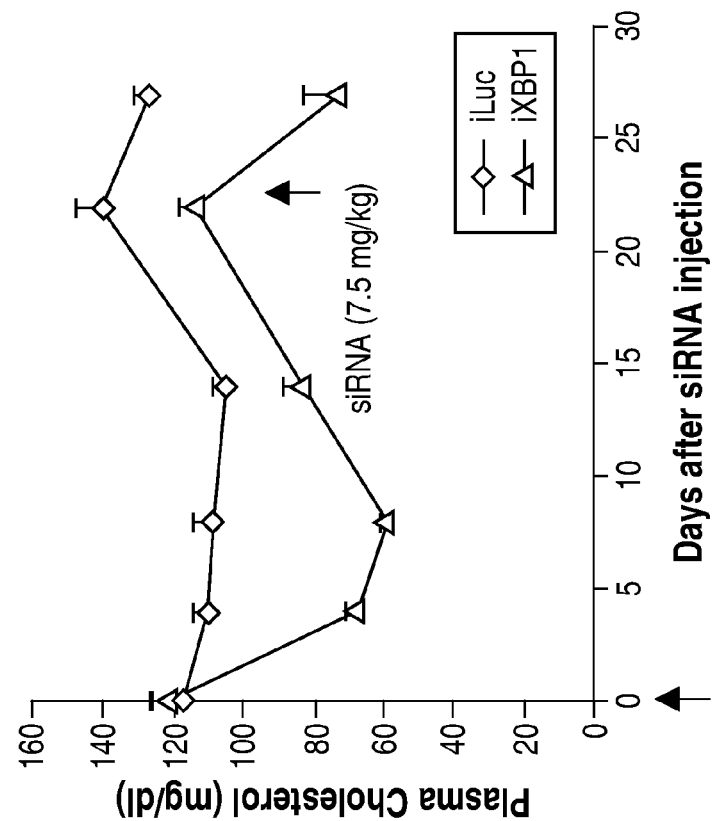
FIGS. 14A-B show the effects of XBP1 siRNA on plasma lipid levels. Male c57BL/6 mice (n=5 per group) were intravenously injected with the control siRNA (luciferase) or XBP1 siRNA at 7.5 mg/kg on day 0 and 23 as indicated by arrows. Total plasma (A) triglyceride and (B) cholesterol levels were measured along the time course.
Figure 14A:
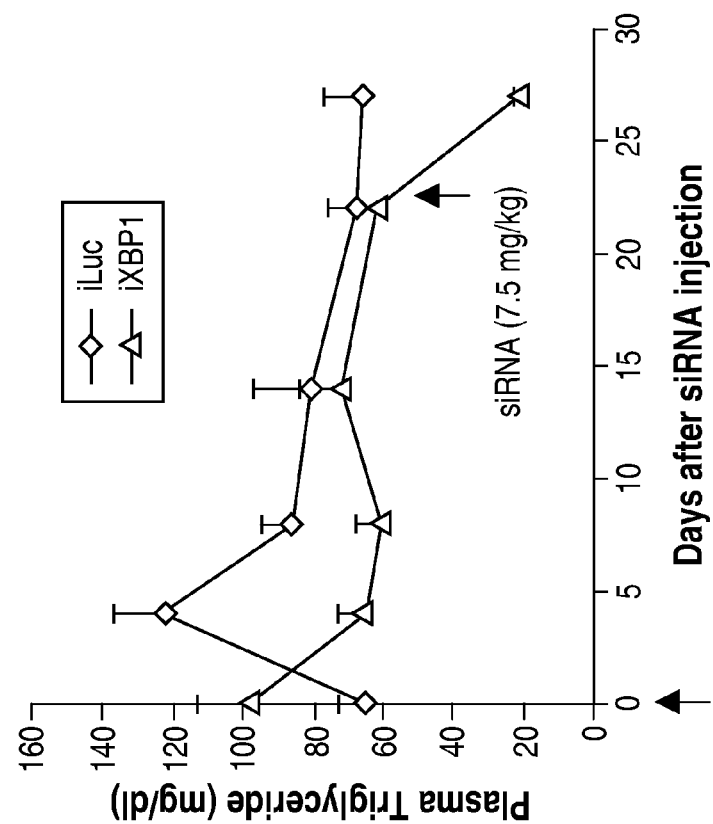

Wild-type (WT) control and Xbp1Δ mice were fed an atherogenic Paigen diet containing 0.96% cholesterol (Jackson Laboratory) for 7 days. Since cholesterol is being provided exogenously in this model, it was not expected that overall levels of serum cholesterol would be substantially diminished. Indeed, fed state plasma cholesterol levels were similar between WT and Xbp1Δ mice. However, the plasma cholesterol level measured after 4 h fasting was in fact significantly lowered in Xbp1Δ mice (FIGS. 10A and B).

Xbp1flox/flox; Mxcre or the WT control, Xbp1flox/flox, mice were injected with poly(IC) and fed 45% fat diet (Test Diet, 55629) for 5 months, starting from age 5 weeks. Since fat was being provided exogenously in this diet model, plasma triglyceride levels were similar between WT and Xbp1Δ. In contrast, cholesterol levels remained low in Xbp1Δ mice, even though WT hepatocytes had regenerated approximately 50% of hepatocytes in Xbp1Δ mouse liver during the 5 month period of the experiment. Interestingly, serum alanine aminotransferase (ALT) level, a liver damage marker, was significantly lower in Xbp1Δ mice, suggesting protection from high fat diet-induced lipotoxicity. No change in glucose/insulin homeostasis in Xbp1Δmice, as determined by blood glucose and insulin level and standard glucose tolerance (GTT) and insulin tolerence tests (ITT) were observed. This latter result may be explained by the partial deletion of XBP1 in this particular experiment (FIGS. 11A-D).

Example 9

RNAi Downmodulation of XBP-1 and IRE-1

Liposome encapsulated XBP-1 and IRE-1 siRNAs are tested in vitro and then in vivo.

In vitro experiments involve the analysis of XBP-1 and IRE-1 siRNAs for their ability to inhibit IRE1 or XBP1 mRNA and protein in primary hepatocytes and in a mouse and rat hepatoma cell line.

In vivo XBP1 and IRE-specific siRNAs or mismatched siRNAs are encapsulated in stable nucleic acid lipid particles (SNALP) and administered by intravenous injection to mice for example at doses of 1, 2.5 mg/kg, 7.5 mg/kg. Empty SNALP vesicles are also injected as an additional control. Serial measurements of XBP1s RNA and protein levels in liver and serum cholesterol and lipids are obtained starting from 0 hours and every 24 hours until day 12 after administration.

XBP-1 siRNAs or mismatched siRNAs encapsulated in stable nucleic acid lipid particles (SNALP) were administered by intravenous injection to WT mice at doses ranging from 1 to 7.5 mg/kg. Serum cholesterol and triglycerides, the extent of XBP1 knockdown in liver and the expression of XBP1-controlled lipogenic enzymes were measured. A greater than 90% reduction in XBP1s protein levels in liver was observed along with reduction in lipogenic enzyme expression. A greater than 90% reduction in XBP1s protein levels in liver was observed along with reduction in lipogenic enzyme expression. A dramatic decrease in both cholesterol and triglycerides was observed. Constitutive activation of IRE1a in the XBP1 siRNA injected mice, similar to what was observed in the Xbp1Δ mice was also observed, indicating that siRNA knock-down mimics genetic deletion (FIGS. 12A-C, 13A-B, and 14A-B). These data are robust proof that targeting XBP1 in liver can substantially lower serum lipids.

The same siRNAs are administered to the dietary and genetic animal models of metabolic disorders described in Example 8 (above).

In vivo, transient reduction of XBP-1 using siRNA treatment results in reduction in serum triglyceride and cholesterol levels.

Example 10

Identification of Small Molecule Inhibitors of XBP1s

A. Small-molecule Microarrays (SMMs)

SMMs are prepared by coating glass microscope slides with a short Fmoc-protected polyethylene glycol spacer. Following deprotection with piperidine, 1,6-diisocyanatohexane is coupled to the slides by urea bond formation to establish a reactive isocyanate surface. Stock solutions of small molecules are printed onto the slides using a microarrayer, and the slides are exposed to pyridine vapor to catalyze the covalent attachment of the molecules to the slide surface. SMMs are screened by incubation with a small volume of the protein of interest, either purified or from a cell lysate, followed by incubation with a fluorescently labeled antibody against either the protein or an epitope tag. Fluorescent features, detected with a standard microarray scanner, indicate putative protein-small molecule interactions. As a result, this technology greatly improves the capability of SMMs to identify novel protein-ligand interactions. Recombinant XBP1 protein of 213 aa (e.g., comprising the transactivation domain of XBP-1s, e.g., amino acid residues 159 to 371) has been purified and run through the SMM screen. Compounds identified in this screen have been assayed in a secondary screen, e.g., a UPR reporter assay (see, e.g., FIGS. 8A and 8B).

Tertiary assays are performed on compounds that inhibit the transactivation of XBP-1 in the reporter assay and include, e.g., determining the effect of compounds on hepatic lipogenesis by quantifying the rate of free fatty acid and sterol synthesis from hepatoma cell cultures. Hepatoma cells are cultured in the presence of varying doses of compound at 72 hours are labeled with 14C acetate and cultured for an additional 18 h.

B. High-Throughput Assays (HTS)

Figure 9:
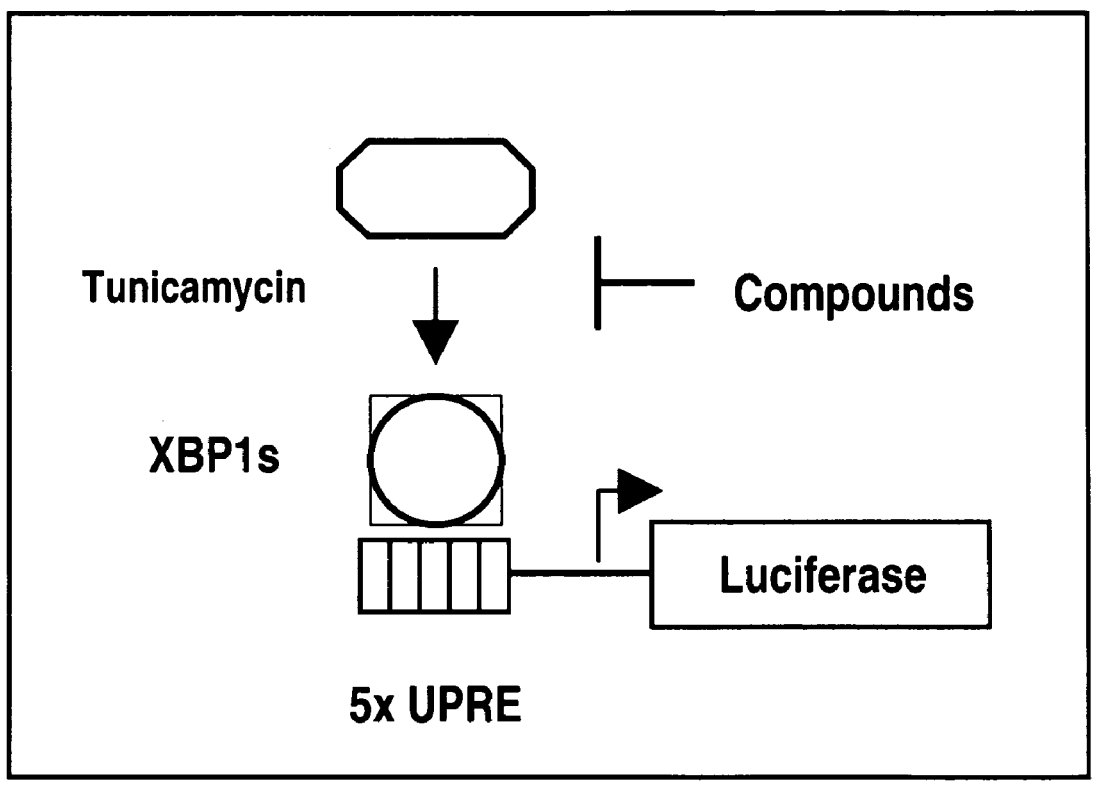
FIG. 9 is a shematic of an assay to identify compounds that inhibit the activity of XBP-1.

A reporter cell line for an HTS assay has been designed. It is a subclone of HeLa that expresses the UPRE, driving a luciferase reporter. Upon treatment with tunicamycin, the UPRE reporter is activated and luciferase activity is generated (FIG. 9). This assay will be utilized in a 384-well format to identify compounds, e.g., antagonists, that inhibit XBP-1 IRE-1 interaction and signaling.

HeLa cells are cultured (3000 cells/well) in a 384-well plate, treated with tunicamycin (0.5 ug/ml) and incubated for (16 hours) with compounds. Such cells treated with an XBP-1 shRNA or with MG-132, a known IRE-1 inhibitor abolish luciferase activity.

Compounds that are identified as inhibiting the signaling of XBP-1 and IRE-1 are further assayed as described below.

Secondary screens include measuring the effect of compounds on primary wild type and XBPΔ hepatocytes and on human HepG2 hepatoma cells or McArdle-RH7777 rat hepatoma cells by, e.g., quantifying XBP1 splicing by RT-PCR; western blot analysis for XBP1s protein for those compounds that inhibit XBP1 splicing; determining the effect of compounds on their effect on expression of defined XBP1 target genes that encode lipogenic enzymes (DGAT, Scd1, Acc) by RT-PCR.

Tertiary screens include, e.g., determining the effect of compounds on hepatic lipogenesis by quantifying the rate of free fatty acid and sterol synthesis from hepatoma cell cultures. Hepatoma cells are cultured in the presence of varying doses of compound at 72 hours are labeled with 14C acetate and cultured for an additional 18 h.

The following methods are used for the tertiary assays described above.

Mouse primary wt and XBP1Δ hepatocytes or rodent hepatoma cell lines are treated with varying concentrations of glucose (2.5 mM, 5 mM and 25 mM) for 24 h, and XBP1s protein and mRNA levels assessed by western blot and real time PCR.

Lipid synthesis. The rates of fatty acids and sterol synthesis are measured in hepatoma cells plated in 60 mm dishes are cultured in the presence of varying doses of 1.5 µl of [1-14C] acetate (57.5 mCi/mmol, Sigma) for 18 h. Cells are washed twice with PBS, resuspended in 1 ml PBS and mixed with 2.5 ml of 7% potassium hydroxide in 70% methanol. After incubation for 3 h at 95° C., sterols are extracted three times with 3.5 ml petroleum ether. The remaining aqueous phase is mixed with 0.47 ml of sulfuric acid and extracted three times with 3.5 ml petroleum ether for fatty acids. The organic phase is dried under low heat, and measured for [14C] level using a liquid scintillation counter.

Example 11

XBP-1 Controls PCSK9 Expression

Figure 15:
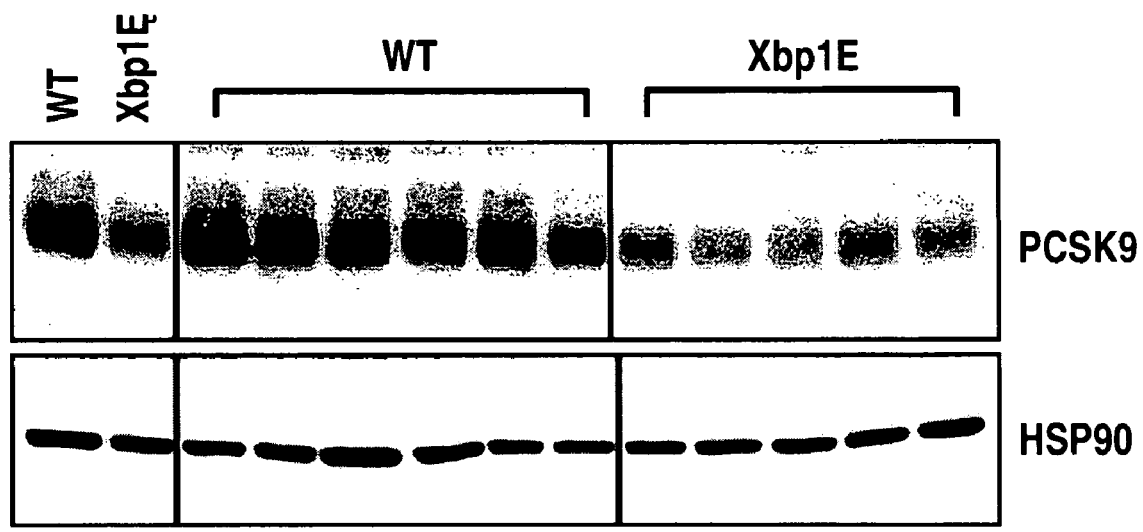
FIG. 15 depict the expression of the PCSK9 gene in the wild-type and XBP-1 deficient liver.

As described above, it was determined whether XBP-1 regulates the expression of genes involved in glycolysis and lipid synthesis pathways. Gene expression profiling revealed that critical lipogenic genes such as stearyl coA desaturase 1 (Scd1), diacyl glycerol acetyltransferase 2 (Dgat2), and acetyl coA carboxylase 2 (Acc2) were significantly down-regulated in XBP-1Δ liver, and these observations were verified by Northern blot and real time RT-PCR analyses (FIGS. 4a and b). It was also discovered that XBP-1 regulates the expression of proprotein convertase subtilisin/kexin type 9 (PCSK9) (FIG. 15).

PCSK9 acts to control the degradation of the LDL receptor: humans and mice with inactivating PCSK9 mutations have high levels of LDLR and low levels of serum cholesterol. As demonstrated herein, XBP1 was shown to control levels of serum cholesterol but any effect of XBP1 on HMGCoA reductase had been ruled out (see above). Therefore, the regulation of PCSK9 by XBP1 contributes to the profound hypocholesterolemia observed in XBP1 deficient mice.

Equivalents

Those skilled in the art will recognize, or be able to ascertain using no more than routine experimentation, many equivalents to the specific embodiments and methods described herein. Such equivalents are intended to be encompassed by the scope of the following claims.

What is claimed is:

1. A method of identifying a compound that is useful in treating and/or preventing dyslipidemia comprising, providing a cell comprising at least one expression construct comprising a DNA molecule encoding an XBP-1 polypeptide and a DNA molecule encoding an IRE-1 polypeptide;
   a) contacting the cell with each member of a library of test compounds;
   b) determining the activity of the XBP-1 polypeptide in the presence and absence of the test compound;
   c) selecting from the library of test compounds a compound of interest that downmodulates the activity of the XBP-1 polypeptide;
   d) determining the effect of the compound on de novo hepatic lipogenesis;
   e) selecting a compound of interest that downmodulates de novo hepatic lipogenesis as compared to an appropriate control, thereby identifying a compound that is useful in treating and/or preventing dyslipidemia.

2. The method of claim 1, wherein the effect of the compound on XBP-1 activity is determined by measuring the binding of XBP-1 to IRE-1.

3. The method of claim 1, wherein the effect of the compound on XBP-1 activity is determined by assaying the activity of IRE-1.

4. The method of claim 3, wherein the activity of IRE-1 is a kinase activity.

5. The method of claim 3, wherein the activity of IRE-1 is an endoribonuclease activity.

6. The method of claim 1, wherein the effect of the compound on XBP-1 activity is determined by assaying XBP-1 and/or IRE-1 protein levels.

7. The method of claim 1, wherein the XBP-1 polypeptide comprises a transactivation domain and the cell further comprises a vector comprising a regulatory element responsive to the XBP-1 transactivation domain operatively linked to a reporter gene and the effect of the compound on the activity of the polypeptide is determined by evaluating the expression of the reporter gene in the presence and absence of the test compound.

8. The method of claim 1, wherein the cell comprises a recombinant expression vector encoding a spliced XBP-1 protein; and a vector comprising a regulatory element responsive to the spliced XBP-1 protein operatively linked a reporter gene and the effect of the compound on the activity of the polypeptide is determined by evaluating the expression of the reporter gene in the presence and absence of the test compound.

9. The method of claim 1, wherein the cell comprises a recombinant expression vector comprising a regulatory element responsive to XBP-1 spliced protein operatively linked a reporter gene, wherein the cell is contacted with an agent that induces ER stress, and the effect of the compound on the activity of the polypeptide is determined by evaluating the expression of the reporter gene in the presence and absence of the test compound.

10. The method of claim 7, 8, or 9, further comprising determining the effect of the identified compound on the ratio of unspliced XBP-1 mRNA to spliced XBP-1 mRNA.

11. The method of claim 7, 8, or 9, further comprising determining the effect of the identified compound on the production of XBP-1 protein.

12. The method of claim 1, further comprising providing an indicator cell comprising a glucose-dependent promoter operably linked to a reporter gene, wherein the cell in cultured in the presence of glucose, and the effect of the compound on de novo hepatic lipogenesis is determined by evaluating the expression of the reporter gene in the presence and absence of the test compound.

13. The method of claim 1, wherein the effect of the compound on de novo hepatic lipogenesis is determined by determining the effect of the compound on level of cholesterol and/or triglyceride.

14. The method of claim 1, wherein determining the ability of the compound to modulate de novo hepatic lipogenesis comprises determining the expression of SREBP and/or chREBP.

15. The method of claim 1, wherein the ability of the compound to modulate de novo lipogenesis comprises determining the expression of a lipogenic gene.

16. The method of claim 1, wherein:
the cell further comprises a DNA molecule to which XBP-1 binds, wherein the DNA molecule comprises a promoter selected from the group consisting of a Dgat2 promoter, a Scd1 promoter, an Acc2 promoter; and a PCSK9 promoter; and
the effect of the test compound on de novo hepatic lipogenesis is determined by evaluating the binding of XBP-1 to the DNA molecule in the presence and absence of the test compound.

17. The method of claim 1, further comprising administering the test compound identified as useful in modulating dyslipidemia to a non-human animal and determining the effect of the identified compound on obesity and/or insulin resistance in the non-human animal.

18. The method of claim 1, further comprising administering the test compound identified as useful in modulating dyslipidemia to a non-human animal and determining the effect of the compound on at least one of aspartate aminotransferase levels, alanine aminotransferase levels, liver cell inflammation, and the presence of triglyceride vacuoles in liver cells.

19. The method of claim 1, further comprising determining the effect of the compound on at least one of serum triglycerides, total cholesterol and the distribution of cholesterol among LDL, IDL, and HDL.

* * * * *

SEQUENCE LISTING

<160> NUMBER OF SEQ ID NOS: 27

<210> SEQ ID NO 1
<211> LENGTH: 26
<212> TYPE: DNA
<213> ORGANISM: Mus sp.

<400> SEQUENCE: 1
cagcactcag actacgtgca cctctg                                        26

<210> SEQ ID NO 2
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 2
gggattcatg aatggccctt a                                             21

<210> SEQ ID NO 3
<211> LENGTH: 21
<212> TYPE: DNA
<213> ORGANISM: Artificial Sequence
<220> FEATURE:
<223> OTHER INFORMATION: /note="Description of Combined DNA/RNA
      Molecule: Synthetic oligonucleotide"

<400> SEQUENCE: 3
guuggacccu gucauguuut t                                             21

<210> SEQ ID NO 4
<211> LENGTH: 21
<212> TYPE: DNA
<213> ORGANISM: Artificial Sequence
<220> FEATURE:
<223> OTHER INFORMATION: /note="Description of Combined DNA/RNA
      Molecule: Synthetic oligonucleotide"

<400> SEQUENCE: 4
aaacaugaca ggguccaact t                                             21

<210> SEQ ID NO 5
<211> LENGTH: 21
<212> TYPE: DNA
<213> ORGANISM: Artificial Sequence
<220> FEATURE:
<223> OTHER INFORMATION: /note="Description of Combined DNA/RNA
      Molecule: Synthetic oligonucleotide"

<400> SEQUENCE: 5
gccauuaaug aacucauuct t                                             21

<210> SEQ ID NO 6
<211> LENGTH: 21
<212> TYPE: DNA
<213> ORGANISM: Artificial Sequence
<220> FEATURE:
<223> OTHER INFORMATION: /note="Description of Combined DNA/RNA
      Molecule: Synthetic oligonucleotide"

```
<400> SEQUENCE: 6
gaaugaguuc auuaauggct t                                              21

<210> SEQ ID NO 7
<211> LENGTH: 21
<212> TYPE: RNA
<213> ORGANISM: Artificial Sequence
<220> FEATURE:
<223> OTHER INFORMATION: /note="Description of Artificial Sequence:
      Synthetic oligonucleotide"

<400> SEQUENCE: 7
gaagagaacc acaaacuccu u                                              21

<210> SEQ ID NO 8
<211> LENGTH: 21
<212> TYPE: RNA
<213> ORGANISM: Artificial Sequence
<220> FEATURE:
<223> OTHER INFORMATION: /note="Description of Artificial Sequence:
      Synthetic oligonucleotide"

<400> SEQUENCE: 8
ggaguuugug guucucuucu u                                              21

<210> SEQ ID NO 9
<211> LENGTH: 21
<212> TYPE: RNA
<213> ORGANISM: Artificial Sequence
<220> FEATURE:
<223> OTHER INFORMATION: /note="Description of Artificial Sequence:
      Synthetic oligonucleotide"

<400> SEQUENCE: 9
gaggaucacc cugaauucau u                                              21

<210> SEQ ID NO 10
<211> LENGTH: 21
<212> TYPE: RNA
<213> ORGANISM: Artificial Sequence
<220> FEATURE:
<223> OTHER INFORMATION: /note="Description of Artificial Sequence:
      Synthetic oligonucleotide"

<400> SEQUENCE: 10
ugaauucagg gugauccucu u                                              21

<210> SEQ ID NO 11
<211> LENGTH: 21
<212> TYPE: RNA
<213> ORGANISM: Artificial Sequence
<220> FEATURE:
<223> OTHER INFORMATION: /note="Description of Artificial Sequence:
      Synthetic oligonucleotide"

<400> SEQUENCE: 11
cuuggaccca gucauguucu u                                              21

<210> SEQ ID NO 12
<211> LENGTH: 21
<212> TYPE: RNA
<213> ORGANISM: Artificial Sequence
<220> FEATURE:
<223> OTHER INFORMATION: /note="Description of Artificial Sequence:
      Synthetic oligonucleotide"
```

```
<400> SEQUENCE: 12
gaacaugacu ggguccaagu u                                         21

<210> SEQ ID NO 13
<211> LENGTH: 21
<212> TYPE: RNA
<213> ORGANISM: Artificial Sequence
<220> FEATURE:
<223> OTHER INFORMATION: /note="Description of Artificial Sequence:
      Synthetic oligonucleotide"

<400> SEQUENCE: 13
aucugcuuuc auccagccau u                                         21

<210> SEQ ID NO 14
<211> LENGTH: 21
<212> TYPE: RNA
<213> ORGANISM: Artificial Sequence
<220> FEATURE:
<223> OTHER INFORMATION: /note="Description of Artificial Sequence:
      Synthetic oligonucleotide"

<400> SEQUENCE: 14
uggcuggaug aaagcagauu u                                         21

<210> SEQ ID NO 15
<211> LENGTH: 21
<212> TYPE: RNA
<213> ORGANISM: Artificial Sequence
<220> FEATURE:
<223> OTHER INFORMATION: /note="Description of Artificial Sequence:
      Synthetic oligonucleotide"

<400> SEQUENCE: 15
gccccuaguc uuagagauau u                                         21

<210> SEQ ID NO 16
<211> LENGTH: 21
<212> TYPE: RNA
<213> ORGANISM: Artificial Sequence
<220> FEATURE:
<223> OTHER INFORMATION: /note="Description of Artificial Sequence:
      Synthetic oligonucleotide"

<400> SEQUENCE: 16
uaucucuaag acuaggggcu u                                         21

<210> SEQ ID NO 17
<211> LENGTH: 21
<212> TYPE: RNA
<213> ORGANISM: Artificial Sequence
<220> FEATURE:
<223> OTHER INFORMATION: /note="Description of Artificial Sequence:
      Synthetic oligonucleotide"

<400> SEQUENCE: 17
gaaccuguag aagaugaccu u                                         21

<210> SEQ ID NO 18
<211> LENGTH: 21
<212> TYPE: RNA
<213> ORGANISM: Artificial Sequence
<220> FEATURE:
<223> OTHER INFORMATION: /note="Description of Artificial Sequence:
      Synthetic oligonucleotide"
```

-continued

<400> SEQUENCE: 18
ggucaucuuc uacagguucu u                                              21

<210> SEQ ID NO 19
<211> LENGTH: 21
<212> TYPE: RNA
<213> ORGANISM: Artificial Sequence
<220> FEATURE:
<223> OTHER INFORMATION: /note="Description of Artificial Sequence:
      Synthetic oligonucleotide"

<400> SEQUENCE: 19
cguauacagg cugccaucau u                                              21

<210> SEQ ID NO 20
<211> LENGTH: 21
<212> TYPE: RNA
<213> ORGANISM: Artificial Sequence
<220> FEATURE:
<223> OTHER INFORMATION: /note="Description of Artificial Sequence:
      Synthetic oligonucleotide"

<400> SEQUENCE: 20
caagcucaac uacuugaggu u                                              21

<210> SEQ ID NO 21
<211> LENGTH: 21
<212> TYPE: RNA
<213> ORGANISM: Artificial Sequence
<220> FEATURE:
<223> OTHER INFORMATION: /note="Description of Artificial Sequence:
      Synthetic oligonucleotide"

<400> SEQUENCE: 21
ccucaaguag uugagcuugu u                                              21

<210> SEQ ID NO 22
<211> LENGTH: 15
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 22
tggatgacgt gtaca                                                     15

<210> SEQ ID NO 23
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 23
tcgagacagg tgctgacgtg gcgattcc                                       28

<210> SEQ ID NO 24
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic oligonucleotide"

```
<400> SEQUENCE: 24
gggattcatg aatggccctt a                                              21

<210> SEQ ID NO 25
<211> LENGTH: 8
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 25 tgacgtgr                                                              8

<210> SEQ ID NO 26
<211> LENGTH: 21
<212> TYPE: RNA
<213> ORGANISM: Artificial Sequence
<220> FEATURE:
<223> OTHER INFORMATION: /note="Description of Artificial Sequence:
      Synthetic oligonucleotide"

<400> SEQUENCE: 26
ugauggcagc cuguauacgu u                                              21

<210> SEQ ID NO 27
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic oligonucleotide"
<220> FEATURE:
<221> NAME/KEY: misc_feature
<222> LOCATION: (6)..(14)
<223> OTHER INFORMATION: n is a, c, g, or t, unknown or other

<400> SEQUENCE: 27
ccaatnnnnn nnnnccacg                                                 19
```